(12) United States Patent
Heo et al.

(10) Patent No.: US 11,504,349 B2
(45) Date of Patent: Nov. 22, 2022

(54) COMPOSITION FOR PREVENTING OR TREATING TNF-RELATED DISEASES, CONTAINING NOVEL DERIVATIVE AS ACTIVE INGREDIENT, AND METHOD FOR INHIBITING TNF ACTIVITY BY USING SAME

(71) Applicant: ILAB, Gyeonggi-do (KR)

(72) Inventors: Tae-Hwe Heo, Gyeonggi-do (KR); Kye Jung Shin, Seoul (KR)

(73) Assignee: ILAB, Bucheon-si (KR)

( * ) Notice: Subject to any disclaimer, the term of this patent is extended or adjusted under 35 U.S.C. 154(b) by 46 days.

(21) Appl. No.: 16/757,112

(22) PCT Filed: Jul. 12, 2018

(86) PCT No.: PCT/KR2018/007922
§ 371 (c)(1),
(2) Date: Apr. 17, 2020

(87) PCT Pub. No.: WO2019/078452
PCT Pub. Date: Apr. 25, 2019

(65) Prior Publication Data
US 2020/0246304 A1    Aug. 6, 2020

(30) Foreign Application Priority Data

Oct. 19, 2017  (KR) .......................... 10-2017-0135899

(51) Int. Cl.
*A61K 31/352*    (2006.01)
*A61K 9/00*      (2006.01)
(Continued)

(52) U.S. Cl.
CPC .......... *A61K 31/352* (2013.01); *A61K 9/0056* (2013.01); *A61K 45/06* (2013.01); *C07D 311/30* (2013.01)

(58) Field of Classification Search
CPC .... A61K 31/352; A61K 9/0056; A61K 45/06; A61K 31/353; C07D 311/30;
(Continued)

(56) References Cited

U.S. PATENT DOCUMENTS 4,886,806 A    12/1989   Walenta et al.

FOREIGN PATENT DOCUMENTS

| KR | 20080013162 A | 2/2008 |
| KR | 20120096764 A | 8/2012 |

(Continued)

OTHER PUBLICATIONS

Cheng, Shu-Chen, et al., "Quercetin Inhibits the Production of IL-1 Induced Inflammatory Cytokines and Chemokines in ARPE-19 Cells via the MAPK and NF-κB Signaling Pathways", Int. J. Mol. Sci. 2019, 20, 2957, Jun. 17, 2019, 1-24.

(Continued)

*Primary Examiner* — Taylor V Oh
(74) *Attorney, Agent, or Firm* — Sughrue Mion, PLLC

(57) ABSTRACT

The present invention relates to: a 4-benzopyranone derivative and a pharmaceutically acceptable salt, solvate, racemate, or stereoisomer thereof; a composition for preventing, alleviating or treating TNF-related diseases, containing the same as an active ingredient; and a method for treating TNF-related diseases, a reagent composition for inhibiting TNF, and a method for inhibiting TNF, all of which use the same. The compositions can be orally administered so as not to cause injection side effects, do not cause immunological tolerance, and can effectively inhibit a TNF activity by being directly bound to TNF while facilitating co-administering with a conventional oral preparation and dosage control.

6 Claims, 10 Drawing Sheets

(51) Int. Cl.
  *A61K 45/06* (2006.01)
  *C07D 311/30* (2006.01)
(58) Field of Classification Search
  CPC .. C07D 405/04; C07D 409/04; C07D 311/22; A61P 29/00; A23V 2002/00; A23V 2200/324; A23L 33/10
  USPC ........................................................ 514/456
  See application file for complete search history.

(56) References Cited

FOREIGN PATENT DOCUMENTS

| | | |
|---|---|---|
| KR | 20140132932 A | 11/2014 |
| KR | 20160101732 A | 8/2016 |
| KR | 20170043363 A | 4/2017 |
| WO | WO01/72735 A2 * | 10/2001 |

OTHER PUBLICATIONS

Dong, Qian , et al., "Efficient synthesis of functionalized chromones via a two-base mediated formal [3+3] cycloaddition", Elsevier—Tetrahedron Letters 57 (2016) 2116-2120, Apr. 5, 2016.
Fischer, Jens A., et al., "Combined Inhibition of Tumor Necrosis Factor Alpha and Interleukin-17 as a Therapeutic Opportunity in Rheumatoid Arthritis", Arthritis & Rheumatology, vol. 67, No. 1, Jan. 2015, pp. 51-62, Sep. 23, 2014.
Gokhale, Jayanti P., et al., "Quercetin loaded nanoemulsion-based gel for rheumatoid arthritis: In vivo and in vitro studies", Biomedicine & Pharmacotherapy 112 (2019) 108622, Jan. 23, 2019.
Granado-Serrano, Ana Belen, et al., "Quercetin Attenuates TNF-Induced Inflammation in Hepatic Cells by Inhibiting the NF-κB Pathway", Nutrition and Cancer, 64(4), 588-598, 2012.
Haleagrahara, Nagaraja , et al., "Flavonoid quercetin-methotrexate combination inhibits inflammatory mediators and matrix metalloproteinase expression, providing protection to joints in collagen-induced arthritis", Inflammopharmacology, Apr. 3, 2018.
Haleagrahara, Nagaraja , et al., "Therapeutic effect of quercetin in collagen-induced arthritis", Biomedicine & Pharmacotherapy 90 (2017) 38-46, Mar. 9, 2017, 1-9.
Lee, Chung Soo, et al., "Quercetin-3-O-(2'-galloyl)-α-L-rhamnopyranoside inhibits TNF-α-activated NF-κB-induced inflammatory mediator production by suppressing ERK activation", International Immunophamnacology 16 (2013) 481-487, May 14, 2013.
Lee, Jisun , et al., "The immunostimulating activity of quercetin 3-O-xyloside in murine macrophages via activation of the ASK1/MAPK/NF-κB signaling pathway", International Immunopharmacology 31 (2016) 88-97, Dec. 17, 2015.
Lin, Jian-Ping , et al., "Transition metal-free one-pot synthesis of 2-substituted 3-carboxy-4-quinolone and chromone derivatives", Chem. Commun., 2013,49, 5313-5315, Apr. 21, 2013.
Ma, Li, et al., "A Novel Small-molecule Tumor Necrosis Factor alpha Inhibitor Attenuates Inflammation in a Hepatitis Mouse Model", The Journal of Biological Chemistry vol. 289, No. 18, pp. 12457-12466,, May 2, 2014.
Nair, Madhavan P., et al., "The Flavonoid Quercetin Inhibits Proinflammatory Cytokine (Tumor Necrosis Factor Alpha) Gene Expression in Normal Peripheral Blood Mononuclear Cells via Modulation of the NF-kiloBeta System", Clinical and Vaccine Immunology, vol. 13, No. 3, Mar. 2006, p. 319-328.
O'Connell, James , et al., "Small molecules that inhibit TNF signalling by stabilising an asymmetric form of the trimer", Nature Communications | (2019) 10:5795, 1-12.
Ruiz, Pedro A., et al., "Quercetin Inhibits TNF-Induced NF-κB Transcription Factor Recruitment to Proinflammatory Gene Promoters in Murine Intestinal Epithelial Cells", Journal of Nutrition. 137: 1208-1215, 2007, Sep. 22, 2006.
Son, Young-Ok , et al., "Quercetin, a bioflavonoid, accelerates TNF-α-induced growth inhibition and apoptosis in MC3T3-E1 osteoblastic cells", European Journal of Pharmacology 529 (2006) 24-32, Nov. 28, 2005.
Totzke, Julianne , et al., "Takinib, a Selective TAK1 Inhibitor, Broadens the Therapeutic Efficacy of TNF-a Inhibition for Cancer and Autoimmune Disease", Cell Chemical Biology 24, 1029-1039, Aug. 17, 2017.
Wen, Xiaodong , et al., "The small molecule NSM00191 specifically represses the TNF-α/NF-κB axis in foot and ankle rheumatoid arthritis", International Journal of Biological Sciences 2018; 14(12): 1732-1744. doi: 10.7150/ijbs.24232, Oct. 3, 2018.
Yang, Yanlong , et al., "Triptolide inhibits the migration and invasion of rheumatoid fibroblast-like synoviocytes by blocking the activation of the JNK MAPK pathway", Elsevier—International Immunophamnacology 41 (2016) 8-16, Oct. 10, 2016.
Yoshida, Masahito , et al., "A concise total synthesis of biologically active frutinones via tributylphosphine-catalyzed tandem acyl transfer-cyclization", Elsevier—Tetrahedron 70 (2014) 3452-3458, Apr. 1, 2014.
Zhang, Jun , et al., "Therapeutic effect and mechanism of action of quercetin in a rat model of osteoarthritis", Journal of International Medical Research 0(0) 1-9, Aug. 9, 2019.
PCT International Search Report in PCT/KR2018/007922, dated Oct. 17, 2018, 4 pages.

* cited by examiner

|  | BUN (mg/dL) | Cr (mg/dL) |
|---|---|---|
| Control | 12.2 ± 3.21 | 0.10 ± 0.02 |
| CLP | 75.4 ± 14.2 | 0.44 ± 0.21 |
| CLP+TNF blocker | 21.8 ± 4.20 | 0.17 ± 0.07 |

COMPOSITION FOR PREVENTING OR TREATING TNF-RELATED DISEASES, CONTAINING NOVEL DERIVATIVE AS ACTIVE INGREDIENT, AND METHOD FOR INHIBITING TNF ACTIVITY BY USING SAME

CROSS-REFERENCE TO RELATED APPLICATIONS

This application is the National Stage entry of PCT/KR2018/007922, filed on Jul. 12, 2018, which claims priority to Republic of Korea Provisional Application Serial No. 10-2017-0135899, filed Oct. 19, 2017, the entire disclosures of which are hereby incorporated by reference herein.

TECHNICAL FIELD

The present invention relates to a novel 4-benzopyranone compound derivative, and a composition for preventing, alleviating or treating TNF-related diseases, containing the same as an active ingredient, and a method for inhibiting a TNF activity by using the same.

BACKGROUND ART

TNF is a key inflammatory cytokine, and is attracting attention as a major cause of autoimmune inflammatory diseases such as rheumatoid arthritis, inflammatory bowel disease, psoriasis, ankylosing spondylitis and the like. A variety of anti-TNF blockbuster biopharmaceuticals such as etanercept (Enbrel), adalimumab (Humira), infliximab (Remicade) and the like are actively used as a therapeutic agent in a variety of TNF-related diseases including rheumatoid arthritis. Anti-TNF biopharmaceuticals show an excellent efficacy in a short period of time, but they are expensive and require repetitive injections, so patients are highly repulsed. In addition, about one third of patients have no therapeutic effect, and tolerance occurs within a few years due to immunological side effects even in patients who have responded to the drugs. There are obvious disadvantages such as difficulty of storage because it is necessary to store them at low temperature. Anti-TNF biopharmaceuticals have unmet medical demand.

As a strategy to overcome this, efforts have been made to find small molecular materials that can be orally administered and act like antibodies by being directly bound to cytokines or their receptors [He et al. (2005). Science 310(5750): 1022-1025]. However, binding to cytokines and their receptors occurs as a bond between protein and protein in a large area, and inhibiting the same by small molecular materials has not been effective so far.

An article regarding to a small molecular material that dissociates the TNF trimer by being directly bound to TNF has been published [He et al. (2005). Science 310(5750): 1022-1025], a follow-up study seems to be stopped due to weak activity and the like. On the one hand, many small molecular material signaling inhibitors that block intracellular signaling are under development, and articles on the inhibitors of TNF expression or secretion that have unclear mechanisms have been published, but there is no data of in vivo activity. The development of small molecular material drugs that directly inhibit the binding between TNF and TNFR has not been successful so far.

DETAILED DESCRIPTION OF THE INVENTION

Technical Problem

It is an object of the present invention to provide a novel compound which shows an excellent inhibitory effect on a TNF activity.

It is another object of the present invention to provide a pharmaceutical composition which can effectively prevent or treat diseases by showing an excellent inhibitory effect on a TNF activity.

It is still another object of the present invention to provide a health functional food composition which can effectively prevent or alleviate diseases by showing an excellent inhibitory effect on a TNF activity.

It is still another object of the present invention to provide a method for treating TNF-related diseases effectively.

It is still another object of the present invention to provide a reagent composition for inhibiting a TNF activity in vitro.

It is still another object of the present invention to provide a method for inhibiting a TNF activity in an animal excluding a human.

Solution to Problem

In order to accomplish the object described above, the present invention provides a 4-benzopyranone derivative represented by Formula 1 below, a pharmaceutically acceptable salt, solvate, racemate, or stereoisomer thereof.

In order to accomplish another object described above, the present invention provides a pharmaceutical composition for preventing or treating TNF-related diseases, wherein the pharmaceutical composition contains a 4-benzopyranone derivative represented by Formula 1 below, a pharmaceutically acceptable salt, solvate, racemate, or stereoisomer thereof as an active ingredient, and inhibits a TNF activity by being directly bound to tumor necrosis factor (TNF).

In order to accomplish still another object described above, the present invention provides a health functional food composition preventing or alleviating TNF-related diseases, wherein the health functional food composition contains a 4-benzopyranone derivative represented by Formula 1 below, a pharmaceutically acceptable salt, solvate, racemate, or stereoisomer thereof as an active ingredient, and inhibits a TNF activity by being directly bound to tumor necrosis factor (TNF).

In order to accomplish still another object described above, the present invention provides a method for treating TNF-related diseases, comprising a step of treating with a 4-benzopyranone derivative represented by Formula 1 below, a pharmaceutically acceptable salt, solvate, racemate, or stereoisomer thereof in a pharmaceutically effective amount.

In order to accomplish still another object described above, the present invention provides a reagent composition for inhibiting a TNF activity in vitro, containing a 4-benzopyranone derivative represented by Formula 1 below, a pharmaceutically acceptable salt, solvate, racemate, or stereoisomer thereof as an active ingredient.

In order to accomplish still another object described above, the present invention provides a method for inhibiting a TNF activity, comprising a step of treating an animal excluding a human with a 4-benzopyranone derivative represented by Formula 1 below, a pharmaceutically acceptable salt, solvate, racemate, or stereoisomer thereof.

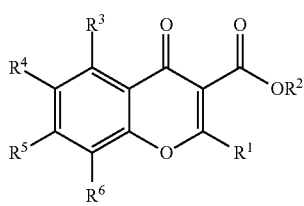

[Formula 1]

in which,

R[1] is heteroaryl or substituted phenyl;

R[2] is hydrogen or lower alkyl of (C1-C4); and

R[3], R[4], R[5], and R[6] are each independently hydrogen, halogen, or (C1-C4)alkoxy.

Effect of Invention

The present invention relates to a composition for preventing or treating TNF-related diseases, containing a 4-benzopyranone derivative compound as an active ingredient. The conventional protein TNF-inhibiting biopharmaceuticals are inconvenient for the administration in combination with other compound therapeutic agents, and can not be utilized for the development of a combination product. However, the TNF-inhibiting compound provided by the present invention is very easy to be administered in combination with other conventional compound therapeutic agents or to be utilized for the development of a combination product, and, in addition, has advantages such as excellent efficacy, low cost, non-invasive oral administration, non-immunogenicity, needlessness of refrigeration storage and the like, and thus, can be usefully utilized in a composition for preventing or treating TNF-related diseases.

BEST EMBODIMENT FOR WORKING THE INVENTION

Figure 1:
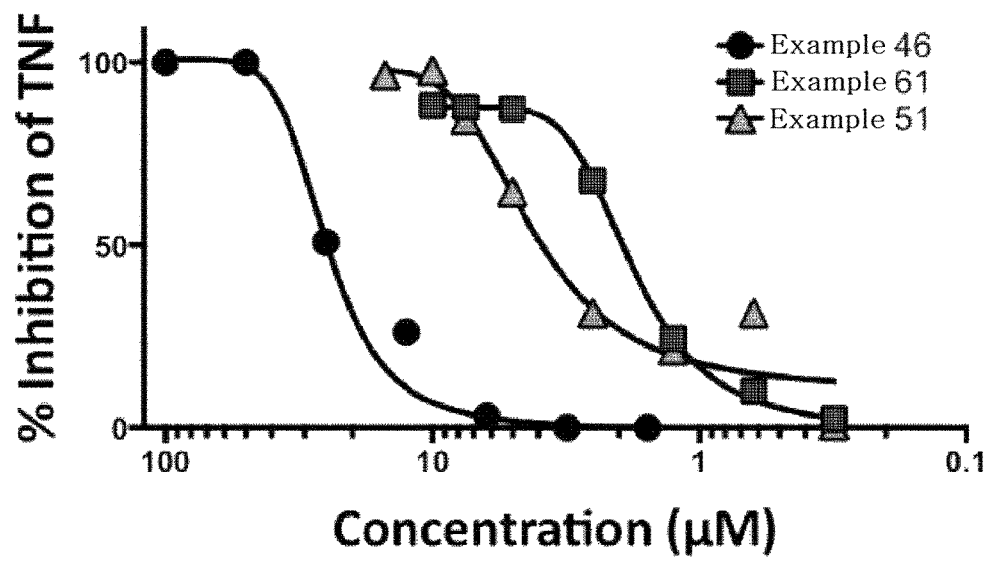
FIG. 1 is a graph showing the TNF-inhibiting ability of representative compounds inhibiting TNF (the compound of Example 46, the compound of Example 61, and the compound of Example 51) among the small molecular compounds synthesized in one example of the present invention depending on concentration.

Hereinafter, the present invention will be described in more detail.

The present invention provides a 4-benzopyranone derivative characterized by being represented by Formula 1, a pharmaceutically acceptable salt, solvate, racemate, or stereoisomer thereof:

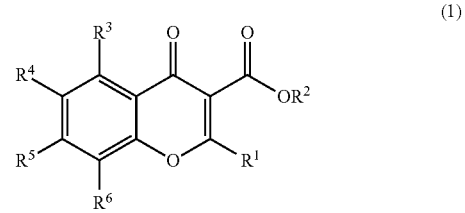

(1)

in which,

R[1] is heteroaryl or substituted phenyl;

R[2] is hydrogen or lower alkyl of (C1-C4); and

R[3], R[4], R[5], and R[6] are each independently hydrogen, halogen, or (C1-C4)alkoxy.

In one example of the present invention, a 4-benzopyranone derivative having a carboxy group at the 3-position as described above among the 4-benzopyranone compounds can be prepared through the method disclosed in Reaction Scheme 1 below.

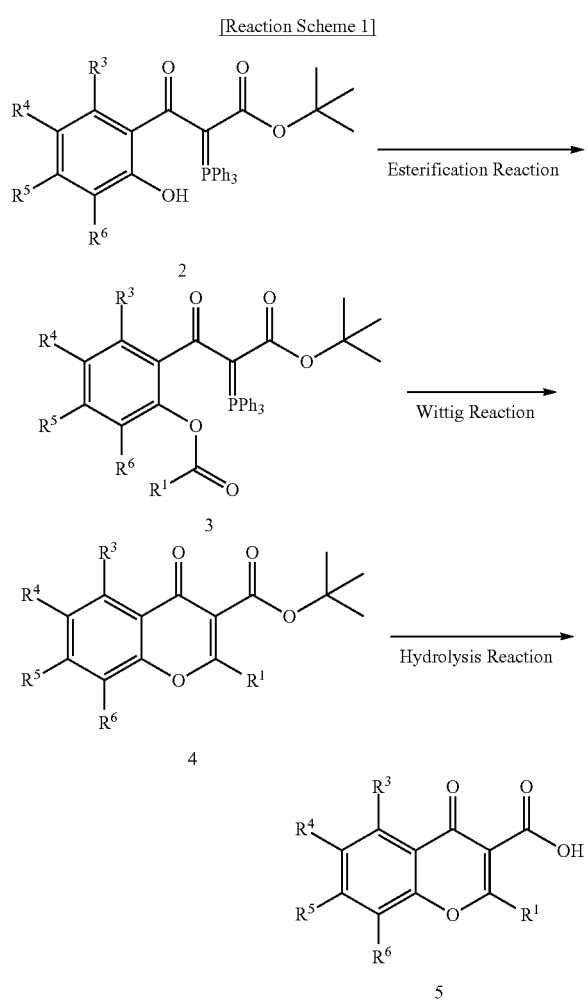

[Reaction Scheme 1]

A step of preparing the compound (3) by reacting the compound (2) with an acid chloride in the presence of a base and a catalyst (Step 1); a step of preparing the compound (4) by reacting the compound (3) prepared in Step 1 above through the intermolecular Wittig reaction (Step 2); and a step of preparing the compound (5) by de-esterifying the compound (4) prepared in Step 2 above under an acidic condition to remove the tertiary butyl group (Step 3).

Each preparation step of the present invention will be described specifically as follows: Step 1 is a step of preparing the compound (3) by reacting the compound (2) with heteroaromatic or benzoyl chloride in the presence of a base and a catalyst.

N,N-diisopropylethylamine, triethylamine, or pyridine may be used as the base, and 4-dimethylaminopyridine may be used as the catalyst. The acid chloride is used in a slight excess amount, preferably 1.05 equivalents, to result in the esterification reaction. It is possible to remove the acid chloride remaining after the reaction by the purification using chromatography or the reaction work-up method using a Girard-T ($H_2NNHCOCH_2N(CH_3)_3Cl$) reagent instead of chromatography. The acid chloride may be removed easily because the acid chloride reacts with the above Girard-T reagent to form a hydrazine derivative which is dissolved in water, and only the desired compound (3) remains in the organic layer, and all of the remains are contained in the aqueous layer.

The compound (2), which is the starting material of Step 1, may be obtained by reacting an O-acetylsalicylic acid chloride compound with a tertiary butoxy carbonyl methylene triphenylphosphorane compound in the presence of a reaction solvent of benzene or tetrahydrofuran and a catalyst of N,O-bistrimethylsilyl acetamide to prepare a phosphorane compound, and then, by removing an acetyl group through a deacetylation reaction using a base of dimethylamine, methylamine, or ammonia and a reaction solvent of tetrahydrofuran, methanol, or ethanol.

Next, Step 2 is a step of preparing the compound (4) by reacting the compound (3) prepared in Step 1 above through the intermolecular Wittig reaction. In this regard, benzene, toluene, xylene, or mesitylene may be used as a reaction solvent, and it is preferable to reflux with heating at 80 to 140° C. for 8 to 24 hours.

Next, Step 3 is a step of preparing the compound (5) by de-esterifying the compound (4) prepared in Step 2 above under an acidic condition to remove the tertiary butyl group. The de-esterification reaction may be carried out by reacting the compound with trifluoracetic acid in a carbon dichloride solvent. By the reaction, the tertiary butyl group may be removed from the carboxylic acid butyl ester compound (4) to obtain the 4-benzopyranone compound (5) having a carboxy group at the 3-position in Formula 1.

In addition to the compounds specified as the base material, the solvent, and the catalyst in each of the above-mentioned reactions, a compound capable of promoting the reaction may be used as a base material, a solvent, and a catalyst.

The products after the completion of each reaction or all reactions as decribed above may be separated and purified by a customary work-up method, for example, chromatography or recrystallization.

The compound of Formula 1 of the present invention can be synthesized by using the synthesis methods described above and can be obtained by all customary methods, and commercially available reagents can be also used.

The 4-benzopyranone compound of the present invention may be in the form of a pharmaceutically acceptable salt thereof. The salt includes the customary acid addition salts used in the field of compound inhibitors, for example, salts derived from inorganic acids such as hydrochloric acid, bromic acid, sulfuric acid, sulfamic acid, phosphoric acid, or nitric acid, and salts derived from organic acids such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, toluenesulfonic acid, oxalic acid, or trifluoroacetic acid. In addition, the salt includes salts derived from metals such as, for example, lithium, sodium, potassium, magnesium, or calcium in the form of customary metal salts. The acid addition salts or metal salts may be prepared according to customary methods known in the field of organic chemistry.

In addition, the 4-benzopyranone compound of the present invention may be in the form of a solvate thereof. The term "solvate" means a complex or aggregate formed by one or more solute molecules, i.e., a compound of Formula 1 or a pharmaceutically acceptable salt thereof, and one or more solvent molecules. The solvate may be, for example, a complex or aggregate formed with water, methanol, ethanol, isopropanol, or acetic acid.

In addition, the 4-benzopyranone compound of the present invention may be in the form of a stereoisomer thereof. The stereoisomer includes all stereoisomers such as enantiomers and diastereomers. The compound may be a stereoisomerically pure form or a mixture of one or more stereoisomers, for example, a racemic mixture. The separation of certain stereoisomers can be carried out by any one of customary methods known in the art. Specifically, in Formula 1 above, $R^1$ may be furanyl, thiophenyl, or substituted phenyl represented by

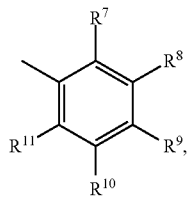

and $R^3$, $R^4$, $R^5$, $R^6$, $R^7$, $R^8$, $R^9$, $R^{10}$, and $R^{11}$ may be each independently hydrogen, chloro, bromo, fluoro, or methoxy.

More specifically, the 4-benzopyranone derivative may be selected from the group consisting of
2-(2-chlorophenyl)-3-carboxy-7-methoxy-(4H)-4-benzopyranone;
2-(2-chlorophenyl)-3-carboxy-(4H)-4-benzopyranone;
2-(2-furanyl)-3-carboxy-(4H)-4-benzopyranone;
2-(2-furanyl)-3-carboxy-8-methoxy-(4H)-4-benzopyranone;
2-(2-furanyl)-3-carboxy-7-methoxy-(4H)-4-benzopyranone;
2-(2-furanyl)-3-carboxy-6-methoxy-(4H)-4-benzopyranone;
2-(2-furanyl)-3-carboxy-8-methyl-(4H)-4-benzopyranone;
2-(2-furanyl)-3-carboxy-7-methyl-(4H)-4-benzopyranone;
2-(2-furanyl)-3-carboxy-6-methyl-(4H)-4-benzopyranone;
2-(2-furanyl)-3-carboxy-7-chloro-(4H)-4-benzopyranone;
2-(2-furanyl)-3-carboxy-6-chloro-(4H)-4-benzopyranone;
2-(2-furanyl)-3-carboxy-6-bromo-(4H)-4-benzopyranone;
2-(3-methylphenyl)-3-carboxy-(4H)-4-benzopyranone;
2-(3-methylphenyl)-3-carboxy-8-methoxy-(4H)-4-benzopyranone;
2-(3-methylphenyl)-3-carboxy-7-methoxy-(4H)-4-benzopyranone;
2-(3-methylphenyl)-3-carboxy-6-methoxy-(4H)-4-benzopyranone;
2-(3-methylphenyl)-3-carboxy-8-methyl-(4H)-4-benzopyranone;
2-(3-methylphenyl)-3-carboxy-7-methyl-(4H)-4-benzopyranone;
2-(3-methylphenyl)-3-carboxy-6-methyl-(4H)-4-benzopyranone;
2-(3-methylphenyl)-3-carboxy-7-chloro-(4H)-4-benzopyranone;
2-(3-methylphenyl)-3-carboxy-6-chloro-(4H)-4-benzopyranone;
2-(3-methylphenyl)-3-carboxy-6-bromo-(4H)-4-benzopyranone;
2-(2-thiophenyl)-3-carboxy-8-methoxy-(4H)-4-benzopyranone;
2-(2-thiophenyl)-3-carboxy-7-methoxy-(4H)-4-benzopyranone;
2-(2-thiophenyl)-3-carboxy-6-methoxy-(4H)-4-benzopyranone;
2-(2-thiophenyl)-3-carboxy-(4H)-4-benzopyranone;
2-(2-thiophenyl)-3-carboxy-8-methyl-(4H)-4-benzopyranone;
2-(2-thiophenyl)-3-carboxy-7-methyl-(4H)-4-benzopyranone;
2-(2-thiophenyl)-3-carboxy-6-methyl-(4H)-4-benzopyranone;
2-(2-thiophenyl)-3-carboxy-7-chloro-(4H)-4-benzopyranone;
2-(2-thiophenyl)-3-carboxy-6-chloro-(4H)-4-benzopyranone;
2-(2-thiophenyl)-3-carboxy-6-bromo-(4H)-4-benzopyranone;
2-(3,4-dimethoxyphenyl)-3-carboxy-(4H)-4-benzopyranone;
2-(3,4-dimethoxyphenyl)-3-carboxy-8-methyl-(4H)-4-benzopyranone;
2-(3,4-dimethoxyphenyl)-3-carboxy-7-methyl-(4H)-4-benzopyranone;
2-(3,4-dimethoxyphenyl)-3-carboxy-6-methyl-(4H)-4-benzopyranone;
2-(3,4-dimethoxyphenyl)-3-carboxy-7-chloro-(4H)-4-benzopyranone;
2-(3,4-dimethoxyphenyl)-3-carboxy-6-chloro-(4H)-4-benzopyranone;
2-(3,4-dimethoxyphenyl)-3-carboxy-6-bromo-(4H)-4-benzopyranone;
2-(3,4-dimethoxyphenyl)-3-carboxy-7-methoxy-(4H)-4-benzopyranone;
2-(3,4-dimethoxyphenyl)-3-carboxy-8-methoxy-(4H)-4-benzopyranone;
2-(3-fluorophenyl)-3-carboxy-(4H)-4-benzopyranone;
2-(3-fluorophenyl)-3-carboxy-8-methyl-(4H)-4-benzopyranone;
2-(3-fluorophenyl)-3-carboxy-7-methyl-(4H)-4-benzopyranone;
2-(3-fluorophenyl)-3-carboxy-6-methyl-(4H)-4-benzopyranone;
2-(3-fluorophenyl)-3-carboxy-7-chloro-(4H)-4-benzopyranone;
2-(3-fluorophenyl)-3-carboxy-6-chloro-(4H)-4-benzopyranone;
2-(3-fluorophenyl)-3-carboxy-6-bromo-(4H)-4-benzopyranone;
2-(3-fluorophenyl)-3-carboxy-7-methoxy-(4H)-4-benzopyranone;
2-(3,5-difluorophenyl)-3-carboxy-(4H)-4-benzopyranone;
2-(3,5-difluorophenyl)-3-carboxy-8-methyl-(4H)-4-benzopyranone;
2-(3,5-difluorophenyl)-3-carboxy-7-methyl-(4H)-4-benzopyranone;
2-(3,5-difluorophenyl)-3-carboxy-6-methyl-(4H)-4-benzopyranone;
2-(3,5-difluorophenyl)-3-carboxy-6-chloro-(4H)-4-benzopyranone;
2-(3,5-difluorophenyl)-3-carboxy-6-bromo-(4H)-4-benzopyranone;
2-(2,3-difluorophenyl)-3-carboxy-8-methyl-(4H)-4-benzopyranone;
2-(2,3-difluorophenyl)-3-carboxy-7-methyl-(4H)-4-benzopyranone;
2-(2,3-difluorophenyl)-3-carboxy-6-methyl-(4H)-4-benzopyranone;
2-(2,3-difluorophenyl)-3-carboxy-7-chloro-(4H)-4-benzopyranone;
2-(2,3-difluorophenyl)-3-carboxy-6-chloro-(4H)-4-benzopyranone;
2-(2,3-difluorophenyl)-3-carboxy-6-bromo-(4H)-4-benzopyranone;

2-(2,5-difluorophenyl)-3-carboxy-8-methyl-(4H)-4-benzopyranone;
2-(2,5-difluorophenyl)-3-carboxy-7-methyl-(4H)-4-benzopyranone;
2-(2,5-difluorophenyl)-3-carboxy-6-methyl-(4H)-4-benzopyranone;
2-(2,5-difluorophenyl)-3-carboxy-7-chloro-(4H)-4-benzopyranone;
2-(2,5-difluorophenyl)-3-carboxy-6-chloro-(4H)-4-benzopyranone;
2-(2,5-difluorophenyl)-3-carboxy-6-bromo-(4H)-4-benzopyranone;
2-(3,4-difluorophenyl)-3-carboxy-8-methyl-(4H)-4-benzopyranone;
2-(3,4-difluorophenyl)-3-carboxy-7-methyl-(4H)-4-benzopyranone;
2-(3,4-difluorophenyl)-3-carboxy-6-methyl-(4H)-4-benzopyranone;
2-(3,4-difluorophenyl)-3-carboxy-6-chloro-(4H)-4-benzopyranone;
2-(4-chlorophenyl)-3-carboxy-8-methyl-(4H)-4-benzopyranone;
2-(4-chlorophenyl)-3-carboxy-7-methyl-(4H)-4-benzopyranone;
2-(4-chlorophenyl)-3-carboxy-6-methyl-(4H)-4-benzopyranone;
2-(4-chlorophenyl)-3-carboxy-6-chloro-(4H)-4-benzopyranone;
2-(4-chlorophenyl)-3-carboxy-6-bromo-(4H)-4-benzopyranone;
2-(4-chlorophenyl)-3-carboxy-(4H)-4-benzopyranone; and
2-(4-chlorophenyl)-3-carboxy-8-methoxy-(4H)-4-benzopyranone.

In one example of the present invention, the 4-benzopyranone derivative compound may inhibit a TNF activity by being directly bound to tumor necrosis factor (TNF).

Furthermore, the present invention provides a pharmaceutical composition for preventing or treating TNF-related diseases or a health functional food composition for preventing or alleviating TNF-related diseases, wherein the composition contains a 4-benzopyranone derivative represented by Formula 1, a pharmaceutically acceptable salt, solvate, racemate, or stereoisomer thereof as an active ingredient, and inhibits a TNF activity by being directly bound to tumor necrosis factor (TNF):

(1)

in which,
$R^1$ is heteroaryl or substituted phenyl;
$R^2$ is hydrogen or lower alkyl of (C1-C4); and
$R^3$, $R^4$, $R^5$, and $R^6$ are each independently hydrogen, halogen, or (C1-C4)alkoxy.

Specifically, in Formula 1 above, $R^1$ may be furanyl, thiophenyl, or substituted phenyl represented by and $R^3$, $R^4$, $R^5$, $R^6$, $R^7$, $R^8$, $R^9$, $R^{10}$, and $R^{11}$ may be each independently hydrogen, chloro, bromo, fluoro, or methoxy.

More specifically, the 4-benzopyranone derivative may be selected from the group consisting of
2-(2-chlorophenyl)-3-carboxy-7-methoxy-(4H)-4-benzopyranone;
2-(2-chlorophenyl)-3-carboxy-(4H)-4-benzopyranone;
2-(2-furanyl)-3-carboxy-(4H)-4-benzopyranone;
2-(2-furanyl)-3-carboxy-8-methoxy-(4H)-4-benzopyranone;
2-(2-furanyl)-3-carboxy-7-methoxy-(4H)-4-benzopyranone;
2-(2-furanyl)-3-carboxy-6-methoxy-(4H)-4-benzopyranone;
2-(2-furanyl)-3-carboxy-8-methyl-(4H)-4-benzopyranone;
2-(2-furanyl)-3-carboxy-7-methyl-(4H)-4-benzopyranone;
2-(2-furanyl)-3-carboxy-6-methyl-(4H)-4-benzopyranone;
2-(2-furanyl)-3-carboxy-7-chloro-(4H)-4-benzopyranone;
2-(2-furanyl)-3-carboxy-6-chloro-(4H)-4-benzopyranone;
2-(2-furanyl)-3-carboxy-6-bromo-(4H)-4-benzopyranone;
2-(3-methylphenyl)-3-carboxy-(4H)-4-benzopyranone;
2-(3-methylphenyl)-3-carboxy-8-methoxy-(4H)-4-benzopyranone;
2-(3-methylphenyl)-3-carboxy-7-methoxy-(4H)-4-benzopyranone;
2-(3-methylphenyl)-3-carboxy-6-methoxy-(4H)-4-benzopyranone;
2-(3-methylphenyl)-3-carboxy-8-methyl-(4H)-4-benzopyranone;
2-(3-methylphenyl)-3-carboxy-7-methyl-(4H)-4-benzopyranone;
2-(3-methylphenyl)-3-carboxy-6-methyl-(4H)-4-benzopyranone;
2-(3-methylphenyl)-3-carboxy-7-chloro-(4H)-4-benzopyranone;
2-(3-methylphenyl)-3-carboxy-6-chloro-(4H)-4-benzopyranone;
2-(3-methylphenyl)-3-carboxy-6-bromo-(4H)-4-benzopyranone;
2-(2-thiophenyl)-3-carboxy-8-methoxy-(4H)-4-benzopyranone;
2-(2-thiophenyl)-3-carboxy-7-methoxy-(4H)-4-benzopyranone;
2-(2-thiophenyl)-3-carboxy-6-methoxy-(4H)-4-benzopyranone;
2-(2-thiophenyl)-3-carboxy-(4H)-4-benzopyranone;
2-(2-thiophenyl)-3-carboxy-8-methyl-(4H)-4-benzopyranone;
2-(2-thiophenyl)-3-carboxy-7-methyl-(4H)-4-benzopyranone;
2-(2-thiophenyl)-3-carboxy-6-methyl-(4H)-4-benzopyranone;
2-(2-thiophenyl)-3-carboxy-7-chloro-(4H)-4-benzopyranone;

2-(2-thiophenyl)-3-carboxy-6-chloro-(4H)-4-benzopyranone;
2-(2-thiophenyl)-3-carboxy-6-bromo-(4H)-4-benzopyranone;
2-(3,4-dimethoxyphenyl)-3-carboxy-(4H)-4-benzopyranone;
2-(3,4-dimethoxyphenyl)-3-carboxy-8-methyl-(4H)-4-benzopyranone;
2-(3,4-dimethoxyphenyl)-3-carboxy-7-methyl-(4H)-4-benzopyranone;
2-(3,4-dimethoxyphenyl)-3-carboxy-6-methyl-(4H)-4-benzopyranone;
2-(3,4-dimethoxyphenyl)-3-carboxy-7-chloro-(4H)-4-benzopyranone;
2-(3,4-dimethoxyphenyl)-3-carboxy-6-chloro-(4H)-4-benzopyranone;
2-(3,4-dimethoxyphenyl)-3-carboxy-6-bromo-(4H)-4-benzopyranone;
2-(3,4-dimethoxyphenyl)-3-carboxy-7-methoxy-(4H)-4-benzopyranone;
2-(3,4-dimethoxyphenyl)-3-carboxy-8-methoxy-(4H)-4-benzopyranone;
2-(3-fluorophenyl)-3-carboxy-(4H)-4-benzopyranone;
2-(3-fluorophenyl)-3-carboxy-8-methyl-(4H)-4-benzopyranone;
2-(3-fluorophenyl)-3-carboxy-7-methyl-(4H)-4-benzopyranone;
2-(3-fluorophenyl)-3-carboxy-6-methyl-(4H)-4-benzopyranone;
2-(3-fluorophenyl)-3-carboxy-7-chloro-(4H)-4-benzopyranone;
2-(3-fluorophenyl)-3-carboxy-6-chloro-(4H)-4-benzopyranone;
2-(3-fluorophenyl)-3-carboxy-6-bromo-(4H)-4-benzopyranone;
2-(3-fluorophenyl)-3-carboxy-7-methoxy-(4H)-4-benzopyranone;
2-(3,5-difluorophenyl)-3-carboxy-(4H)-4-benzopyranone;
2-(3,5-difluorophenyl)-3-carboxy-8-methyl-(4H)-4-benzopyranone;
2-(3,5-difluorophenyl)-3-carboxy-7-methyl-(4H)-4-benzopyranone;
2-(3,5-difluorophenyl)-3-carboxy-6-methyl-(4H)-4-benzopyranone;
2-(3,5-difluorophenyl)-3-carboxy-6-chloro-(4H)-4-benzopyranone;
2-(3,5-difluorophenyl)-3-carboxy-6-bromo-(4H)-4-benzopyranone;
2-(2,3-difluorophenyl)-3-carboxy-8-methyl-(4H)-4-benzopyranone;
2-(2,3-difluorophenyl)-3-carboxy-7-methyl-(4H)-4-benzopyranone;
2-(2,3-difluorophenyl)-3-carboxy-6-methyl-(4H)-4-benzopyranone;
2-(2,3-difluorophenyl)-3-carboxy-7-chloro-(4H)-4-benzopyranone;
2-(2,3-difluorophenyl)-3-carboxy-6-chloro-(4H)-4-benzopyranone;
2-(2,3-difluorophenyl)-3-carboxy-6-bromo-(4H)-4-benzopyranone;
2-(2,5-difluorophenyl)-3-carboxy-8-methyl-(4H)-4-benzopyranone;
2-(2,5-difluorophenyl)-3-carboxy-7-methyl-(4H)-4-benzopyranone;
2-(2,5-difluorophenyl)-3-carboxy-6-methyl-(4H)-4-benzopyranone;
2-(2,5-difluorophenyl)-3-carboxy-7-chloro-(4H)-4-benzopyranone;
2-(2,5-difluorophenyl)-3-carboxy-6-chloro-(4H)-4-benzopyranone;
2-(2,5-difluorophenyl)-3-carboxy-6-bromo-(4H)-4-benzopyranone;
2-(3,4-difluorophenyl)-3-carboxy-8-methyl-(4H)-4-benzopyranone;
2-(3,4-difluorophenyl)-3-carboxy-7-methyl-(4H)-4-benzopyranone;
2-(3,4-difluorophenyl)-3-carboxy-6-methyl-(4H)-4-benzopyranone;
2-(3,4-difluorophenyl)-3-carboxy-6-chloro-(4H)-4-benzopyranone;
2-(4-chlorophenyl)-3-carboxy-8-methyl-(4H)-4-benzopyranone;
2-(4-chlorophenyl)-3-carboxy-7-methyl-(4H)-4-benzopyranone;
2-(4-chlorophenyl)-3-carboxy-6-methyl-(4H)-4-benzopyranone;
2-(4-chlorophenyl)-3-carboxy-6-chloro-(4H)-4-benzopyranone;
2-(4-chlorophenyl)-3-carboxy-6-bromo-(4H)-4-benzopyranone;
2-(4-chlorophenyl)-3-carboxy-(4H)-4-benzopyranone; and
2-(4-chlorophenyl)-3-carboxy-8-methoxy-(4H)-4-benzopyranone.

In this regard, the TNF-related disease may be any one selected from the group consisting of autoimmune diseases, inflammatory diseases, cardiovascular diseases, metabolic diseases, immune disorders, neurological diseases, ophthalmic diseases, skin diseases, psychiatric diseases, infectious diseases, and cancers, but is not limited thereto.

Specifically, the TNF-related disease may be any one selected from the group consisting of rheumatoid arthritis, juvenile rheumatoid arthritis, inflammatory bowel disease, Crohn's disease, ulcerative colitis, psoriasis, plaque psoriasis, juvenile plaque psoriasis, psoriatic arthritis, polyarticular juvenile idiopathic arthritis, Behcet's enteritis, ankylosing spondylitis, axial spondyloarthritis, juvenile enthesitis-related arthritis, polymyalgia rheumatica, multiple sclerosis, thyroiditis, delayed hypersensitivity, allergy, contact dermatitis, atopic dermatitis, systemic lupus erythematosus, systemic sclerosis, adult-onset Still's disease, asthma, autoimmune thyroid disorder, Sjogren's syndrome, Kawasaki disease, pancreatitis, nephritis, hepatitis, pneumonia, chronic obstructive pulmonary disease, otitis media, angioplasia nephritis, myelodysplastic syndrome, osteoarthritis, sarcoidosis, granuloma annulare, Wegener's granulomatosis, lupus, hemolytic uremic syndrome, arteriosclerosis, vasculitis, heart failure, stroke, myocardial infarction, myocardial ischemia-reperfusion injury, sexual dysfunction, obesity, hypertension, diabetes mellitus and diabetic complication, hyperlipidemia, preeclampsia, kidney disease, liver disease, kidney injury, liver injury, snake bite, allograft rejection, organ transplantation, graft versus host disease, dementia, Alzheimer's disease, Parkinson's disease, amyotrophic lateral sclerosis, pain, central nervous system disease, uveitis, Behcet's disease, diabetic macular edema, macular degeneration, orbitopathy, glaucoma, hidradenitis suppurativa, multicentric reticulohistiocytosis, *Pityriasis rubra pilaris*, eosinophilic fasciitis, panniculitis, necrobiosis lipoidica diabeticorum, cicatricial pemphigoid, pyoderma gangrenosum, Sweet's syndrome, subcorneal pustular dermatosis, scleroderma, neutrophilic dermatitis, toxic epidermal necrolysis, pustular dermatitis, dermatomyositis, polymyositis, bullous dermatosis, erythema nodosum, alopecia, depressive disorder, bipolar disorder, anxiety disorder, tuberculosis, viral infection, bacterial infection, fungal infection, protozoan infection, cerebral malaria, sepsis, septic shock, prostate cancer, skin cancer, colorectal cancer, kidney cancer, pancreatic cancer, ovarian cancer, breast cancer, bladder cancer, prostate cancer, lymphoma, glioma, osteosarcoma, leukemia, multiple myeloma, and cachexia, but is not limited thereto.

In one example of the present invention, the composition may further contain a drug, wherein the administration in combination with the drug can more effectively prevent, alleviate, or treat TNF-related diseases.

The "drug" used in the present invention is a substance capable of inducing a desired biological or pharmacological effect by promoting or inhibiting a physiological function in the body of an animal or human, and means a chemical or biological substance or compound suitable to be administered to an animal or human, and may (1) have a prophylactic effect on the organism by the prevention of undesired biological effects such as the prevention of infection, (2) ameliorate the condition caused by the disease, for example, mitigate the pain or infection resulting from the disease, and (3) play a role in mitigating, reducing, or completely eliminating the disease from the organism.

Specifically, the drug may be selected from anti-rheumatic drugs (DMARDs), nonsteroidal anti-inflammatory drugs (NSAIDs), steroids, antimetabolites, anti-inflammatory agents, antibiotics, signaling/enzyme inhibitors, receptor inhibitors, HMGB1 inhibitors, antithrombotic drugs, autophagy agonists, cytokine inhibitors, HMG-CoA reductase inhibitors, antihypertensive agents, anticancer agents, immune activation agents, B cell inhibitors, and T cell inhibitors, but is not limited thereto.

More specifically, the drug may be selected from the group consisting of methotrexate, hydroxychloroquine, sulfasalazine, leflunomide, bucillamine, cyclosporine, tacrolimus, azathioprine, cyclophosphamide, mizoribine, penicillamine, oral gold preparation, antimalarial agent, 6-mercaptopurine, indomethacin, naproxen, sulindac, diclofenac, aceclofenac, mefenamic acid, aspirin, fenoprofen, salsalate, piroxicam, etodolac, flurbiprofen, ibuprofen, loxoprofen, nabumetone, lonazolac, meloxicam, fenbufen, ketorolac tromethamine, indoprofen, ketoprofen, suprofen, carprofen, tiaprofenic acid, flufenamic acid, ebselen, felbinac, tolmetin, flunixin, celecoxib, rofecoxib, hydrocortisone, cortisone, prednisolone, methylprednisolone, triamcinolone, betamethasone, dexamethasone, fludrocortisone, entocort, 5-aminosalicylate, 6-thioguanine, cytarabine, 5-fluorouracil, dacarbazine, mechlorethamine, thiotepa, chlorambucil, melphalan, carmustine, lomustine, busulfan, sestrin 2, withaferin A, celastrol, quercetin, luteolin, curcumin, metformin, dibromomannitol, GR270773, pentoxifylline, N-acetylcysteine, melatonin, resveratrol, mesalamine, single chain fatty acid, glutamine, gemfibrozil, retinoid, hydroxyurea, trihydroxyisoflavone, deoxykaempferol, kaempferol, gingerol, caffeic acid, cyanidin, cryptotanshinone, deguelin, delphinidin, equol, fisetin, myricetin, procyanidin B2, metronidazole, ciprofloxacin, niclosamide, thiabendazole, imipenem-cilastatin, fluoroquinolone, tofacitinib, glyburide, rolipram, doxycycline, VX-166, zVAD, L-97-1, ISO-1, tauroursodeoxycholic acid, HK-156, A-285222, CP-0127, Bis-N-norgliovictin, aurintricarboxylic acid, chloroamidine, ouabain, terazosin, prazosin, tranilast, apremilast, monobenzone, phenazopyridine, 546C88, NOX-100, gabexate mesilate, ulinastatin, somatostatin, octreotide, IKK inhibitor, caspase inhibitor, TAK-242, eritoran, ki16425, camptothecin, caffeic acid phenethyl ester, sulforaphane, Tim-3, BN-52021, BB-882, TCV-309, CT-400, ethyl pyruvate, hemin, CORM-2, tanshinone IIA sulfonate, nicotine, EGCG, isorhamnetin-3-O-galactoside, persicarin, catechin, carbenoxolone, glycyrrhizin, emodin-6-O-b-D-glucoside, acteoside, forsythoside B, rosmarinic acid, chlorogenic acid, inflachromene, cilostazol, clopidogrel, sarpogrelate, drotrecogin alpha, carbamazepine, chloroquine, anakinra, tocilizumab, LMT-28, 1-(3-dimethylaminopropyl)-3-ethylurea, gp130Fc, beta-arrestin 2, IL-30, diacerein, secukinumab, ustekinumab, ixekizumab, thalidomide, adalimumab, infliximab, pravastatin, atorvastatin, rosuvastatin, simvastatin, losartan, telmisartan, hydrochlorothiazide, furosemide, propranolol, metoprolol, captopril, amlodipine, clonidine, methyldopa, minoxidil, streptozotocin, mitomycin, cisplatin, daunorubicin, doxorubicin, dactinomycin, bleomycin, mithramycin, anthramycin, calicheamicin, duocarmycin, vincristine, taxol, docetaxel, cytochalasin B, gramicidin D, ethidium bromide, emetine, mitomycin, etoposide, teniposide, vinblastine, colchicine, dihydroxy anthracenedione, mitoxantrone, mithramycin, actinomycin D, 1-dehydrotestosterone, procaine, tetracaine, lidocaine, propranolol, tamoxifen, bazedoxifene, puromycin, anetholtrithion, nivolumab, pembrolizumab, ipilimumab, atezolizumab, alpha-galactosylceramide, SRT3025, DTA-1, IL-7, IL-2, IL-15, CXCL1, ATRA, gemcitabine, carboplatin, NCX-4016, CDDO-Me, sunitinib, zoledronic acid, Astragalus polysaccharide, rituximab, imuran, abatacept, GW9662, rosiglitazone, Y-27632, and alefacept, but is not limited thereto.

The composition may contain from 0.0001% by weight to 10% by weight, based on the total weight of the composition, of a 4-benzopyranone derivative, a pharmaceutically acceptable salt, solvate, racemate, or stereoisomer thereof, preferably 0.001% by weight to 1% by weight, but not limited thereto.

In one embodiment of the present invention, the pharmaceutical composition for preventing or treating TNF-related diseases, containing the 4-benzopyranone derivative, pharmaceutically acceptable salt, solvate, racemate, or stereoisomer thereof as an active ingredient may be used in the form of any one of the formulations selected from the group consisting of injections, granules, powders, tablets, pills, capsules, suppositories, gels, suspensions, emulsions, drops, or solutions according to a customary method.

In another embodiment of the present invention, the pharmaceutical composition may further contain one or more additives selected from the group consisting of carriers, excipients, disintegrating agents, sweetening agents, coating agents, bulking agents, glidants, flavoring agents, antioxidants, buffers, bacteriostatic agents, diluents, dispersing agents, surfactants, binders, and lubricants, which are appropriate to be customarily used in the preparation of the pharmaceutical composition.

Specifically, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used as the carrier, excipient, and diluent. Solid preparations for oral administration include tablets, pills, powders, granules, capsules and the like. These solid preparations may be prepared by mixing at least one or more excipients, for example, starch, calcium carbonate, sucrose or lactose, gelatin and the like into the composition. In addition to simple excipients, lubricants such as magnesium stearate, talc may be also used. Liquid preparations for oral administration include suspensions, solutions for internal use, emulsions, syrups and the like, and may comprise various excipients, for example wetting agents, sweetening agent, perfuming agents, preservatives and the like, in addition to water and liquid paraffin which are commonly used simple diluents. Preparations for parenteral administration include sterilized aqueous solutions, non-aqueous solutions, suspensions, emulsions, lyophilized preparations, suppositories and the like. As non-aqueous solvents or suspending agents, propylene glycol, polyethylene glycol, vegetable oil such as olive oil, injectable ester such as ethyl oleate and the like may be used. As the base of the suppositories, witepsol, Macrogol, Tween 61, cacao butter, laurin butter, glycerogelatin and the like may be used.

The preferred dosage of the 4-benzopyranone derivative, pharmaceutically acceptable salt, solvate, racemate, or stereoisomer thereof may vary depending on the condition and body weight of the subject, the kind and severity of the disease, the form of the drug, administration route, and the duration, and may be appropriately selected by those skilled in the art. However, for the preferred effect, the compound of the present invention may be administered in a daily dosage of 0.0001 to 100 mg/kg, preferably 0.001 to 100 mg/kg. The dose may be administered once per day or in several divided doses per day, and the scope of the present invention is not limited thereto.

In one embodiment of the present invention, the pharmaceutical composition may be administered to a mammal such as a rat, a mouse, a livestock, a human and the like in a variety of routes. All modes of administration may be expected, and the pharmaceutical composition may be administered, for example, by oral, rectal or intravenous, intramuscular, subcutaneous, intrauterine, intrathecal, or intracerebroventricular injections.

In one embodiment of the present invention, the health functional food composition may contain various nutrients, vitamins, minerals (electrolytes), flavors such as synthetic flavors and natural flavors, coloring agents and improving agents (cheese, chocolate and the like), pectic acid and salts thereof, alginic acid and salts thereof, organic acids, protective colloidal thickening agents, pH adjusting agents, stabilizing agents, preservatives, glycerin, alcohols, carbonizing agents as used in carbonated beverages and the like. Additionally, the health functional food composition may contain fruit flesh for the preparation of natural fruit juices, synthetic fruit juices, and vegetable beverages. These components may be used independently or in combination. In addition, the health functional food composition may be in the form of any one of meats, sausages, bread, chocolate, candies, snacks, confectionery, pizza, ramen, gum, ice cream, soups, beverages, teas, functional water, drinks, alcoholic beverages, and multi-vitamin preparations.

In addition, the health functional food composition may further comprise a food additive, and the suitability of the additive as a "food additive" is determined based on a standard and criteria relating to the concerned item according to general rules and general test methods and the like of the Korean Food Additives Code that has been approved by the Ministry of Food and Drug Safety as long as other rules are not provided.

The items disclosed in the "Korean Food Additives Code" include, for example, a chemically synthetic product, such as ketone, glycine, calcium citrate, nicotinic acid, cinnamic acid and the like, a natural additive product, such as persimmon color, a licorice extract, microcrystalline cellulose, Kaoliang color, guar gum and the like, and mixed preparations, such as a sodium L-glutamate preparation, an alkali agent for noodles, a preservative preparation, a tar color preparation and the like.

In this regard, the content of the 4-benzopyranone derivative, pharmaceutically acceptable salt, solvate, racemate, or stereoisomer thereof which is added to foods during the preparation of the health functional food composition may be appropriately increased or decreased, if necessary, and may be added to be included preferably in an amount of 1% by weight to 90% by weight.

Furthermore, the present invention provides a method for treating TNF-related diseases, comprising a step of treating with a 4-benzopyranone derivative represented by Formula 1, a pharmaceutically acceptable salt, solvate, racemate, or stereoisomer thereof in a pharmaceutically effective amount:

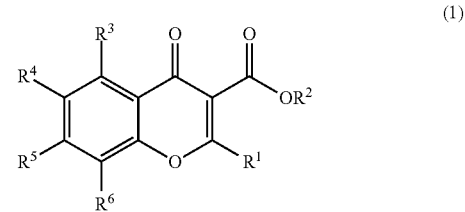

(1)

in which, $R^1$ is heteroaryl or substituted phenyl;

$R^2$ is hydrogen or lower alkyl of (C1-C4); and $R^3$, $R^4$, $R^5$, and $R^6$ are each independently hydrogen, halogen, or (C1-C4)alkoxy.

Specifically, in Formula 1 above, $R^1$ may be furanyl, thiophenyl, or substituted phenyl represented by

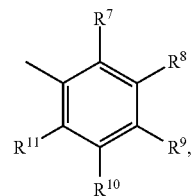

and $R^3$, $R^4$, $R^5$, $R^6$, $R^7$, $R^8$, $R^9$, $R^{10}$, and $R^{11}$ may be each independently hydrogen, chloro, bromo, fluoro, or methoxy.

More specifically, the 4-benzopyranone derivative may be selected from the group consisting of 2-(2-chlorophenyl)-3-carboxy-7-methoxy-(4H)-4-benzopyranone;

2-(2-chlorophenyl)-3-carboxy-(4H)-4-benzopyranone;

2-(2-furanyl)-3-carboxy-(4H)-4-benzopyranone;

2-(2-furanyl)-3-carboxy-8-methoxy-(4H)-4-benzopyranone;

2-(2-furanyl)-3-carboxy-7-methoxy-(4H)-4-benzopyranone;

2-(2-furanyl)-3-carboxy-6-methoxy-(4H)-4-benzopyranone;

2-(2-furanyl)-3-carboxy-8-methyl-(4H)-4-benzopyranone;

2-(2-furanyl)-3-carboxy-7-methyl-(4H)-4-benzopyranone;

2-(2-furanyl)-3-carboxy-6-methyl-(4H)-4-benzopyranone;

2-(2-furanyl)-3-carboxy-7-chloro-(4H)-4-benzopyranone;

2-(2-furanyl)-3-carboxy-6-chloro-(4H)-4-benzopyranone;

2-(2-furanyl)-3-carboxy-6-bromo-(4H)-4-benzopyranone;

2-(3-methylphenyl)-3-carboxy-(4H)-4-benzopyranone;

2-(3-methylphenyl)-3-carboxy-8-methoxy-(4H)-4-benzopyranone;
2-(3-methylphenyl)-3-carboxy-7-methoxy-(4H)-4-benzopyranone;
2-(3-methylphenyl)-3-carboxy-6-methoxy-(4H)-4-benzopyranone;
2-(3-methylphenyl)-3-carboxy-8-methyl-(4H)-4-benzopyranone;
2-(3-methylphenyl)-3-carboxy-7-methyl-(4H)-4-benzopyranone;
2-(3-methylphenyl)-3-carboxy-6-methyl-(4H)-4-benzopyranone;
2-(3-methylphenyl)-3-carboxy-7-chloro-(4H)-4-benzopyranone;
2-(3-methylphenyl)-3-carboxy-6-chloro-(4H)-4-benzopyranone;
2-(3-methylphenyl)-3-carboxy-6-bromo-(4H)-4-benzopyranone;
2-(2-thiophenyl)-3-carboxy-8-methoxy-(4H)-4-benzopyranone;
2-(2-thiophenyl)-3-carboxy-7-methoxy-(4H)-4-benzopyranone;
2-(2-thiophenyl)-3-carboxy-6-methoxy-(4H)-4-benzopyranone;
2-(2-thiophenyl)-3-carboxy-(4H)-4-benzopyranone;
2-(2-thiophenyl)-3-carboxy-8-methyl-(4H)-4-benzopyranone;
2-(2-thiophenyl)-3-carboxy-7-methyl-(4H)-4-benzopyranone;
2-(2-thiophenyl)-3-carboxy-6-methyl-(4H)-4-benzopyranone;
2-(2-thiophenyl)-3-carboxy-7-chloro-(4H)-4-benzopyranone;
2-(2-thiophenyl)-3-carboxy-6-chloro-(4H)-4-benzopyranone;
2-(2-thiophenyl)-3-carboxy-6-bromo-(4H)-4-benzopyranone;
2-(3,4-dimethoxyphenyl)-3-carboxy-(4H)-4-benzopyranone;
2-(3,4-dimethoxyphenyl)-3-carboxy-8-methyl-(4H)-4-benzopyranone;
2-(3,4-dimethoxyphenyl)-3-carboxy-7-methyl-(4H)-4-benzopyranone;
2-(3,4-dimethoxyphenyl)-3-carboxy-6-methyl-(4H)-4-benzopyranone;
2-(3,4-dimethoxyphenyl)-3-carboxy-7-chloro-(4H)-4-benzopyranone;
2-(3,4-dimethoxyphenyl)-3-carboxy-6-chloro-(4H)-4-benzopyranone;
2-(3,4-dimethoxyphenyl)-3-carboxy-6-bromo-(4H)-4-benzopyranone;
2-(3,4-dimethoxyphenyl)-3-carboxy-7-methoxy-(4H)-4-benzopyranone;
2-(3,4-dimethoxyphenyl)-3-carboxy-8-methoxy-(4H)-4-benzopyranone;
2-(3-fluorophenyl)-3-carboxy-(4H)-4-benzopyranone;
2-(3-fluorophenyl)-3-carboxy-8-methyl-(4H)-4-benzopyranone;
2-(3-fluorophenyl)-3-carboxy-7-methyl-(4H)-4-benzopyranone;
2-(3-fluorophenyl)-3-carboxy-6-methyl-(4H)-4-benzopyranone;
2-(3-fluorophenyl)-3-carboxy-7-chloro-(4H)-4-benzopyranone;
2-(3-fluorophenyl)-3-carboxy-6-chloro-(4H)-4-benzopyranone;
2-(3-fluorophenyl)-3-carboxy-6-bromo-(4H)-4-benzopyranone;
2-(3-fluorophenyl)-3-carboxy-7-methoxy-(4H)-4-benzopyranone;
2-(3,5-difluorophenyl)-3-carboxy-(4H)-4-benzopyranone;
2-(3,5-difluorophenyl)-3-carboxy-8-methyl-(4H)-4-benzopyranone;
2-(3,5-difluorophenyl)-3-carboxy-7-methyl-(4H)-4-benzopyranone;
2-(3,5-difluorophenyl)-3-carboxy-6-methyl-(4H)-4-benzopyranone;
2-(3,5-difluorophenyl)-3-carboxy-6-chloro-(4H)-4-benzopyranone;
2-(3,5-difluorophenyl)-3-carboxy-6-bromo-(4H)-4-benzopyranone;
2-(2,3-difluorophenyl)-3-carboxy-8-methyl-(4H)-4-benzopyranone;
2-(2,3-difluorophenyl)-3-carboxy-7-methyl-(4H)-4-benzopyranone;
2-(2,3-difluorophenyl)-3-carboxy-6-methyl-(4H)-4-benzopyranone;
2-(2,3-difluorophenyl)-3-carboxy-7-chloro-(4H)-4-benzopyranone;
2-(2,3-difluorophenyl)-3-carboxy-6-chloro-(4H)-4-benzopyranone;
2-(2,3-difluorophenyl)-3-carboxy-6-bromo-(4H)-4-benzopyranone;
2-(2,5-difluorophenyl)-3-carboxy-8-methyl-(4H)-4-benzopyranone;
2-(2,5-difluorophenyl)-3-carboxy-7-methyl-(4H)-4-benzopyranone;
2-(2,5-difluorophenyl)-3-carboxy-6-methyl-(4H)-4-benzopyranone;
2-(2,5-difluorophenyl)-3-carboxy-7-chloro-(4H)-4-benzopyranone;
2-(2,5-difluorophenyl)-3-carboxy-6-chloro-(4H)-4-benzopyranone;
2-(2,5-difluorophenyl)-3-carboxy-6-bromo-(4H)-4-benzopyranone;
2-(3,4-difluorophenyl)-3-carboxy-8-methyl-(4H)-4-benzopyranone;
2-(3,4-difluorophenyl)-3-carboxy-7-methyl-(4H)-4-benzopyranone;
2-(3,4-difluorophenyl)-3-carboxy-6-methyl-(4H)-4-benzopyranone;
2-(3,4-difluorophenyl)-3-carboxy-6-chloro-(4H)-4-benzopyranone;
2-(4-chlorophenyl)-3-carboxy-8-methyl-(4H)-4-benzopyranone;
2-(4-chlorophenyl)-3-carboxy-7-methyl-(4H)-4-benzopyranone;
2-(4-chlorophenyl)-3-carboxy-6-methyl-(4H)-4-benzopyranone;
2-(4-chlorophenyl)-3-carboxy-6-chloro-(4H)-4-benzopyranone;
2-(4-chlorophenyl)-3-carboxy-6-bromo-(4H)-4-benzopyranone;
2-(4-chlorophenyl)-3-carboxy-(4H)-4-benzopyranone; and
2-(4-chlorophenyl)-3-carboxy-8-methoxy-(4H)-4-benzopyranone.

In this regard, the TNF-related disease may be any one selected from the group consisting of autoimmune diseases, inflammatory diseases, cardiovascular diseases, metabolic diseases, immune disorders, neurological diseases, ophthalmic diseases, skin diseases, psychiatric diseases, infectious diseases, and cancers, but is not limited thereto.

Specifically, the TNF-related disease may be any one selected from the group consisting of rheumatoid arthritis, juvenile rheumatoid arthritis, inflammatory bowel disease, Crohn's disease, ulcerative colitis, psoriasis, plaque psoriasis, juvenile plaque psoriasis, psoriatic arthritis, polyarticular juvenile idiopathic arthritis, Behcet's enteritis, ankylosing spondylitis, axial spondyloarthritis, juvenile enthesitis-related arthritis, polymyalgia rheumatica, multiple sclerosis, thyroiditis, delayed hypersensitivity, allergy, contact dermatitis, atopic dermatitis, systemic lupus erythematosus, systemic sclerosis, adult-onset Still's disease, asthma, autoimmune thyroid disorder, Sjogren's syndrome, Kawasaki disease, pancreatitis, nephritis, hepatitis, pneumonia, chronic obstructive pulmonary disease, otitis media, angioplasia nephritis, myelodysplastic syndrome, osteoarthritis, sarcoidosis, granuloma annulare, Wegener's granulomatosis, lupus, hemolytic uremic syndrome, arteriosclerosis, vasculitis, heart failure, stroke, myocardial infarction, myocardial ischemia-reperfusion injury, sexual dysfunction, obesity, hypertension, diabetes mellitus and diabetic complication, hyperlipidemia, preeclampsia, kidney disease, liver disease, kidney injury, liver injury, snake bite, allograft rejection, organ transplantation, graft versus host disease, dementia, Alzheimer's disease, Parkinson's disease, amyotrophic lateral sclerosis, pain, central nervous system disease, uveitis, Behcet's disease, diabetic macular edema, macular degeneration, orbitopathy, glaucoma, hidradenitis suppurativa, multicentric reticulohistiocytosis, *pityriasis rubra* pilaris, eosinophilic fasciitis, panniculitis, necrobiosis lipoidica diabeticorum, cicatricial pemphigoid, pyoderma gangrenosum, Sweet's syndrome, subcorneal pustular dermatosis, scleroderma, neutrophilic dermatitis, toxic epidermal necrolysis, pustular dermatitis, dermatomyositis, polymyositis, bullous dermatosis, erythema nodosum, alopecia, depressive disorder, bipolar disorder, anxiety disorder, tuberculosis, viral infection, bacterial infection, fungal infection, protozoan infection, cerebral malaria, sepsis, septic shock, prostate cancer, skin cancer, colorectal cancer, kidney cancer, pancreatic cancer, ovarian cancer, breast cancer, bladder cancer, prostate cancer, lymphoma, glioma, osteosarcoma, leukemia, multiple myeloma, and cachexia, but is not limited thereto.

As used herein, the term "pharmaceutically effective amount" refers to an amount sufficient for a drug to be administered to an animal or a human to exhibit the desired physiological or pharmacological activity. However, the pharmaceutically effective amount may be appropriately changed depending on the age, body weight, health condition, and sex of the subject to be administered, administration routes, and the duration of treatment and the like.

In addition, as used herein, the term "pharmaceutically acceptable" refers to being physiologically acceptable and does not customarily cause an allergic reaction such as gastrointestinal disorder, dizziness and the like or a reaction similar thereto when administered to a human. Examples of the carrier, excipient, and diluent include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, and mineral oil. In addition, it may further comprise a filler, an anticoagulant, a lubricant, a wetting agent, a flavoring agent, an emulsifying agent, and a preservative and the like.

In addition, the present invention provides a reagent composition for inhibiting a TNF activity in vitro, containing a 4-benzopyranone derivative represented by Formula 1, a pharmaceutically acceptable salt, solvate, racemate, or stereoisomer thereof as an active ingredient:

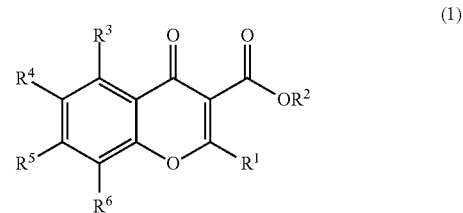

(1)

in which,
$R^1$ is heteroaryl or substituted phenyl;
$R^2$ is hydrogen or lower alkyl of (C1-C4); and
$R^3$, $R^4$, $R^5$, and $R^6$ are each independently hydrogen, halogen, or (C1-C4)alkoxy.

Furthermore, the present invention provides a method for inhibiting a TNF activity, comprising a step of treating an animal excluding a human with a 4-benzopyranone derivative represented by Formula 1 above, a pharmaceutically acceptable salt, solvate, racemate, or stereoisomer thereof.

Specifically, in Formula 1 above, $R^1$ may be furanyl, thiophenyl, or substituted phenyl represented by

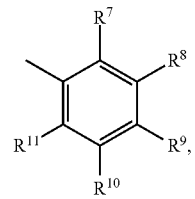

and $R^3$, $R^4$, $R^5$, $R^6$, $R^7$, $R^8$, $R^9$, $R^{10}$, and $R^{11}$ may be each independently hydrogen, chloro, bromo, fluoro, or methoxy.

More specifically, the 4-benzopyranone derivative may be selected from the group consisting of 2-(2-chlorophenyl)-3-carboxy-7-methoxy-(4H)-4-benzopyranone;
2-(2-chlorophenyl)-3-carboxy-(4H)-4-benzopyranone;
2-(2-furanyl)-3-carboxy-(4H)-4-benzopyranone;
2-(2-furanyl)-3-carboxy-8-methoxy-(4H)-4-benzopyranone;
2-(2-furanyl)-3-carboxy-7-methoxy-(4H)-4-benzopyranone;
2-(2-furanyl)-3-carboxy-6-methoxy-(4H)-4-benzopyranone;
2-(2-furanyl)-3-carboxy-8-methyl-(4H)-4-benzopyranone;
2-(2-furanyl)-3-carboxy-7-methyl-(4H)-4-benzopyranone;
2-(2-furanyl)-3-carboxy-6-methyl-(4H)-4-benzopyranone;
2-(2-furanyl)-3-carboxy-7-chloro-(4H)-4-benzopyranone;
2-(2-furanyl)-3-carboxy-6-chloro-(4H)-4-benzopyranone;
2-(2-furanyl)-3-carboxy-6-bromo-(4H)-4-benzopyranone;
2-(3-methylphenyl)-3-carboxy-(4H)-4-benzopyranone;
2-(3-methylphenyl)-3-carboxy-8-methoxy-(4H)-4-benzopyranone;
2-(3-methylphenyl)-3-carboxy-7-methoxy-(4H)-4-benzopyranone;
2-(3-methylphenyl)-3-carboxy-6-methoxy-(4H)-4-benzopyranone;
2-(3-methylphenyl)-3-carboxy-8-methyl-(4H)-4-benzopyranone;

2-(3-methylphenyl)-3-carboxy-7-methyl-(4H)-4-benzopyranone;
2-(3-methylphenyl)-3-carboxy-6-methyl-(4H)-4-benzopyranone;
2-(3-methylphenyl)-3-carboxy-7-chloro-(4H)-4-benzopyranone;
2-(3-methylphenyl)-3-carboxy-6-chloro-(4H)-4-benzopyranone;
2-(3-methylphenyl)-3-carboxy-6-bromo-(4H)-4-benzopyranone;
2-(2-thiophenyl)-3-carboxy-8-methoxy-(4H)-4-benzopyranone;
2-(2-thiophenyl)-3-carboxy-7-methoxy-(4H)-4-benzopyranone;
2-(2-thiophenyl)-3-carboxy-6-methoxy-(4H)-4-benzopyranone;
2-(2-thiophenyl)-3-carboxy-(4H)-4-benzopyranone;
2-(2-thiophenyl)-3-carboxy-8-methyl-(4H)-4-benzopyranone;
2-(2-thiophenyl)-3-carboxy-7-methyl-(4H)-4-benzopyranone;
2-(2-thiophenyl)-3-carboxy-6-methyl-(4H)-4-benzopyranone;
2-(2-thiophenyl)-3-carboxy-7-chloro-(4H)-4-benzopyranone;
2-(2-thiophenyl)-3-carboxy-6-chloro-(4H)-4-benzopyranone;
2-(2-thiophenyl)-3-carboxy-6-bromo-(4H)-4-benzopyranone;
2-(3,4-dimethoxyphenyl)-3-carboxy-(4H)-4-benzopyranone;
2-(3,4-dimethoxyphenyl)-3-carboxy-8-methyl-(4H)-4-benzopyranone;
2-(3,4-dimethoxyphenyl)-3-carboxy-7-methyl-(4H)-4-benzopyranone;
2-(3,4-dimethoxyphenyl)-3-carboxy-6-methyl-(4H)-4-benzopyranone;
2-(3,4-dimethoxyphenyl)-3-carboxy-7-chloro-(4H)-4-benzopyranone;
2-(3,4-dimethoxyphenyl)-3-carboxy-6-chloro-(4H)-4-benzopyranone;
2-(3,4-dimethoxyphenyl)-3-carboxy-6-bromo-(4H)-4-benzopyranone;
2-(3,4-dimethoxyphenyl)-3-carboxy-7-methoxy-(4H)-4-benzopyranone;
2-(3,4-dimethoxyphenyl)-3-carboxy-8-methoxy-(4H)-4-benzopyranone;
2-(3-fluorophenyl)-3-carboxy-(4H)-4-benzopyranone;
2-(3-fluorophenyl)-3-carboxy-8-methyl-(4H)-4-benzopyranone;
2-(3-fluorophenyl)-3-carboxy-7-methyl-(4H)-4-benzopyranone;
2-(3-fluorophenyl)-3-carboxy-6-methyl-(4H)-4-benzopyranone;
2-(3-fluorophenyl)-3-carboxy-7-chloro-(4H)-4-benzopyranone;
2-(3-fluorophenyl)-3-carboxy-6-chloro-(4H)-4-benzopyranone;
2-(3-fluorophenyl)-3-carboxy-6-bromo-(4H)-4-benzopyranone;
2-(3-fluorophenyl)-3-carboxy-7-methoxy-(4H)-4-benzopyranone;
2-(3,5-difluorophenyl)-3-carboxy-(4H)-4-benzopyranone;
2-(3,5-difluorophenyl)-3-carboxy-8-methyl-(4H)-4-benzopyranone;
2-(3,5-difluorophenyl)-3-carboxy-7-methyl-(4H)-4-benzopyranone;
2-(3,5-difluorophenyl)-3-carboxy-6-methyl-(4H)-4-benzopyranone;
2-(3,5-difluorophenyl)-3-carboxy-6-chloro-(4H)-4-benzopyranone;
2-(3,5-difluorophenyl)-3-carboxy-6-bromo-(4H)-4-benzopyranone;
2-(2,3-difluorophenyl)-3-carboxy-8-methyl-(4H)-4-benzopyranone;
2-(2,3-difluorophenyl)-3-carboxy-7-methyl-(4H)-4-benzopyranone;
2-(2,3-difluorophenyl)-3-carboxy-6-methyl-(4H)-4-benzopyranone;
2-(2,3-difluorophenyl)-3-carboxy-7-chloro-(4H)-4-benzopyranone;
2-(2,3-difluorophenyl)-3-carboxy-6-chloro-(4H)-4-benzopyranone;
2-(2,3-difluorophenyl)-3-carboxy-6-bromo-(4H)-4-benzopyranone;
2-(2,5-difluorophenyl)-3-carboxy-8-methyl-(4H)-4-benzopyranone;
2-(2,5-difluorophenyl)-3-carboxy-7-methyl-(4H)-4-benzopyranone;
2-(2,5-difluorophenyl)-3-carboxy-6-methyl-(4H)-4-benzopyranone;
2-(2,5-difluorophenyl)-3-carboxy-7-chloro-(4H)-4-benzopyranone;
2-(2,5-difluorophenyl)-3-carboxy-6-chloro-(4H)-4-benzopyranone;
2-(2,5-difluorophenyl)-3-carboxy-6-bromo-(4H)-4-benzopyranone;
2-(3,4-difluorophenyl)-3-carboxy-8-methyl-(4H)-4-benzopyranone;
2-(3,4-difluorophenyl)-3-carboxy-7-methyl-(4H)-4-benzopyranone;
2-(3,4-difluorophenyl)-3-carboxy-6-methyl-(4H)-4-benzopyranone;
2-(3,4-difluorophenyl)-3-carboxy-6-chloro-(4H)-4-benzopyranone;
2-(4-chlorophenyl)-3-carboxy-8-methyl-(4H)-4-benzopyranone;
2-(4-chlorophenyl)-3-carboxy-7-methyl-(4H)-4-benzopyranone;
2-(4-chlorophenyl)-3-carboxy-6-methyl-(4H)-4-benzopyranone;
2-(4-chlorophenyl)-3-carboxy-6-chloro-(4H)-4-benzopyranone;
2-(4-chlorophenyl)-3-carboxy-6-bromo-(4H)-4-benzopyranone;
2-(4-chlorophenyl)-3-carboxy-(4H)-4-benzopyranone; and
2-(4-chlorophenyl)-3-carboxy-8-methoxy-(4H)-4-benzopyranone.

EMBODIMENT FOR WORKING THE INVENTION

Hereinafter, the present invention will be described in more detail through the working examples in order to promote understanding of the present invention. However, the following examples are provided for a better understanding of the present invention to one of ordinary skill in the art, and are only illustrations of the present invention, but the scope of the present invention is not limited to the following examples.

<Preparation Example 1> General Reaction Process of 4-benzoypyranone Compound Derivative

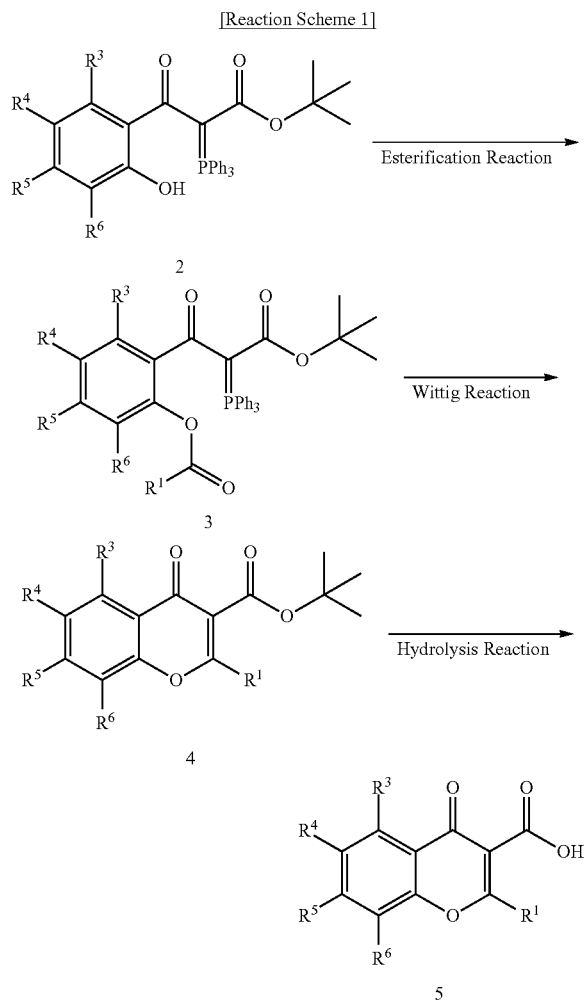

First, a 2-hydroxybenzophosphorane derivative compound (2) was dissolved in carbon dichloride, and pyridine (2 eq) was added dropwise thereto. Then, a heteroaromatic or benzoyl chloride derivative (1.5 eq) was added dropwise, and 4-dimethylaminopyridine (0.05 eq) was added dropwise thereto. Then, the reaction was stirred under a nitrogen atmosphere for 1 hour to 5 hours. When the reaction was completed, acetic acid (1 mL) was added to the reaction solution, and Girard's reagent T (1 eq) was added dropwise, and then the mixture was stirred under a nitrogen atmosphere for 1 hour. The mixture was extracted with 1N HCl and saturated $NaHCO_3$ solution. The organic layer was dried over anhydrous $MgSO_4$, and then filtered and distilled under reduced pressure to obtain the compound (3). The compound (3) was dissolved in a solvent toluene. After refluxing with heating under a nitrogen atmosphere for 5 to 18 hours, when the reaction was completed, the solvent was removed by distillation under reduced pressure, and then the reaction was purified by chromatography. The thus obtained 4-benzopyranone compound (4) was dissolved in carbon dichloride, and TFA was added dropwise, and the mixture was stirred under a nitrogen atmosphere for 1 hour to 5 hours. When the reaction was completed, the solvent was removed by distillation under reduced pressure. The crystals obtained by crystallization with ether were filtered and then dried in a vacuum oven to obtain the final desired compounds (5).

<Example 1> Synthesis of 2-(3-fluorophenyl)-3-carboxy-7-methoxy-(4H)-4-benzopyranone Through the general synthesis method of Preparation Example 1 above, a 2-hydroxy-4-methoxybenzophosphorane compound (150 mg, 0.28 mmol), pyridine (0.05 mL, 0.57 mmol, 2 eq), and 3-fluorobenzoyl chloride (0.05 mL, 0.43 mmol, 1.5 eq) were stirred in carbon dichloride (5 mL) for 4 hours and 30 minutes, and stirred in toluene (10 mL) for 2 hours and 30 minutes, and then stirred in TFA (2 mL) and carbon dichloride (2 mL) for 1 hour and 30 minutes to obtain 60 mg (67.0%) of the final desired compound, 2-(3-fluorophenyl)-3-carboxy-7-methoxy-(4H)-4-benzopyranone.

m.p. 214-215° C. $^1$H NMR (300 MHz, $CDCl_3$): δ 3.96 (s, 3H), 6.97 (d, J=2.3 Hz, 1H), 7.15 (dd, J=9.1, 2.3 Hz, 1H), 7.26-7.50 (m, 4H), 8.24 (d, J=9.1 Hz, 1H); $^{13}$C NMR (75 MHz, $CDCl_3$): δ 56.22, 100.21, 110.10, 115.48, 116.14, 116.91, 118.53, 124.96, 127.77, 129.86, 134.56, 157.54, 160.45, 163.56, 166.12, 172.04, 179.62.

<Example 2> Synthesis of 2-(2-furanyl)-3-carboxy-8-methoxy-(4H)-4-benzopyranone

Through the general synthesis method of Preparation Example 1 above, a 2-hydroxy-3-methoxybenzophosphorane compound (100 mg, 0.20 mmol), diisopropylethylamine (0.068 mL, 0.40 mmol, 2 eq), 2-furoyl chloride (0.029 mL, 0.30 mmol, 1.5 eq), and 4-(dimethylamino)pyridine (5 mg) were stirred in methylene chloride (3 mL) for 2 hours, and stirred in toluene (6 mL) for 50 hours, and then stirred in TFA (3 mL) and methylene chloride (3 mL) for 1 hour to obtain 25.2 mg (47.6%) of the final desired compound, 2-(2-furanyl)-3-carboxy-8-methoxy-(4H)-4-benzopyranone.

m.p. 195-197° C. $^1$H NMR (300 MHz, $CDCl_3$): δ 2.53 (s, 3H), 6.71 (dd, J=3.7, 1.7 Hz, 1H), 7.55 (d, J=8.6 Hz, 1H), 7.66 (dd, J=8.6, 2.0 Hz, 1H), 7.79 (d, J=1.7 Hz, 1H), 7.99 (d, J=3.7 Hz, 1H), 8.09 (s, 1H), 14.55 (s, 1H).

<Example 3> Synthesis of 2-(2-furanyl)-3-carboxy-7-methoxy-(4H)-4-benzopyranone

Through the general synthesis method of Preparation Example 1 above, a 2-hydroxy-4-methoxybenzophosphorane compound (200 mg, 0.38 mmol), pyridine (0.06 mL, 0.76 mmol, 2 eq), and 2-furoyl chloride (0.05 mL, 0.57 mmol, 1.5 eq) were stirred in carbon dichloride (4 mL) for 1 hour, and stirred in toluene (15 mL) for 10 hours, and then stirred in TFA (2 mL) and carbon dichloride (2 mL) for 4 hours to obtain 50 mg (46.0%) of the final desired compound, 2-(2-furanyl)-3-carboxy-7-methoxy-(4H)-4-benzopyranone.

m.p. 217-219° C. $^1$H NMR (300 MHz, $CDCl_3$): δ 3.99 (s, 3H), 6.71 (dd, J=3.7, 1.6 Hz, 1H), 7.03 (d, J=2.3 Hz, 1H), 7.11 (dd, J=9.0, 2.3 Hz, 1H), 7.78 (d, J=1.6 Hz, 1H), 8.01 (d, J=3.7 Hz, 1H), 8.21 (d, J=9.0 Hz, 1H), 15.00 (s, 1H).

<Example 4> Synthesis of 2-(2-furanyl)-3-carboxy-6-methoxy-(4H)-4-benzopyranone

Through the general synthesis method of Preparation Example 1 above, a 2-hydroxy-5-methoxybenzophosphorane compound (200 mg, 0.38 mmol), pyridine (0.06 mL, 0.76 mmol, 2 eq), and 2-furoyl chloride (0.05 mL, 0.57 mmol, 1.5 eq) were stirred in methylene chloride (4 mL) for 1 hour, and stirred in toluene (15 mL) for 10 hours, and then stirred in TFA (2 mL) and methylene chloride (2 mL) for 4 hours to obtain 70 mg (64.0%) of the final desired compound, 2-(2-furanyl)-3-carboxy-6-methoxy-(4H)-4-benzopyranone.

m.p. 205-207° C. $^1$H NMR (300 MHz, CDCl$_3$): δ 3.97 (s, 3H), 6.71 (dd, J=3.7, 1.7 Hz, 1H), 7.43 (dd, J=9.2, 3.1 Hz, 1H), 7.60 (d, J=9.2 Hz, 1H), 7.64 (d, J=3.1 Hz, 1H), 7.79 (d, J=1.7 Hz, 1H), 7.99 (d, J=3.7 Hz, 1H), 14.60 (s, 1H).

<Example 5> Synthesis of 2-(3-methylphenyl)-3-carboxy-8-methoxy-(4H)-4-benzopyranone Through the general synthesis method of Preparation Example 1 above, a 2-hydroxy-3-methoxybenzophosphorane compound (100 mg, 0.20 mmol), diisopropylethylamine (0.068 mL, 0.40 mmol, 2 eq), m-toluoyl chloride (0.031 mL, 0.24 mmol, 1.2 eq), and 4-(dimethylamino)pyridine (5 mg) were stirred in methylene chloride (3 mL) for 24 hours, and stirred in toluene (6 mL) for 14 hours, and then stirred in TFA (3 mL) and methylene chloride (3 mL) for 1 hour and 30 minutes to obtain 23.1 mg (40.1%) of the final desired compound, 2-(3-methylphenyl)-3-carboxy-8-methoxy-(4H)-4-benzopyranone.

m.p. 192-195° C. $^1$H NMR (300 MHz, CDCl$_3$): δ 2.46 (s, 3H), 2.55 (s, 3H), 7.41-7.47 (m, 4H), 7.52 (d, J=8.6 Hz, 1H), 7.67 (dd, J=8.6, 2.1 Hz, 1H), 8.14 (d, J=0.9 Hz, 1H), 14.30 (s, 1H).

<Example 6> Synthesis of 2-(3-methylphenyl)-3-carboxy-7-methoxy-(4H)-4-benzopyranone Through the general synthesis method of Preparation Example 1 above, a 2-hydroxy-4-methoxybenzophosphorane compound (200 mg, 0.38 mmol), pyridine (0.06 mL, 0.76 mmol, 2 eq), and m-toluoyl chloride (0.05 mL, 0.57 mmol, 1.5 eq) were stirred in methylene chloride (4 mL) for 19 hours, and stirred in toluene (15 mL) for 17 hours, and then stirred in TFA (5 mL) and methylene chloride (5 mL) for 2 hours to obtain 76.3 mg (65.0%) of the final desired compound, 2-(3-methylphenyl)-3-carboxy-7-methoxy-(4H)-4-benzopyranone.

m.p. 183-184° C. $^1$H NMR (300 MHz, CDCl$_3$): δ 2.46 (s, 3H), 3.96 (s, 3H), 6.98 (d, J=2.3 Hz, 1H), 7.14 (dd, J=9.0, 2.3 Hz, 1H), 7.40-7.46 (m, 4H), 8.25 (d, J=9.0 Hz, 1H), 14.45 (s, 1H).

<Example 7> Synthesis of 2-(3-methylphenyl)-3-carboxy-6-methoxy-(4H)-4-benzopyranone Through the general synthesis method of Preparation Example 1 above, a 2-hydroxy-5-methoxybenzophosphorane compound (200 mg, 0.38 mmol), pyridine (0.06 mL, 0.76 mmol, 2 eq), and m-toluoyl chloride (0.05 mL, 0.57 mmol, 1.5 eq) were stirred in methylene chloride (4 mL) for 2 hours, and stirred in toluene (15 mL) for 71 hours, and then stirred in TFA (5 mL) and methylene chloride (5 mL) for 2 hours to obtain 49.5 mg (42.0%) of the final desired compound, 2-(3-methylphenyl)-3-carboxy-6-methoxy-(4H)-4-benzopyranone.

m.p. 198-199° C. $^1$H NMR (300 MHz, CDCl$_3$): δ 2.46 (s, 3H), 3.98 (s, 3H), 7.27-7.46 (m, 5H), 7.56 (d, J=9.2 Hz, 1H), 7.67 (d, J=3.0 Hz, 1H), 14.35 (s, 1H).

<Example 8> Synthesis of 2-(3,4-dimethoxyphenyl)-3-carboxy-(4H)-4-benzopyranone

Through the general synthesis method of Preparation Example 1 above, a 2-hydroxybenzophosphorane compound (200 mg, 0.4 mmol), pyridine (0.05 mL, 0.6 mmol, 1.5 eq), and 3,4-dimethoxybenzoyl chloride (96 mg, 0.48 mmol, 1.2 eq) were stirred in methylene chloride (4 mL) for 150 hours, and stirred in toluene (15 mL) for 72 hours, and then stirred in TFA (5 mL) and methylene chloride (5 mL) for 2 hours to obtain 34.9 mg (63.0%) of the final desired compound, 2-(3,4-dimethoxyphenyl)-3-carboxy-(4H)-4-benzopyranone.

m.p. 237-238° C. $^1$H NMR (300 MHz, CDCl$_3$): δ 3.94 (s, 3H), 3.99 (s, 3H), 7.00 (d, J=8.4 Hz, 1H), 7.23 (d, J=2.1 Hz, 1H), 7.39 (dd, J=8.4, 2.1 Hz, 1H), 7.56-7.64 (m, 2H), 7.64-7.90 (m, 1H), 8.36 (dd, J=8.0, 1.6 Hz, 1H), 14.50 (s, 1H).

<Example 9> Synthesis of 2-(3,4-dimethoxyphenyl)-3-carboxy-7-methoxy-(4H)-4-benzopyranone Through the general synthesis method of Preparation Example 1 above, a 2-hydroxy-4-methoxybenzophosphorane compound (200 mg, 0.38 mmol), pyridine (0.05 mL, 0.57 mmol, 1.5 eq), and 3,4-dimethoxybenzoyl chloride (92 mg, 0.46 mmol, 1.2 eq) were stirred in methylene chloride (4 mL) for 12 hours, and stirred in benzene (10 mL) for 45 hours, and then stirred in TFA (5 mL) and methylene chloride (5 mL) for 2 hours to obtain 59.7 mg (89.0%) of the final desired compound, 2-(3,4-dimethoxyphenyl)-3-carboxy-7-methoxy-(4H)-4-benzopyranone.

m.p. 208-210° C. $^1$H NMR (300 MHz, CDCl$_3$): δ 3.94 (s, 3H), 3.96 (s, 3H), 3.97 (s, 3H), 6.97-6.99 (m, 2H), 7.12 (dd, J=8.9, 2.3 Hz, 1H), 7.20 (d, J=1.9 Hz, 1H), 7.34 (dd, J=8.4, 1.9 Hz, 1H), 8.22 (d, J=8.9 Hz, 1H).

<Example 10> Synthesis of 2-(2-chlorophenyl)-3-carboxy-7-methoxy-(4H)-4-benzopyranone Through the general synthesis method of Preparation Example 1 above, a 2-hydroxy-4-methoxybenzophosphorane compound (200 mg, 0.38 mmol), pyridine (0.05 mL, 0.57 mmol, 1.5 eq), and 2-chlorobenzoyl chloride (0.06 mL, 0.46 mmol, 1.2 eq) were stirred in methylene chloride (4 mL) for 1 hour, and stirred in toluene (15 mL) for 8 hours, and then stirred in TFA (5 mL) and methylene chloride (5 mL) for 2 hours to obtain 70 mg (88.0%) of the desired compound, 2-(2-chlorophenyl)-3-carboxy-7-methoxy-(4H)-4-benzopyranone.

m.p. 130-132° C. $^1$H NMR (300 MHz, CDCl$_3$): δ 3.96 (s, 3H), 6.98 (d, J=2.4 Hz, 1H), 7.17 (dd, J=9.0, 2.4 Hz, 1H), 7.43-7.44 (m, 2H), 7.48-7.56 (m, 2H), 8.28 (d, J=9.0 Hz, 1H), 14.40 (s, 1H).

<Example 11> Synthesis of 2-(2-chlorophenyl)-3-carboxy-(4H)-4-benzopyranone

Through the general synthesis method of Preparation Example 1 above, a 2-hydroxybenzophosphorane compound (200 mg, 0.40 mmol), pyridine (0.05 mL, 0.60 mmol, 1.5 eq), and 2-chlorobenzoyl chloride (0.06 mL, 0.48 mmol, 1.2 eq) were stirred in methylene chloride (4 mL) for 1 hour, and stirred in toluene (15 mL) for 120 hours, and then stirred in TFA (5 mL) and methylene chloride (5 mL) for 6 hours and 30 minutes to obtain 34 mg (44.0%) of the final desired compound, 2-(2-chlorophenyl)-3-carboxy-(4H)-4-benzopyranone.

m.p. 133-135° C. $^1$H NMR (300 MHz, CDCl$_3$): δ 7.44-7.46 (m, 2H), 7.49-7.55 (m, 2H), 7.61-7.66 (m, 2H), 7.87-7.93 (m, 1H), 8.40 (dd, J=8.3, 1.7 Hz, 1H).

<Example 12> Synthesis of 2-(2-thiophenyl)-3-carboxy-8-methoxy-(4H)-4-benzopyranone Through the general synthesis method of Preparation Example 1 above, a 2-hydroxy-3-methoxybenzophosphorane compound (200 mg, 0.38 mmol), pyridine (0.05 mL, 0.57 mmol, 1.5 eq), and 2-thiophenecarbonyl chloride (0.05 mL, 0.46 mmol, 1.2 eq) were stirred in methylene chloride (4 mL) for 2 hours and 30 minutes, and stirred in toluene (15 mL) for 36 hours, and then stirred in TFA (5 mL) and methylene chloride (5 mL) for 2 hours to obtain 52.4 mg (56.0%) of the final desired compound, 2-(2-thiophenyl)-3-carboxy-8-methoxy-(4H)-4-benzopyranone.

m.p. 196-198° C. $^1$H NMR (300 MHz, CDCl$_3$): δ 4.07 (s, 3H), 7.25 (dd, J=5.0, 4.0 Hz, 1H), 7.31 (dd, J=8.1, 1.3 Hz, 1H), 7.46 (dd, J=8.1, 8.1 Hz, 1H), 7.81-7.85 (m, 2H), 8.38 (dd, J=4.0, 1.2 Hz, 1H), 14.80 (s, 1H).

<Example 13> Synthesis of 2-(2-thiophenyl)-3-carboxy-7-methoxy-(4H)-4-benzopyranone Through the general synthesis method of Preparation Example 1 above, a 2-hydroxy-4-methoxybenzophosphorane compound (200 mg, 0.38 mmol), pyridine (0.05 mL, 0.57 mmol, 1.5 eq), and 2-thiophenecarbonyl chloride (0.05 mL, 0.46 mmol, 1.2 eq) were stirred in methylene chloride (4 mL) for 2 hours and 30 minutes, and stirred in toluene (15 mL) for 28 hours, and then stirred in TFA (5 mL) and methylene chloride (5 mL) for 2 hours to obtain 41 mg (77.0%) of the final desired compound, 2-(2-thiophenyl)-3-carboxy-7-methoxy-(4H)-4-benzopyranone.

m.p. 205-207° C. $^1$H NMR (300 MHz, CDCl$_3$): δ 3.97 (s, 3H), 6.95 (d, J=2.3 Hz, 1H), 7.09 (dd, J=9.0, 2.3 Hz, 1H), 7.22 (dd, J=5.0, 4.0 Hz, 1H), 7.79 (dd, J=5.0, 1.1 Hz, 1H), 8.19 (d, J=9.0 Hz, 1H), 8.25 (dd, J=4.0, 1.1 Hz, 1H), 14.98 (s, 1H).

<Example 14> Synthesis of 2-(2-thiophenyl)-3-carboxy-6-methoxy-(4H)-4-benzopyranone Through the general synthesis method of Preparation Example 1 above, a 2-hydroxy-5-methoxybenzophosphorane compound (200 mg, 0.38 mmol), pyridine (0.05 mL, 0.57 mmol, 1.5 eq), and 2-thiophenecarbonyl chloride (0.05 mL, 0.46 mmol, 1.2 eq) were stirred in methylene chloride (4 mL) for 2 hours and 30 minutes, and stirred in toluene (15 mL) for 42 hours, and then stirred in TFA (5 mL) and methylene chloride (5 mL) for 1 hour and 30 minutes to obtain 50 mg (68.0%) of the final desired compound, 2-(2-thiophenyl)-3-carboxy-6-methoxy-(4H)-4-benzopyranone.

m.p. 172-174° C. $^1$H NMR (300 MHz, CDCl$_3$): δ 3.96 (s, 3H), 7.24 (dd, J=5.0, 4.0 Hz, 1H), 7.43 (dd, J=9.2, 3.0 Hz, 1H), 7.55 (d, J=9.2 Hz, 1H), 7.63 (d, J=3.0 Hz, 1H), 7.81 (dd, J=5.0, 1.2 Hz, 1H), 8.25 (dd, J=4.0, 1.2 Hz, 1H), 14.78 (s, 1H).

<Example 15> Synthesis of 2-(2-thiophenyl)-3-carboxy-(4H)-4-benzopyranone

Through the general synthesis method of Preparation Example 1 above, a 2-hydroxybenzophosphorane compound (200 mg, 0.40 mmol), pyridine (0.05 mL, 0.60 mmol, 1.5 eq), and 2-thiophenecarbonyl chloride (0.05 mL, 0.48 mmol, 1.2 eq) were stirred in methylene chloride (4 mL) for 3 hours, and stirred in toluene (15 mL) for 23 hours and 30 minutes, and then stirred in TFA (5 mL) and methylene chloride (5 mL) for 2 hours to obtain 52.3 mg (78.0%) of the final desired compound, 2-(2-thiophenyl)-3-carboxy-(4H)-4-benzopyranone.

m.p. 175-176° C. $^1$H NMR (300 MHz, CDCl$_3$): δ 7.25 (dd, J=5.0, 4.1 Hz, 1H), 7.55-7.64 (m, 2H), 7.83-7.89 (m, 2H), 8.29-8.34 (m, 2H), 14.70 (s, 1H).

<Example 16> Synthesis of 2-(3-fluorophenyl)-3-carboxy-(4H)-4-benzopyranone

Through the general synthesis method of Preparation Example 1 above, a 2-hydroxybenzophosphorane compound (300 mg, 0.6 mmol), diisopropylethylamine (0.314 mL, 1.8 mmol, 3 eq), 3-fluorobenzoyl chloride (0.118 mL, 1.2 mmol, 2 eq), and 4-(dimethylamino)pyridine (10 mg) were stirred in methylene chloride (5 mL) for 1 hour, and stirred in toluene (15 mL) for 4 hours and 30 minutes, and then stirred in TFA (7 mL) and methylene chloride (7 mL) for 1 hour and 30 minutes to obtain 154 mg (90.0%) of the final desired compound, 2-(3-fluorophenyl)-3-carboxy-(4H)-4-benzopyranone.

m.p. 193-196° C. $^1$H NMR (300 MHz, CDCl$_3$): δ 7.29-7.55 (m, 4H), 7.60-7.65 (m, 2H), 7.87-7.93 (m, 1H), 8.37-8.40 (m, 1H), 14.19 (s, 1H).

<Example 17> Synthesis of 2-(3,5-difluorophenyl)-3-carboxy-(4H)-4-benzopyranone

Through the general synthesis method of Preparation Example 1 above, a 2-hydroxybenzophosphorane compound (300 mg, 0.6 mmol), diisopropylethylamine (0.314 mL, 1.8 mmol, 3 eq), 3,5-difluorobenzoyl chloride (0.15 mL, 1.2 mmol, 2 eq), and 4-(dimethylamino)pyridine (10 mg) were stirred in methylene chloride (5 mL) for 1 hour, and stirred in toluene (15 mL) for 2 hours and 30 minutes, and then stirred in TFA (7 mL) and methylene chloride (7 mL) for 1 hour to obtain 22 mg (12.0%) of the final desired compound, 2-(3,5-difluorophenyl)-3-carboxy-(4H)-4-benzopyranone.

m.p. 208-209° C. $^1$H NMR (300 MHz, CDCl$_3$): δ 7.02-7.08 (m, 1H), 7.16-7.19 (m, 2H), 7.62-66 (m, 2H), 7.89-7.94 (m, 1H), 8.38 (d, J=8.3 Hz, 1H).

<Example 18> Synthesis of 2-(2-furanyl)-3-carboxy-(4H)-4-benzopyranone

Through the general synthesis method of Preparation Example 1 above, a 2-hydroxybenzophosphorane compound (300 mg, 0.6 mmol), diisopropylethylamine (0.314 mL, 1.8 mmol, 3 eq), 2-furoyl chloride (0.118 mL, 1.2 mmol, 2 eq), and 4-(dimethylamino)pyridine (10 mg) were stirred in methylene chloride (5 mL) for 1 hour, and stirred in toluene (15 mL) for 8 hours, and then stirred in TFA (7 mL) and methylene chloride (7 mL) for 1 hour to obtain 96 mg (62.0%) of the final desired compound, 2-(2-furanyl)-3-carboxy-(4H)-4-benzopyranone.

m.p. 202-205° C. $^1$H NMR (300 MHz, CDCl$_3$): δ 6.72 (dd, J=3.8, 1.7 Hz, 1H), 7.54-7.60 (m, 1H), 7.65 (d, J=8.4 Hz, 1H), 7.81-7.89 (m, 2H), 8.01-8.03 (m, 1H), 8.32 (dd, J=8.0, 1.5 Hz, 1H), 14.45 (s, 1H).

<Example 19> Synthesis of 2-(3-methylphenyl)-3-carboxy-(4H)-4-benzopyranone

Through the general synthesis method of Preparation Example 1 above, a 2-hydroxybenzophosphorane compound (300 mg, 0.6 mmol), diisopropylethylamine (0.314 mL, 1.8 mmol, 3 eq), m-toluoyl chloride (0.158 mL, 1.2 mmol, 2 eq), and 4-(dimethylamino)pyridine (10 mg) were stirred in methylene chloride (5 mL) for 1 hour, and stirred in toluene (15 mL) for 72 hours, and then stirred in TFA (7 mL) and methylene chloride (7 mL) for 1 hour to obtain 73 mg (43.0%) of the final desired compound, 2-(3-methylphenyl)-3-carboxy-(4H)-4-benzopyranone.

m.p. 162-164° C. $^1$H NMR (300 MHz, CDCl$_3$): δ 2.48 (s, 3H), 7.43-7.50 (m, 4H), 7.59-7.65 (m, 2H), 7.86-7.92 (m, 1H), 8.38 (dd, J=8.0, 1.5 Hz, 1H), 14.20 (s, 1H).

<Example 20> Synthesis of 2-(2-furanyl)-3-carboxy-8-methyl-(4H)-4-benzopyranone

Through the general synthesis method of Preparation Example 1 above, a 2-hydroxy-3-methylbenzophosphorane compound (100 mg, 0.20 mmol), diisopropylethylamine (0.068 mL, 0.40 mmol, 2 eq), 2-furoyl chloride (0.029 mL, 0.30 mmol, 1.5 eq), 4-(dimethylamino)pyridine (5 mg) were stirred in methylene chloride (3 mL) for 2 hours, and stirred in toluene (6 mL) for 50 hours, and then stirred in TFA (3 mL) and methylene chloride (3 mL) for 1 hour to obtain 31.4 mg (59.3%) of the final desired compound, 2-(2-furanyl)-3-carboxy-8-methyl-(4H)-4-benzopyranone.

m.p. 227-228° C. $^1$H NMR (300 MHz, CDCl$_3$): δ 2.58 (s, 3H), 6.69 (dd, J=3.6, 1.7 Hz, 1H), 7.32-7.36 (m, 2H), 7.59 (d, J=7.3 Hz, 1H), 7.76-7.77 (m, 1H), 7.98 (d, J=7.3 Hz, 1H).

<Example 21> Synthesis of 2-(2-furanyl)-3-carboxy-7-methyl-(4H)-4-benzopyranone

Through the general synthesis method of Preparation Example 1 above, a 2-hydroxy-4-methylbenzophosphorane compound (100 mg, 0.20 mmol), diisopropylethylamine (0.068 mL, 0.40 mmol, 2 eq), 2-furoyl chloride (0.029 mL, 0.30 mmol, 1.5 eq), and 4-(dimethylamino)pyridine (5 mg) were stirred in methylene chloride (3 mL) for 2 hours, and stirred in toluene (6 mL) for 50 hours, and then stirred in TFA (3 mL) and methylene chloride (3 mL) for 1 hour to obtain 19.1 mg (36.1%) of the final desired compound, 2-(2-furanyl)-3-carboxy-7-methyl-(4H)-4-benzopyranone.

m.p. 217-218° C. $^1$H NMR (300 MHz, CDCl$_3$): δ 2.57 (s, 3H), 6.71 (dd, J=3.7, 1.7 Hz, 1H), 7.37 (dd, J=8.2, 0.8 Hz, 1H), 7.46 (s, 1H), 7.79 (d, J=1.7 Hz, 1H), 8.00 (d, J=3.7 Hz, 1H), 8.18 (d, J=8.2 Hz, 1H), 14.55 (s, 1H).

<Example 22> Synthesis of 2-(2-furanyl)-3-carboxy-6-methyl-(4H)-4-benzopyranone

Through the general synthesis method of Preparation Example 1 above, a 2-hydroxy-5-methylbenzophosphorane compound (100 mg, 0.20 mmol), diisopropylethylamine (0.068 mL, 0.40 mmol, 2 eq), 2-furoyl chloride (0.029 mL, 0.30 mmol, 1.5 eq), and 4-(dimethylamino)pyridine (5 mg) were stirred in methylene chloride (3 mL) for 2 hours, and stirred in toluene (6 mL) for 50 hours, and then stirred in TFA (3 mL) and methylene chloride (3 mL) for 1 hour to obtain 25.2 mg (47.6%) of the final desired compound, 2-(2-furanyl)-3-carboxy-6-methyl-(4H)-4-benzopyranone.

m.p. 195-197° C. $^1$H NMR (300 MHz, CDCl$_3$): δ 2.53 (s, 3H), 6.71 (dd, J=3.7, 1.7 Hz, 1H), 7.55 (d, J=8.6 Hz, 1H), 7.66 (dd, J=8.6, 2.0 Hz, 1H), 7.79 (d, J=1.7 Hz, 1H), 7.99 (d, J=3.7 Hz, 1H), 8.09 (s, 1H), 14.55 (s, 1H).

<Example 23> Synthesis of 2-(2-furanyl)-3-carboxy-6-chloro-(4H)-4-benzopyranone

Through the general synthesis method of Preparation Example 1 above, a 2-hydroxy-5-chlorobenzophosphorane compound (100 mg, 0.19 mmol), diisopropylethylamine (0.066 mL, 0.38 mmol, 2 eq), 2-furoyl chloride (0.028 mL, 0.29 mmol, 1.5 eq), and 4-(dimethylamino)pyridine (5 mg) were stirred in methylene chloride (3 mL) for 2 hours, and stirred in toluene (6 mL) for 50 hours, and then stirred in TFA (3 mL) and methylene chloride (3 mL) for 1 hour to obtain 20.20 mg (36.9%) of the final desired compound, 2-(2-furanyl)-3-carboxy-6-chloro-(4H)-4-benzopyranone.

m.p. 196-198° C. $^1$H NMR (300 MHz, CDCl$_3$): δ 6.73 (dd, J=3.8, 1.7 Hz, 1H), 7.62 (d, J=9.0 Hz, 1H), 7.77-7.81 (m, 2H), 8.04 (dd, J=3.8, 0.5 Hz, 1H), 8.27 (d, J=2.5 Hz, 1H), 14.00 (s, 1H).

<Example 24> Synthesis of 2-(2-furanyl)-3-carboxy-6-bromo-(4H)-4-benzopyranone

Through the general synthesis method of Preparation Example 1 above, a 2-hydroxy-5-bromobenzophosphorane compound (100 mg, 0.17 mmol), diisopropylethylamine (0.061 mL, 0.34 mmol, 2 eq), 2-furoyl chloride (0.026 mL, 0.26 mmol, 1.5 eq), and 4-(dimethylamino)pyridine (5 mg) were stirred in methylene chloride (3 mL) for 2 hours, and stirred in toluene (6 mL) for 50 hours, and then stirred in TFA (3 mL) and methylene chloride (3 mL) for 1 hour to obtain 41.9 mg (71.9%) of the final desired compound, 2-(2-furanyl)-3-carboxy-6-bromo-(4H)-4-benzopyranone.

m.p. 209-211° C. $^1$H NMR (300 MHz, CDCl$_3$): δ 6.73 (dd, J=3.8, 1.6 Hz, 1H), 7.55 (d, J=8.9 Hz, 1H), 7.80-7.81 (m, 1H), 7.93 (dd, J=8.9, 2.4 Hz, 1H), 8.03 (d, J=3.8 Hz, 1H), 8.43 (d, J=2.4 Hz, 1H), 14.25 (s, 1H).

<Example 25> Synthesis of 2-(3-methylphenyl)-3-carboxy-8-methyl-(4H)-4-benzopyranone Through the general synthesis method of Preparation Example 1 above, a 2-hydroxy-3-methylbenzophosphorane compound (100 mg, 0.20 mmol), diisopropylethylamine (0.068 mL, 0.40 mmol, 2 eq), m-toluoyl chloride (0.031 mL, 0.24 mmol, 1.2 eq), and 4-(dimethylamino)pyridine (5 mg) were stirred in methylene chloride (3 mL) for 24 hours, and stirred in toluene (6 mL) for 144 hours, and then stirred in TFA (3 mL) and methylene chloride (3 mL) for 1 hour and 30 minutes to obtain 14.0 mg (24.3%) of the final desired compound, 2-(3-methylphenyl)-3-carboxy-8-methyl-(4H)-4-benzopyranone.

m.p. 209-211° C. $^1$H NMR (300 MHz, CDCl$_3$): δ 2.47 (s, 3H), 2.55 (s, 3H), 7.42-7.51 (m, 5H), 7.70 (d, J=7.1 Hz, 1H), 8.19 (d, J=7.1 Hz, 1H), 14.25 (s, 1H).

<Example 26> Synthesis of 2-(3-methylphenyl)-3-carboxy-7-methyl-(4H)-4-benzopyranone Through the general synthesis method of Preparation Example 1 above, a 2-hydroxy-4-methylbenzophosphorane compound (100 mg, 0.20 mmol), diisopropylethylamine (0.068 mL, 0.40 mmol, 2 eq), m-toluoyl chloride (0.031 mL, 0.24 mmol, 1.2 eq), and 4-(dimethylamino)pyridine (5 mg) were stirred in methylene chloride (3 mL) for 24 hours, and stirred in toluene (6 mL) for 144 hours, and then stirred in TFA (3 mL) and methylene chloride (3 mL) for 1 hour and 30 minutes to obtain 23.2 mg (40.4%) of the final desired compound, 2-(3-methylphenyl)-3-carboxy-7-methyl-(4H)-4-benzopyranone.

m.p. 152-155° C. $^1$H NMR (300 MHz, CDCl$_3$): δ 2.46 (s, 3H), 2.57 (s, 3H), 7.39-7.47 (m, 6H), 8.24 (d, J=8.5 Hz, 1H), 14.30 (s, 1H).

<Example 27> Synthesis of 2-(3-methylphenyl)-3-carboxy-6-methyl-(4H)-4-benzopyranone Through the general synthesis method of Preparation Example 1 above, a 2-hydroxy-5-methylbenzophosphorane compound (100 mg, 0.20 mmol), diisopropylethylamine (0.068 mL, 0.40 mmol, 2 eq), m-toluoyl chloride (0.031 mL, 0.24 mmol, 1.2 eq), and 4-(dimethylamino)pyridine (5 mg) were stirred in methylene chloride (3 mL) for 24 hours, and stirred in toluene (6 mL) for 144 hours, and then stirred in TFA (3 mL) and methylene chloride (3 mL) for 1 hour and 30 minutes to obtain 23.1 mg (40.1%) of the final desired compound, 2-(3-methylphenyl)-3-carboxy-6-methyl-(4H)-4-benzopyranone.

m.p. 192-195° C. $^1$H NMR (300 MHz, CDCl$_3$): δ 2.46 (s, 3H), 2.55 (s, 3H), 7.41-7.47 (m, 4H), 7.52 (d, J=8.6 Hz, 1H), 7.67 (dd, J=8.6, 2.1 Hz, 1H), 8.14 (d, J=0.9 Hz, 1H), 14.30 (s, 1H).

<Example 28> Synthesis of 2-(3-methylphenyl)-3-carboxy-7-chloro-(4H)-4-benzopyranone Through the general synthesis method of Preparation Example 1 above, a 2-hydroxy-4-chlorobenzophosphorane compound (100 mg, 0.19 mmol), diisopropylethylamine (0.066 mL, 0.38 mmol, 2 eq), m-toluoyl chloride (0.030 mL, 0.23 mmol, 1.2 eq), and 4-(dimethylamino)pyridine (5 mg) were stirred in methylene chloride (3 mL) for 24 hours, and stirred in toluene (6 mL) for 144 hours, and then stirred in TFA (3 mL) and methylene chloride (3 mL) for 1 hour and 30 minutes to obtain 28.4 mg (48.0%) of the final desired compound, 2-(3-methylphenyl)-3-carboxy-7-chloro-(4H)-4-benzopyranone.

m.p. 179-181° C. $^1$H NMR (300 MHz, CDCl$_3$): δ 2.46 (s, 3H), 7.43-7.46 (m, 4H), 7.56 (dd, J=8.6, 1.5 Hz, 1H), 7.66 (s, 1H), 8.30 (d, J=8.6 Hz, 1H), 13.95 (s, 1H).

<Example 29> Synthesis of 2-(3-methylphenyl)-3-carboxy-6-chloro-(4H)-4-benzopyranone Through the general synthesis method of Preparation Example 1 above, a 2-hydroxy-5-chlorobenzophosphorane compound (100 mg, 0.19 mmol), diisopropylethylamine (0.066 mL, 0.38 mmol, 2 eq), m-toluoyl chloride (0.030 mL, 0.23 mmol, 1.2 eq), and 4-(dimethylamino)pyridine (5 mg) were stirred in methylene chloride (3 mL) for 24 hours, and stirred in toluene (6 mL) for 144 hours, and then stirred in TFA (3 mL) and methylene chloride (3 mL) for 1 hour and 30 minutes to obtain 13.4 mg (22.6%) of the final desired compound, 2-(3-methylphenyl)-3-carboxy-6-chloro-(4H)-4-benzopyranone.

m.p. 218-220° C. $^1$H NMR (300 MHz, CDCl$_3$): δ 2.46 (s, 3H), 7.44-7.47 (m, 4H), 7.52 (d, J=8.9 Hz, 1H), 7.95 (dd, J=8.9, 2.4 Hz, 1H), 8.49 (d, J=2.4 Hz, 1H), 13.80 (s, 1H).

<Example 30> Synthesis of 2-(3-methylphenyl)-3-carboxy-6-bromo-(4H)-4-benzopyranone Through the general synthesis method of Preparation Example 1 above, a 2-hydroxy-5-bromobenzophosphorane compound (100 mg, 0.17 mmol), diisopropylethylamine (0.061 mL, 0.34 mmol, 2 eq), m-toluoyl chloride (0.027 mL, 0.20 mmol, 1.2 eq), and 4-(dimethylamino)pyridine (5 mg) were stirred in methylene chloride (3 mL) for 24 hours, and stirred in toluene (6 mL) for 144 hours, and then stirred in TFA (3 mL) and methylene chloride (3 mL) for 1 hour and 30 minutes to obtain 21.6 mg (34.6%) of the final desired compound, 2-(3-methylphenyl)-3-carboxy-6-bromo-(4H)-4-benzopyranone.

m.p. 208-210° C. $^1$H NMR (300 MHz, CDCl$_3$): δ 2.47 (s, 3H), 7.42-7.47 (m, 4H), 7.59 (d, J=8.9 Hz, 1H), 7.80 (dd, J=8.9, 2.5 Hz, 1H), 8.32 (d, J=2.5 Hz, 1H), 13.90 (s, 1H).

<Example 31> Synthesis of 2-(2-thiophenyl)-3-carboxy-8-methyl-(4H)-4-benzopyranone Through the general synthesis method of Preparation Example 1 above, a 2-hydroxy-3-methylbenzophosphorane compound (100 mg, 0.20 mmol), diisopropylethylamine (0.068 mL, 0.40 mmol, 2 eq), 2-thiophenecarbonyl chloride (0.031 mL, 0.30 mmol, 1.5 eq), and 4-(dimethylamino)pyridine (5 mg) were stirred in methylene chloride (3 mL) for 1 hour, and stirred in toluene (6 mL) for 21 hours, and then stirred in TFA (3 mL) and methylene chloride (3 mL) for 1 hour to obtain 26.5 mg (47.3%) of the final desired compound, 2-(2-thiophenyl)-3-carboxy-8-methyl-(4H)-4-benzopyranone.

m.p. 205-206° C. $^1$H NMR (300 MHz, CDCl$_3$): δ 2.63 (s, 3H), 7.25-7.26 (m, 4H), 7.45 (dd, J=7.7, 7.7 Hz, 1H), 7.68 (d, J=7.7 Hz, 1H), 7.83 (dd, J=5.0, 1.0 Hz, 1H), 8.14 (d, J=7.7 Hz, 1H), 8.38 (dd, J=4.0, 1.0 Hz, 1H).

<Example 32> Synthesis of 2-(2-thiophenyl)-3-carboxy-7-methyl-(4H)-4-benzopyranone Through the general synthesis method of Preparation Example 1 above, a 2-hydroxy-4-methylbenzophosphorane compound (100 mg, 0.20 mmol), diisopropylethylamine (0.068 mL, 0.40 mmol, 2 eq), 2-thiophenecarbonyl chloride (0.031 mL, 0.30 mmol, 1.5 eq), and 4-(dimethylamino)pyridine (5 mg) were stirred in methylene chloride (3 mL) for 1 hour, and stirred in toluene (6 mL) for 21 hours, and then stirred in TFA (3 mL) and methylene chloride (3 mL) for 1 hour to obtain 30.1 mg (53.8%) of the final desired compound, 2-(2-thiophenyl)-3-carboxy-7-methyl-(4H)-4-benzopyranone.

m.p. 202-203° C. $^1$H NMR (300 MHz, CDCl$_3$): δ 2.58 (s, 3H), 7.24 (dd, J=5.0, 4.0 Hz, 1H), 7.37 (d, J=8.2 Hz, 1H), 7.42 (s, 1H), 7.82 (dd, J=5.0, 1.1 Hz, 1H), 8.18 (d, J=8.2 Hz, 1H), 8.28 (dd, J=4.0, 1.1 Hz, 1H), 14.80 (s, 1H).

<Example 33> Synthesis of 2-(2-thiophenyl)-3-carboxy-6-methyl-(4H)-4-benzopyranone Through the general synthesis method of Preparation Example 1 above, a 2-hydroxy-5-methylbenzophosphorane compound (100 mg, 0.20 mmol), diisopropylethylamine (0.068 mL, 0.40 mmol, 2 eq), 2-thiophenecarbonyl chloride (0.031 mL, 0.30 mmol, 1.5 eq), and 4-(dimethylamino)pyridine (5 mg) were stirred in methylene chloride (3 mL) for 1 hour, and stirred in toluene (6 mL) for 30 hours, and then stirred in TFA (3 mL) and methylene chloride (3 mL)

for 1 hour to obtain 50 mg (89%) of the final desired compound, 2-(2-thiophenyl)-3-carboxy-6-methyl-(4H)-4-benzopyranone.

m.p. 153-155° C. $^1$H NMR (300 MHz, CDCl$_3$): δ 2.54 (s, 3H), 7.24 (dd, J=5.0, 4.0 Hz, 1H), 7.52 (d, J=8.6 Hz, 1H), 7.66 (dd, J=8.6, 2.0 Hz, 1H), 7.82 (dd, J=5.0, 1.1 Hz, 1H), 8.09 (s, 1H), 8.28 (dd, J=4.0, 1.1 Hz, 1H), 14.75 (s, 1H).

<Example 34> Synthesis of 2-(2-thiophenyl)-3-carboxy-7-chloro-(4H)-4-benzopyranone Through the general synthesis method of Preparation Example 1 above, a 2-hydroxy-4-chlorobenzophosphorane compound (100 mg, 0.19 mmol), diisopropylethylamine (0.066 mL, 0.38 mmol, 2 eq), 2-thiophenecarbonyl chloride (0.030 mL, 0.29 mmol, 1.5 eq), and 4-(dimethylamino)pyridine (5 mg) were stirred in methylene chloride (3 mL) for 1 hour, and stirred in toluene (6 mL) for 24 hours, and then stirred in TFA (3 mL) and methylene chloride (3 mL) for 1 hour to obtain 37.0 mg (63.8%) of the final desired compound, 2-(2-thiophenyl)-3-carboxy-7-chloro-(4H)-4-benzopyranone.

m.p. 232-233° C. $^1$H NMR (300 MHz, CDCl$_3$): δ 7.20 (dd, J=5.0, 4.0 Hz, 1H), 7.42 (dd, J=8.5, 1.8 Hz, 1H), 7.60 (d, J=1.8 Hz, 1H), 7.73 (dd, J=5.0, 1.0 Hz, 1H), 7.93 (dd, J=4.0, 1.0 Hz, 1H), 8.15 (d, J=8.5 Hz, 1H).

<Example 35> Synthesis of 2-(2-thiophenyl)-3-carboxy-6-chloro-(4H)-4-benzopyranone Through the general synthesis method of Preparation Example 1 above, a 2-hydroxy-5-chlorobenzophosphorane compound (100 mg, 0.19 mmol), diisopropylethylamine (0.066 mL, 0.38 mmol, 2 eq), 2-thiophenecarbonyl chloride (0.030 mL, 0.29 mmol, 1.5 eq), and 4-(dimethylamino)pyridine (5 mg) were stirred in methylene chloride (3 mL) for 1 hour, and stirred in toluene (6 mL) for 72 hours, and then stirred in TFA (3 mL) and methylene chloride (3 mL) for 1 hour to obtain 36.7 mg (63.3%) of the final desired compound, 2-(2-thiophenyl)-3-carboxy-6-chloro-(4H)-4-benzopyranone.

m.p. 202-204° C. $^1$H NMR (300 MHz, CDCl$_3$): δ 7.24 (dd, J=5.0, 4.0 Hz, 1H), 7.57 (d, J=8.9 Hz, 1H), 7.77 (dd, J=8.9, 2.5 Hz, 1H), 7.84 (dd, J=5.0, 1.1 Hz, 1H), 8.25 (d, J=2.5 Hz, 1H), 8.28 (dd, J=4.0, 1.1 Hz, 1H), 14.45 (s, 1H).

<Example 36> Synthesis of 2-(2-thiophenyl)-3-carboxy-6-bromo-(4H)-4-benzopyranone Through the general synthesis method of Preparation Example 1 above, a 2-hydroxy-5-bromobenzophosphorane compound (100 mg, 0.17 mmol), diisopropylethylamine (0.061 mL, 0.34 mmol, 2 eq), 2-thiophenecarbonyl chloride (0.028 mL, 0.26 mmol, 1.5 eq), and 4-(dimethylamino)pyridine (5 mg) were stirred in methylene chloride (3 mL) for 1 hour, and stirred in toluene (6 mL) for 72 hours, and then stirred in TFA (3 mL) and methylene chloride (3 mL) for 1 hour to obtain 46.2 mg (75.7%) of the final desired compound, 2-(2-thiophenyl)-3-carboxy-6-bromo-(4H)-4-benzopyranone.

m.p. 210-212° C. $^1$H NMR (300 MHz, CDCl$_3$): δ 7.25 (dd, J=5.0, 4.1 Hz, 1H), 7.52 (d, J=8.9 Hz, 1H), 7.86 (dd, J=5.0, 1.1 Hz, 1H), 7.93 (dd, J=8.9, 2.4 Hz, 1H), 8.30 (dd, J=4.1, 1.1 Hz, 1H), 8.44 (d, J=2.4 Hz, 1H), 14.30 (s, 1H).

<Example 37> Synthesis of 2-(3,4-dimethoxyphenyl)-3-carboxy-8-methyl-(4H)-4-benzopyranone Through the general synthesis method of Preparation Example 1 above, a 2-hydroxy-3-methylbenzophosphorane compound (100 mg, 0.20 mmol), diisopropylethylamine (0.068 mL, 0.40 mmol, 2 eq), 3,4-dimethoxybenzoyl chloride (59 mg, 0.30 mmol, 1.5 eq), and 4-(dimethylamino)pyridine (5 mg) were stirred in methylene chloride (3 mL) for 24 hours, and stirred in toluene (6 mL) for 96 hours, and then stirred in TFA (3 mL) and methylene chloride (3 mL) for 1 hour to obtain 20.3 mg (30.3%) of the final desired compound, 2-(3,4-dimethoxyphenyl)-3-carboxy-8-methyl-(4H)-4-benzopyranone.

m.p. 210-212° C. $^1$H NMR (300 MHz, CDCl$_3$): δ 2.58 (s, 3H), 3.96 (s, 3H), 4.00 (s, 3H), 7.01 (d, J=8.5 Hz, 1H), 7.27 (d, J=2.1 Hz, 1H), 7.43 (dd, J=8.5, 2.1 Hz, 1H), 7.48 (dd, J=7.7, 7.7 Hz, 1H), 7.69 (d, J=7.7 Hz, 1H), 8.18 (d, J=7.7 Hz, 1H), 14.45 (s, 1H).

<Example 38> Synthesis of 2-(3,4-dimethoxyphenyl)-3-carboxy-7-methyl-(4H)-4-benzopyranone Through the general synthesis method of Preparation Example 1 above, a 2-hydroxy-4-methylbenzophosphorane compound (100 mg, 0.20 mmol), diisopropylethylamine (0.068 mL, 0.40 mmol, 2 eq), 3,4-dimethoxybenzoyl chloride (59 mg, 0.30 mmol, 1.5 eq), and 4-(dimethylamino)pyridine (5 mg) were stirred in methylene chloride (3 mL) for 24 hours, and stirred in toluene (6 mL) for 96 hours, and then stirred in TFA (3 mL) and methylene chloride (3 mL) for 1 hour to obtain 28.4 mg (42.4%) of the final desired compound, 2-(3,4-dimethoxyphenyl)-3-carboxy-7-methyl-(4H)-4-benzopyranone.

m.p. 200-201° C. $^1$H NMR (300 MHz, CDCl$_3$): δ 2.58 (s, 3H), 3.96 (s, 3H), 3.99 (s, 3H), 6.99 (d, J=8.5 Hz, 1H), 7.22 (d, J=2.0 Hz, 1H), 7.36-7.43 (m, 3H), 8.22 (d, J=8.1 Hz, 1H), 14.45 (s, 1H).

<Example 39> Synthesis of 2-(3,4-dimethoxyphenyl)-3-carboxy-7-chloro-(4H)-4-benzopyranone Through the general synthesis method of Preparation Example 1 above, a 2-hydroxy-4-chlorobenzophosphorane compound (100 mg, 0.19 mmol), diisopropylethylamine (0.066 mL, 0.38 mmol, 2 eq), 3,4-dimethoxybenzoyl chloride (57 mg, 0.29 mmol, 1.5 eq), and 4-(dimethylamino)pyridine (5 mg) were stirred in methylene chloride (3 mL) for 2 hours, and stirred in toluene (6 mL) for 100 hours, and then stirred in TFA (3 mL) and methylene chloride (3 mL) for 1 hour to obtain 34.8 mg (51.2%) of the final desired compound, 2-(3,4-dimethoxyphenyl)-3-carboxy-7-chloro-(4H)-4-benzopyranone.

m.p. 226-227° C. $^1$H NMR (300 MHz, CDCl$_3$): δ 3.95 (s, 3H), 3.99 (s, 3H), 6.99 (d, J=8.4 Hz, 1H), 7.21 (d, J=2.1 Hz, 1H), 7.38 (dd, J=8.4, 2.1 Hz, 1H), 7.54 (dd, J=8.6, 1.8 Hz, 1H), 7.66 (dd, J=1.8 Hz, 1H), 8.28 (d, J=8.6 Hz, 1H), 14.10 (s, 1H).

<Example 40> Synthesis of 2-(3,4-dimethoxyphenyl)-3-carboxy-6-bromo-(4H)-4-benzopyranone Through the general synthesis method of Preparation Example 1 above, a 2-hydroxy-5-bromobenzophosphorane compound (100 mg, 0.17 mmol), diisopropylethylamine (0.061 mL, 0.34 mmol, 2 eq), 2-thiophenecarbonyl chloride (0.028 mL, 0.26 mmol, 1.5 eq), and 4-(dimethylamino)pyridine (5 mg) were stirred in methylene chloride (3 mL) for 1 hour, and stirred in toluene (6 mL) for 92 hours, and then stirred in TFA (3 mL) and methylene chloride (3 mL)

for 1 hour to obtain 34 mg (48%) of the final desired compound, 2-(3,4-dimethoxyphenyl)-3-carboxy-6-bromo-(4H)-4-benzopyranone.
m.p. 242-243° C. $^1$H NMR (300 MHz, CDCl$_3$): δ 3.95 (s, 3H), 3.99 (s, 3H), 6.99 (d, J=8.4 Hz, 1H), 7.22 (d, J=2.1 Hz, 1H), 7.38 (dd, J=8.4, 2.1 Hz, 1H), 7.53 (d, J=8.9 Hz, 1H), 7.94 (dd, J=8.9, 2.4 Hz, 1H), 8.48 (d, J=2.4 Hz, 1H).

<Example 41> Synthesis of 2-(3-fluorophenyl)-3-carboxy-8-methyl-(4H)-4-benzopyranone Through the general synthesis method of Preparation Example 1 above, a 2-hydroxy-3-methylbenzophosphorane compound (100 mg, 0.20 mmol), diisopropylethylamine (0.068 mL, 0.40 mmol, 2 eq), 3-fluorobenzoyl chloride (0.036 mL, 0.30 mmol, 1.5 eq), and 4-(dimethylamino)pyridine (5 mg) were stirred in methylene chloride (3 mL) for 1 hour, and stirred in toluene (6 mL) for 12 hours, and then stirred in TFA (3 mL) and methylene chloride (3 mL) for 2 hours to obtain 18.7 mg (32.2%) of the final desired compound, 2-(3-fluorophenyl)-3-carboxy-8-methyl-(4H)-4-benzopyranone.
m.p. 227-229° C. $^1$H NMR (300 MHz, CDCl$_3$): δ 2.54 (s, 3H), 7.28-7.33 (m, 1H), 7.39 (d, J=9.3 Hz, 1H), 7.46-7.49 (m. 3H), 7.71 (d, J=7.5 Hz, 1H), 8.19 (d, J=8.0 Hz, 1H).

<Example 42> Synthesis of 2-(3-fluorophenyl)-3-carboxy-7-methyl-(4H)-4-benzopyranone Through the general synthesis method of Preparation Example 1 above, a 2-hydroxy-4-methylbenzophosphorane compound (100 mg, 0.20 mmol), diisopropylethylamine (0.068 mL, 0.40 mmol, 2 eq), 3-fluorobenzoyl chloride (0.036 mL, 0.30 mmol, 1.5 eq), and 4-(dimethylamino)pyridine (5 mg) were stirred in methylene chloride (3 mL) for 1 hour, and stirred in toluene (6 mL) for 10 hours, and then stirred in TFA (3 mL) and methylene chloride (3 mL) for 2 hours to obtain 16.1 mg (27.8%) of the final desired compound, 2-(3-fluorophenyl)-3-carboxy-7-methyl-(4H)-4-benzopyranone.
m.p. 178-181° C. $^1$H NMR (300 MHz, CDCl$_3$): δ 2.58 (s, 3H), 7.28-7.38 (m, 2H), 7.42-7.44 (m, 3H), 7.47-7.54 (m. 1H), 8.23-8.26 (m, 1H), 14.33 (s, 1H).

<Example 43> Synthesis of 2-(3-fluorophenyl)-3-carboxy-6-methyl-(4H)-4-benzopyranone Through the general synthesis method of Preparation Example 1 above, a 2-hydroxy-5-methylbenzophosphorane compound (100 mg, 0.20 mmol), diisopropylethylamine (0.068 mL, 0.40 mmol, 2 eq), 3-fluorobenzoyl chloride (0.036 mL, 0.30 mmol, 1.5 eq), and 4-(dimethylamino)pyridine (5 mg) were stirred in methylene chloride (3 mL) for 1 hour, and stirred in toluene (6 mL) for 21 hours, and then stirred in TFA (3 mL) and methylene chloride (3 mL) for 2 hours to obtain 34.2 mg (59.0%) of the final desired compound, 2-(3-fluorophenyl)-3-carboxy-6-methyl-(4H)-4-benzopyranone.
m.p. 214-215° C. $^1$H NMR (300 MHz, CDCl$_3$): δ 2.56 (s, 3H), 7.30-7.33 (m, 1H), 7.35-7.39 (m, 1H), 7.42-7.45 (m, 1H), 7.47-7.54 (m. 2H), 7.69 (dd, J=8.6, 2.0 Hz, 1H), 8.14 (s, 1H), 14.30 (s, 1H).

<Example 44> Synthesis of 2-(3-fluorophenyl)-3-carboxy-7-chloro-(4H)-4-benzopyranone Through the general synthesis method of Preparation Example 1 above, a 2-hydroxy-4-chlorobenzophosphorane compound (100 mg, 0.19 mmol), diisopropylethylamine (0.066 mL, 0.38 mmol, 2 eq), 3-fluorobenzoyl chloride (0.034 mL, 0.29 mmol, 1.5 eq), and 4-(dimethylamino)pyridine (5 mg) were stirred in methylene chloride (3 mL) for 2 hours, and stirred in toluene (6 mL) for 19 hours, and then stirred in TFA (3 mL) and methylene chloride (3 mL) for 2 hours to obtain 43 mg (71.6%) of the final desired compound, 2-(3-fluorophenyl)-3-carboxy-7-chloro-(4H)-4-benzopyranone.
m.p. 160-163° C. $^1$H NMR (300 MHz, CDCl$_3$): δ 7.30-7.44 (m, 2H), 7.51 (dd, J=8.0, 5.4 Hz, 1H), 7.58 (dd, J=8.6, 1.8 Hz, 1H), 7.66 (d, J=1.8 Hz, 1H), 7.71-7.75 (m, 1H), 8.31 (d, J=8.6 Hz, 1H), 15.35 (s, 1H).

<Example 45> Synthesis of 2-(3-fluorophenyl)-3-carboxy-6-chloro-(4H)-4-benzopyranone Through the general synthesis method of Preparation Example 1 above, a 2-hydroxy-5-chlorobenzophosphorane compound (100 mg, 0.19 mmol), diisopropylethylamine (0.066 mL, 0.38 mmol, 2 eq), 3-fluorobenzoyl chloride (0.034 mL, 0.29 mmol, 1.5 eq), and 4-(dimethylamino)pyridine (5 mg) were stirred in methylene chloride (3 mL) for 2 hours, and stirred in toluene (6 mL) for 24 hours, and then stirred in TFA (3 mL) and methylene chloride (3 mL) for 2 hours to obtain 48.0 mg (80.0%) of the final desired compound, 2-(3-fluorophenyl)-3-carboxy-6-chloro-(4H)-4-benzopyranone.
m.p. 216-217° C. $^1$H NMR (300 MHz, CDCl$_3$): δ 7.29-7.39 (m, 2H), 7.42-7.46 (m, 1H), 7.49-7.56 (m, 1H), 7.60 (d, J=8.9 Hz, 1H), 7.83 (dd, J=8.9, 2.5 Hz, 1H), 8.33 (d, J=2.5 Hz, 1H), 13.80 (s, 1H).

<Example 46> Synthesis of 2-(3-fluorophenyl)-3-carboxy-6-bromo-(4H)-4-benzopyranone Through the general synthesis method of Preparation Example 1 above, a 2-hydroxy-5-bromobenzophosphorane compound (100 mg, 0.17 mmol), diisopropylethylamine (0.061 mL, 0.34 mmol, 2 eq), 3-fluorobenzoyl chloride (0.032 mL, 0.26 mmol, 1.5 eq), and 4-(dimethylamino)pyridine (5 mg) were stirred in methylene chloride (3 mL) for 1 hour, and stirred in toluene (6 mL) for 24 hours, and then stirred in TFA (3 mL) and methylene chloride (3 mL) for 1 hour to obtain 44.9 mg (71.3%) of the final desired compound, 2-(3-fluorophenyl)-3-carboxy-6-bromo-(4H)-4-benzopyranone.
m.p. 222-223° C. $^1$H NMR (300 MHz, CDCl$_3$): δ 7.32-7.38 (m, 2H), 7.44 (d, J=7.8 Hz, 1H), 7.48-7.55 (m. 2H), 7.97 (dd, J=9.7, 2.3 Hz, 1H), 8.50 (d, J=2.3 Hz, 1H), 13.85 (s, 1H).

<Example 47> Synthesis of 2-(3,5-difluorophenyl)-3-carboxy-8-methyl-(4H)-4-benzopyranone Through the general synthesis method of Preparation Example 1 above, a 2-hydroxy-3-methylbenzophosphorane compound (200 mg, 0.40 mmol), diisopropylethylamine (0.136 mL, 0.80 mmol, 2 eq), 3,5-difluorobenzoyl chloride (0.074 mL, 0.60 mmol, 1.5 eq), and 4-(dimethylamino)pyridine (5 mg) were stirred in methylene chloride (4 mL) for 1 hour and 30 minutes, and stirred in toluene (9 mL) for 7 hours, and then stirred in TFA (6 mL) and methylene chloride (6 mL) for 2 hours to obtain 92.2 mg (75.0%) of the final desired compound, 2-(3,5-difluorophenyl)-3-carboxy-8-methyl-(4H)-4-benzopyranone.

m.p. 243-244° C. $^1$H NMR (300 MHz, CDCl$_3$): δ 2.53 (s, 3H), 7.01-7.06 (m, 1H), 7.26-7.33 (m, 2H), 7.42-7.47 (m. 1H), 7.67 (d, J=7.0 Hz, 1H), 8.13 (d, J=7.9 Hz, 1H).

<Example 48> Synthesis of 2-(3,5-difluorophenyl)-3-carboxy-7-methyl-(4H)-4-benzopyranone Through the general synthesis method of Preparation Example 1 above, a 2-hydroxy-4-methylbenzophosphorane compound (200 mg, 0.40 mmol), diisopropylethylamine (0.136 mL, 0.80 mmol, 2 eq), 3,5-difluorobenzoyl chloride (0.074 mL, 0.60 mmol, 1.5 eq), and 4-(dimethylamino)pyridine (5 mg) were stirred in methylene chloride (4 mL) for 1 hour and 30 minutes, and stirred in toluene (9 mL) for 7 hours, and then stirred in TFA (6 mL) and methylene chloride (6 mL) for 2 hours to obtain 77.3 mg (62.9%) of the final desired compound, 2-(3,5-difluorophenyl)-3-carboxy-7-methyl-(4H)-4-benzopyranone.

m.p. 220-222° C. $^1$H NMR (300 MHz, CDCl$_3$): δ 2.65 (s, 3H), 7.07-7.15 (m, 1H), 7.18-7.26 (m, 2H), 7.50 (d, J=8.2 Hz, 2H), 8.31 (d, J=8.2 Hz, 1H), 14.34 (s, 1H).

<Example 49> Synthesis of 2-(3,5-difluorophenyl)-3-carboxy-6-methyl-(4H)-4-benzopyranone Through the general synthesis method of Preparation Example 1 above, a 2-hydroxy-5-methylbenzophosphorane compound (200 mg, 0.40 mml), diisopropylethylamine (0.136 mL, 0.80 mmol, 2 eq), 3,5-difluorobenzoyl chloride (0.074 mL, 0.60 mmol, 1.5 eq), and 4-(dimethylamino)pyridine (5 mg) were stirred in methylene chloride (4 mL) for 1 hour and 30 minutes, and stirred in toluene (9 mL) for 10 hours, and then stirred in TFA (6 mL) and methylene chloride (6 mL) for 2 hours to obtain 75.7 mg (61.5%) of the final desired compound, 2-(3,5-difluorophenyl)-3-carboxy-6-methyl-(4H)-4-benzopyranone.

m.p. 238-240° C. $^1$H NMR (300 MHz, CDCl$_3$): δ 2.63 (s, 3H), 7.07-7.15 (m, 1H), 7.20-7.34 (m, 2H), 7.59 (d, J=8.6 Hz, 1H), 7.77 (dd, J=8.6, 2.1 Hz, 1H), 8.21 (s, 1H), 14.12 (s, 1H).

<Example 50> Synthesis of 2-(3,5-difluorophenyl)-3-carboxy-6-chloro-(4H)-4-benzopyranone Through the general synthesis method of Preparation Example 1 above, a 2-hydroxy-5-chlorobenzophosphorane compound (200 mg, 0.38 mmol), diisopropylethylamine (0.131 mL, 0.75 mmol, 2 eq), 3,5-difluorobenzoyl chloride (0.071 mL, 0.57 mmol, 1.5 eq), and 4-(dimethylamino)pyridine (5 mg) were stirred in methylene chloride (4 mL) for 2 hours, and stirred in toluene (9 mL) for 10 hours, and then stirred in TFA (6 mL) and methylene chloride (6 mL) for 2 hours to obtain 99.0 mg (78.6%) of the final desired compound, 2-(3,5-difluorophenyl)-3-carboxy-6-chloro-(4H)-4-benzopyranone.

m.p. 207-209° C. $^1$H NMR (300 MHz, CDCl$_3$): δ 7.09-7.17 (m, 1H), 7.20-7.12 (m, 2H), 7.66 (d, J=8.9 Hz, 1H), 7.91 (dd, J=8.9, 2.5 Hz, 1H), 8.40 (d, J=2.5 Hz, 1H), 14.00 (s, 1H).

<Example 51> Synthesis of 2-(3,5-difluorophenyl)-3-carboxy-6-bromo-(4H)-4-benzopyranone Through the general synthesis method of Preparation Example 1 above, a 2-hydroxy-5-bromobenzophosphorane compound (200 mg, 0.35 mmol), diisopropylethylamine (0.121 mL, 0.70 mmol, 2 eq), 3,5-difluorobenzoyl chloride (0.066 mL, 0.52 mmol, 1.5 eq), and 4-(dimethylamino)pyridine (5 mg) were stirred in methylene chloride (4 mL) for 2 hours, and stirred in toluene (9 mL) for 10 hours, and then stirred in TFA (6 mL) and methylene chloride (6 mL) for 2 hours to obtain 91.3 mg (69.2%) of the final desired compound, 2-(3,5-difluorophenyl)-3-carboxy-6-bromo-(4H)-4-benzopyranone.

m.p. 216-218° C. $^1$H NMR (300 MHz, CDCl$_3$): δ 7.01-7.08 (m, 1H), 7.14-7.18 (m, 2H), 7.51 (d, J=8.9 Hz, 1H), 7.97 (dd, J=8.9, 2.3 Hz, 1H), 8.48 (d, J=2.3 Hz, 1H), 13.60 (s, 1H).

<Example 52> Synthesis of 2-(2,3-difluorophenyl)-3-carboxy-8-methyl-(4H)-4-benzopyranone Through the general synthesis method of Preparation Example 1 above, a 2-hydroxy-3-methylbenzophosphorane compound (200 mg, 0.40 mmol), diisopropylethylamine (0.136 mL, 0.80 mmol, 2 eq), 2.3-difluorobenzoyl chloride (0.074 mL, 0.60 mmol, 1.5 eq), 4-(dimethylamino)pyridine (5 mg) were stirred in methylene chloride (4 mL) for 1 hour and 30 minutes, and stirred in toluene (9 mL) for 15 hours, and then stirred in TFA (6 mL) and methylene chloride (6 mL) for 2 hours to obtain 68.0 mg (55.3%) of the final desired compound, 2-(2,3-difluorophenyl)-3-carboxy-8-methyl-(4H)-4-benzopyranone.

m.p. 167-169° C. $^1$H NMR (300 MHz, CDCl$_3$): δ 2.51 (s, 3H), 7.26-7.31 (m, 2H), 7.36-7.43 (m, 1H), 7.48-7.53 (m, 1H), 7.71 (d, J=7.3 Hz, 1H), 8.20 (d, J=7.9 Hz, 1H), 14.21 (s, 1H).

<Example 53> Synthesis of 2-(2,3-difluorophenyl)-3-carboxy-7-methyl-(4H)-4-benzopyranone Through the general synthesis method of Preparation Example 1 above, a 2-hydroxy-4-methylbenzophosphorane compound (200 mg, 0.40 mmol), diisopropylethylamine (0.136 mL, 0.80 mmol, 2 eq), 2.3-difluorobenzoyl chloride (0.074 mL, 0.60 mmol, 1.5 eq), and 4-(dimethylamino)pyridine (5 mg) were stirred in methylene chloride (4 mL) for 1 hour and 30 minutes, and stirred in toluene (9 mL) for 15 hours, and then stirred in TFA (6 mL) and methylene chloride (6 mL) for 2 hours to obtain 78.0 mg (63.4%) of the final desired compound, 2-(2,3-difluorophenyl)-3-carboxy-7-methyl-(4H)-4-benzopyranone.

m.p. 155-156° C. $^1$H NMR (300 MHz, CDCl$_3$): δ 2.57 (s, 3H), 7.17-7.27 (m, 3H), 7.42 (d, J=8.2 Hz, 2H), 8.24 (d, J=8.2 Hz, 1H), 14.20 (s, 1H).

<Example 54> Synthesis of 2-(2,3-difluorophenyl)-3-carboxy-6-methyl-(4H)-4-benzopyranone Through the general synthesis method of Preparation Example 1 above, a 2-hydroxy-5-methylbenzophosphorane compound (200 mg, 0.40 mmol), diisopropylethylamine (0.136 mL, 0.80 mmol, 2 eq), 2.3-difluorobenzoyl chloride (0.074 mL, 0.60 mmol, 1.5 eq), and 4-(dimethylamino)pyridine (5 mg) were stirred in methylene chloride (4 mL) for 1 hour and 30 minutes, and stirred in toluene (9 mL) for 15 hours, and then stirred in TFA (6 mL) and methylene chloride (6 mL) for 2 hours to obtain 32.0 mg (26.0%) of the final desired compound, 2-(2,3-difluorophenyl)-3-carboxy-6-methyl-(4H)-4-benzopyranone.

m.p. 120-122° C. $^1$H NMR (300 MHz, CDCl$_3$): δ 2.55 (s, 3H), 7.24-7.30 (m, 2H), 7.35-7.43 (m, 1H), 7.51 (d, J=8.6 Hz, 1H), 7.69 (dd, J=8.6, 2.0 Hz, 1H), 8.14 (s, 1H), 14.15 (s, 1H).

\<Example 55\> Synthesis of 2-(2,3-difluorophenyl)-3-carboxy-7-chloro-(4H)-4-benzopyranone Through the general synthesis method of Preparation Example 1 above, a 2-hydroxy-4-chlorobenzophosphorane compound (200 mg, 0.38 mmol), diisopropylethylamine (0.131 mL, 0.75 mmol, 2 eq), 2.3-difluorobenzoyl chloride (0.071 mL, 0.57 mmol, 1.5 eq), and 4-(dimethylamino)pyridine (5 mg) were stirred in methylene chloride (4 mL) for 1 hour and 30 minutes, and stirred in toluene (9 mL) for 15 hours, and then stirred in TFA (6 mL) and methylene chloride (6 mL) for 2 hours to obtain 26.0 mg (20.6%) of the final desired compound, 2-(2,3-difluorophenyl)-3-carboxy-7-chloro-(4H)-4-benzopyranone.

m.p. 220° C. or more. $^1$H NMR (300 MHz, CDCl$_3$): δ 6.95-7.31 (m, 2H), 7.38-7.46 (m, 1H), 7.69 (dd, J=8.6, 1.8 Hz, 1H), 7.65 (d, J=1.8 Hz, 1H), 8.32 (d, J=8.6 Hz, 1H), 13.85 (s, 1H).

\<Example 56\> Synthesis of 2-(2,3-difluorophenyl)-3-carboxy-6-chloro-(4H)-4-benzopyranone Through the general synthesis method of Preparation Example 1 above, a 2-hydroxy-5-chlorobenzophosphorane compound (200 mg, 0.38 mmol), diisopropylethylamine (0.131 mL, 0.75 mmol, 2 eq), 2.3-difluorobenzoyl chloride (0.071 mL, 0.57 mmol, 1.5 eq), and 4-(dimethylamino)pyridine (5 mg) were stirred in methylene chloride (4 mL) for 1 hour and 30 minutes, and stirred in toluene (9 mL) for 15 hours, and then stirred in TFA (6 mL) and methylene chloride (6 mL) for 2 hours to obtain 34.0 mg (27.0%) of the final desired compound, 2-(2,3-difluorophenyl)-3-carboxy-6-chloro-(4H)-4-benzopyranone.

m.p. 120° C. or more. $^1$H NMR (300 MHz, CDCl$_3$): δ 7.24-7.32 (m, 2H), 7.38-7.47 (m, 1H), 7.60 (d, J=8.9 Hz, 1H), 7.84 (dd, J=8.9, 2.5 Hz, 1H), 8.35 (d, J=2.5 Hz, 1H), 13.81 (s, 1H).

\<Example 57\> Synthesis of 2-(2,3-difluorophenyl)-3-carboxy-6-bromo-(4H)-4-benzopyranone Through the general synthesis method of Preparation Example 1 above, a 2-hydroxy-5-bromobenzophosphorane compound (200 mg, 0.35 mmol), diisopropylethylamine (0.121 mL, 0.70 mmol, 2 eq), 3,5-difluorobenzoyl chloride (0.066 mL, 0.52 mmol, 1.5 eq), and 4-(dimethylamino)pyridine (5 mg) were stirred in methylene chloride (4 mL) for 1 hour and 30 minutes, and stirred in toluene (9 mL) for 15 hours, and then stirred in TFA (6 mL) and methylene chloride (6 mL) for 2 hours to obtain 90.0 mg (68.2%) of the final desired compound, 2-(2,3-difluorophenyl)-3-carboxy-6-bromo-(4H)-4-benzopyranone.

m.p. 120° C. or more. $^1$H NMR (300 MHz, CDCl$_3$): δ 7.17-7.53 (m, 3H), 7.61 (dd, J=8.8, 2.3 Hz, 1H), 7.91-7.98 (m, 1H), 8.43 (d, J=2.3 Hz, 1H), 11.80 (s, 1H).

\<Example 58\> Synthesis of 2-(2,5-difluorophenyl)-3-carboxy-8-methyl-(4H)-4-benzopyranone Through the general synthesis method of Preparation Example 1 above, a 2-hydroxy-3-methylbenzophosphorane compound (200 mg, 0.40 mmol), diisopropylethylamine (0.136 mL, 0.80 mmol, 2 eq), 2.5-difluorobenzoyl chloride (0.074 mL, 0.60 mmol, 1.5 eq), and 4-(dimethylamino)pyridine (5 mg) were stirred in methylene chloride (4 mL) for 2 hours, and stirred in toluene (9 mL) for 15 hours, and then stirred in TFA (6 mL) and methylene chloride (6 mL) for 2 hours to obtain 104.5 mg (85.0%) of the final desired compound, 2-(2,5-difluorophenyl)-3-carboxy-8-methyl-(4H)-4-benzopyranone.

m.p. 170-172° C. $^1$H NMR (300 MHz, CDCl$_3$): δ 2.54 (s, 3H), 7.20-7.31 (m, 3H), 7.51 (dd, J=7.6, 7.6 Hz, 1H), 7.73 (d, J=7.6 Hz, 1H), 8.21 (d, J=7.6 Hz, 1H), 14.19 (s, 1H).

\<Example 59\> Synthesis of 2-(2,5-difluorophenyl)-3-carboxy-7-methyl-(4H)-4-benzopyranone Through the general synthesis method of Preparation Example 1 above, a 2-hydroxy-4-methylbenzophosphorane compound (200 mg, 0.40 mmol), diisopropylethylamine (0.136 mL, 0.80 mmol, 2 eq), 2.5-difluorobenzoyl chloride (0.074 mL, 0.60 mmol, 1.5 eq), and 4-(dimethylamino)pyridine (5 mg) were stirred in methylene chloride (4 mL) for 2 hours, and stirred in toluene (9 mL) for 15 hours, and then stirred in TFA (6 mL) and methylene chloride (6 mL) for 2 hours to obtain 84.9 mg (69.0%) of the final desired compound, 2-(2,5-difluorophenyl)-3-carboxy-7-methyl-(4H)-4-benzopyranone.

m.p. 156-158° C. $^1$H NMR (300 MHz, CDCl$_3$): δ 2.59 (s, 3H), 7.15-7.29 (m, 3H), 7.43 (d, J=8.0 Hz, 2H), 8.12 (d, J=8.0 Hz, 1H), 14.21 (s, 1H).

\<Example 60\> Synthesis of 2-(2,5-difluorophenyl)-3-carboxy-6-methyl-(4H)-4-benzopyranone Through the general synthesis method of Preparation Example 1 above, a 2-hydroxy-5-methylbenzophosphorane compound (200 mg, 0.40 mmol), diisopropylethylamine (0.136 mL, 0.80 mmol, 2 eq), 2.5-difluorobenzoyl chloride (0.074 mL, 0.60 mmol, 1.5 eq), and 4-(dimethylamino)pyridine (5 mg) were stirred in methylene chloride (4 mL) for 2 hours, and stirred in toluene (9 mL) for 15 hours, and then stirred in TFA (6 mL) and methylene chloride (6 mL) for 2 hours to obtain 82.3 mg (66.9%) of the final desired compound, 2-(2,5-difluorophenyl)-3-carboxy-6-methyl-(4H)-4-benzopyranone.

m.p. 120° C. or more. $^1$H NMR (300 MHz, CDCl$_3$): δ 2.57 (s, 3H), 7.15-7.30 (m, 3H), 7.52 (d, J=8.6 Hz, 1H), 7.70 (dd, J=8.6, 1.9 Hz, 1H), 8.15 (s, 1H), 14.17 (s, 1H).

\<Example 61\> Synthesis of 2-(2,5-difluorophenyl)-3-carboxy-7-chloro-(4H)-4-benzopyranone Through the general synthesis method of Preparation Example 1 above, a 2-hydroxy-4-chlorobenzophosphorane compound (200 mg, 0.38 mmol), diisopropylethylamine (0.131 mL, 0.75 mmol, 2 eq), 2.5-difluorobenzoyl chloride (0.071 mL, 0.57 mmol, 1.5 eq), and 4-(dimethylamino)pyridine (5 mg) were stirred in methylene chloride (4 mL) for 2 hours, and stirred in toluene (9 mL) for 15 hours, and then stirred in TFA (6 mL) and methylene chloride (6 mL) for 2 hours to obtain 37.6 mg (29.8%) of the final desired compound, 2-(2,5-difluorophenyl)-3-carboxy-7-chloro-(4H)-4-benzopyranone.

m.p. 147-150° C. $^1$H NMR (300 MHz, CDCl$_3$): δ 7.26-7.43 (m, 3H), 7.69 (dd, J=8.6, 1.8 Hz, 1H), 7.75 (d, J=1.8 Hz, 1H), 8.41 (d, J=8.6 Hz, 1H), 13.94 (s, 1H).

\<Example 62\> Synthesis of 2-(2,5-difluorophenyl)-3-carboxy-6-chloro-(4H)-4-benzopyranone Through the general synthesis method of Preparation Example 1 above, a 2-hydroxy-5-chlorobenzophosphorane compound (200 mg, 0.38 mmol), diisopropylethylamine (0.131 mL, 0.75 mmol, 2 eq), 2.5-difluorobenzoyl chloride (0.071 mL, 0.57 mmol, 1.5 eq), and 4-(dimethylamino)pyridine (5 mg) were stirred in methylene chloride (4 mL) for 2 hours, and stirred in toluene (9 mL) for 15 hours, and then stirred in TFA (6 mL) and methylene chloride (6 mL) for 2 hours to obtain 108.8 mg (86.4%) of the final desired compound, 2-(2,5-difluorophenyl)-3-carboxy-6-chloro-(4H)-4-benzopyranone.

m.p. 168-170° C. $^1$H NMR (300 MHz, CDCl$_3$): δ 7.16-7.33 (m, 3H), 7.60 (d, J=8.9 Hz, 1H), 7.84 (dd, J=8.9, 2.5 Hz, 1H), 8.34 (d, J=2.5 Hz, 1H), 13.77 (s, 1H).

<Example 63> Synthesis of 2-(2,5-difluorophenyl)-3-carboxy-6-bromo-(4H)-4-benzopyranone Through the general synthesis method of Preparation Example 1 above, a 2-hydroxy-5-bromobenzophosphorane compound (200 mg, 0.35 mmol), diisopropylethylamine (0.121 mL, 0.70 mmol, 2 eq), 2,5-difluorobenzoyl chloride (0.066 mL, 0.52 mmol, 1.5 eq), and 4-(dimethylamino)pyridine (5 mg) were stirred in methylene chloride (4 mL) for 2 hours, and stirred in toluene (9 mL) for 15 hours, and then stirred in TFA (6 mL) and methylene chloride (6 mL) for 2 hours to obtain 65.2 mg (49.4%) of the final desired compound, 2-(2,5-difluorophenyl)-3-carboxy-6-bromo-(4H)-4-benzopyranone.

m.p. 152-153° C. $^1$H NMR (300 MHz, CDCl$_3$): δ 7.16-7.32 (m, 3H), 7.53 (d, J=8.9 Hz, 1H), 7.98 (dd, J=8.9, 2.3 Hz, 1H), 8.50 (d, J=2.3 Hz, 1H), 13.77 (s, 1H).

<Example 64> Synthesis of 2-(3,4-difluorophenyl)-3-carboxy-8-methyl-(4H)-4-benzopyranone Through the general synthesis method of Preparation Example 1 above, a 2-hydroxy-3-methylbenzophosphorane compound (200 mg, 0.40 mmol), diisopropylethylamine (0.136 mL, 0.80 mmol, 2 eq), 3,4-difluorobenzoyl chloride (0.074 mL, 0.60 mmol, 1.5 eq), and 4-(dimethylamino)pyridine (5 mg) were stirred in methylene chloride (4 mL) for 2 hours, and stirred in toluene (9 mL) for 10 hours, and then stirred in TFA (6 mL) and methylene chloride (6 mL) for 2 hours to obtain 81 mg (66%) of the final desired compound, 2-(3,4-difluorophenyl)-3-carboxy-8-methyl-(4H)-4-benzopyranone.

m.p. 203-204° C. $^1$H NMR (300 MHz, CDCl$_3$): δ 2.55 (s, 3H), 7.29-7.38 (m, 1H), 7.45-7.58 (m, 3H), 7.73 (d, J=6.7 Hz, 1H), 8.20 (d, J=8.1 Hz, 1H), 14.30 (s, 1H).

<Example 65> Synthesis of 2-(3,4-difluorophenyl)-3-carboxy-7-methyl-(4H)-4-benzopyranone Through the general synthesis method of Preparation Example 1 above, a 2-hydroxy-4-methylbenzophosphorane compound (200 mg, 0.40 mmol), diisopropylethylamine (0.136 mL, 0.80 mmol, 2 eq), 3,4-difluorobenzoyl chloride (0.074 mL, 0.60 mmol, 1.5 eq), 4-(dimethylamino)pyridine (5 mg) were stirred in methylene chloride (4 mL) for 2 hours, and stirred in toluene (9 mL) for 10 hours, and then stirred in TFA (6 mL) and methylene chloride (6 mL) for 2 hours to obtain 47 mg (38%) of the final desired compound, 2-(3,4-difluorophenyl)-3-carboxy-7-methyl-(4H)-4-benzopyranone.

m.p. 202-204° C. $^1$H NMR (300 MHz, CDCl$_3$): δ 7.30-7.36 (m, 1H), 7.43 (d, J=6.9 Hz, 3H), 7.49-7.55 (m, 1H), 8.24 (d, J=8.7 Hz, 1H), 14.30 (s, 1H).

<Example 66> Synthesis of 2-(3,4-difluorophenyl)-3-carboxy-6-methyl-(4H)-4-benzopyranone Through the general synthesis method of Preparation Example 1 above, a 2-hydroxy-5-methylbenzophosphorane compound (200 mg, 0.40 mmol), diisopropylethylamine (0.136 mL, 0.80 mmol, 2 eq), 3.4-difluorobenzoyl chloride (0.074 mL, 0.60 mmol, 1.5 eq), and 4-(dimethylamino)pyridine (5 mg) were stirred in methylene chloride (4 mL) for 2 hours, and stirred in toluene (9 mL) for 10 hours, and then stirred in TFA (6 mL) and methylene chloride (6 mL) for 2 hours to obtain 70.9 mg (57.6%) of the final desired compound, 2-(3,4-difluorophenyl)-3-carboxy-6-methyl-(4H)-4-benzopyranone.

m.p. 222-223° C. $^1$H NMR (300 MHz, CDCl$_3$): δ 2.56 (s, 3H), 7.30-7.36 (m, 1H), 7.42-7.47 (m, 1H), 7.49-7.56 (m, 2H), 7.70 (dd, J=8.5, 1.8 Hz, 1H), 8.14 (s, 1H), 14.20 (s, 1H).

<Example 67> Synthesis of 2-(3,4-difluorophenyl)-3-carboxy-6-chloro-(4H)-4-benzopyranone Through the general synthesis method of Preparation Example 1 above, a 2-hydroxy-5-chlorobenzophosphorane compound (200 mg, 0.38 mmol), diisopropylethylamine (0.131 mL, 0.75 mmol, 2 eq), 3,4-difluorobenzoyl chloride (0.071 mL, 0.57 mmol, 1.5 eq), and 4-(dimethylamino)pyridine (5 mg) were stirred in methylene chloride (4 mL) for 2 hours, and stirred in toluene (9 mL) for 10 hours, and then stirred in TFA (6 mL) and methylene chloride (6 mL) for 2 hours to obtain 100.8 mg (80.0%) of the final desired compound, 2-(3,4-difluorophenyl)-3-carboxy-6-chloro-(4H)-4-benzopyranone.

m.p. 195-198° C. $^1$H NMR (300 MHz, CDCl$_3$): δ 7.31-7.37 (m, 1H), 7.43-7.47 (m, 1H), 7.50-7.61 (m, 2H), 7.83 (dd, J=8.9, 2.4 Hz, 1H), 8.32 (d, J=2.4 Hz, 1H).

<Example 68> Synthesis of 2-(4-chlorophenyl)-3-carboxy-8-methyl-(4H)-4-benzopyranone Through the general synthesis method of Preparation Example 1 above, a 2-hydroxy-3-methylbenzophosphorane compound (200 mg, 0.40 mmol), diisopropylethylamine (0.136 mL, 0.80 mmol, 2 eq), 4-chlorobenzoyl chloride (0.074 mL, 0.60 mmol, 1.5 eq), and 4-(dimethylamino)pyridine (5 mg) were stirred in methylene chloride (4 mL) for 1 hour, and stirred in toluene (9 mL) for 40 hours, and then stirred in TFA (6 mL) and methylene chloride (6 mL) for 2 hours to obtain 99 mg (81%) of the final desired compound, 2-(4-chlorophenyl)-3-carboxy-8-methyl-(4H)-4-benzopyranone.

m.p. 217-219° C. $^1$H NMR (300 MHz, CDCl$_3$): δ 2.53 (s, 3H), 7.46-7.53 (m, 3H), 7.63 (dd, J=6.7, 2.0 Hz, 2H), 7.70 (d, J=6.7 Hz, 1H), 8.18 (d, J=8.0 Hz, 1H), 14.35 (s, 1H).

<Example 69> Synthesis of 2-(4-chlorophenyl)-3-carboxy-7-methyl-(4H)-4-benzopyranone Through the general synthesis method of Preparation Example 1 above, a 2-hydroxy-4-methylbenzophosphorane compound (200 mg, 0.40 mmol), diisopropylethylamine (0.136 mL, 0.80 mmol, 2 eq), 4-chlorobenzoyl chloride (0.074 mL, 0.60 mmol, 1.5 eq), and 4-(dimethylamino)pyridine (5 mg) were stirred in methylene chloride (4 mL) for 1 hour, and stirred in toluene (9 mL) for 70 hours, and then stirred in TFA (6 mL) and methylene chloride (6 mL)

for 2 hours to obtain 105 mg (85%) of the final desired compound, 2-(4-chlorophenyl)-3-carboxy-7-methyl-(4H)-4-benzopyranone.

m.p. 220-222° C. $^1$H NMR (300 MHz, CDCl$_3$): δ 2.56 (s, 3H), 7.40 (d, J=6.7 Hz, 2H), 7.48 (dd, J=6.7, 2.0 Hz, 2H), 7.60 (dd, J=6.7, 2.0 Hz, 2H), 8.22 (d, J=8.6 Hz, 1H), 14.35 (s, 1H).

<Example 70> Synthesis of 2-(4-chlorophenyl)-3-carboxy-6-methyl-(4H)-4-benzopyranone Through the general synthesis method of Preparation Example 1 above, a 2-hydroxy-5-methylbenzophosphorane compound (200 mg, 0.40 mmol), diisopropylethylamine (0.136 mL, 0.80 mmol, 2 eq), 4-chlorobenzoyl chloride (0.074 mL, 0.60 mmol, 1.5 eq), and 4-(dimethylamino)pyridine (5 mg) were stirred in methylene chloride (4 mL) for 1 hour, and stirred in toluene (9 mL) for 60 hours, and then stirred in TFA (6 mL) and methylene chloride (6 mL) for 2 hours to obtain 57.0 mg (46.3%) of the final desired compound, 2-(4-chlorophenyl)-3-carboxy-6-methyl-(4H)-4-benzopyranone.

m.p. 212-227° C. $^1$H NMR (300 MHz, CDCl$_3$): δ 2.54 (s, 3H), 7.49 (dd, J=8.6, 2.7 Hz, 3H), 7.60 (dd, J=8.6, 1.8 Hz, 2H), 7.67 (dd, J=8.6, 2.1 Hz, 1H), 8.12 (s, 1H), 14.50 (s, 1H).

<Example 71> Synthesis of 2-(4-chlorophenyl)-3-carboxy-6-chloro-(4H)-4-benzopyranone Through the general synthesis method of Preparation Example 1 above, a 2-hydroxy-5-chlorobenzophosphorane compound (200 mg, 0.38 mmol), diisopropylethylamine (0.131 mL, 0.75 mmol, 2 eq), 4-chlorobenzoyl chloride (0.072 mL, 0.57 mmol, 1.5 eq), and 4-(dimethylamino)pyridine (5 mg) were stirred in methylene chloride (4 mL) for 1 hour, and stirred in toluene (9 mL) for 80 hours, and then stirred in TFA (6 mL) and methylene chloride (6 mL) for 2 hours to obtain 48.2 mg (38.3%) of the final desired compound, 2-(4-chlorophenyl)-3-carboxy-6-chloro-(4H)-4-benzopyranone.

m.p. 227-228° C. $^1$H NMR (300 MHz, CDCl$_3$): δ 7.50 (d, J=8.5 Hz, 2H), 7.55-7.62 (m, 3H), 7.80 (dd, J=8.9, 2.5 Hz, 1H), 8.30 (d, J=2.5 Hz, 1H), 14.20 (s, 1H).

<Example 72> Synthesis of 2-(4-chlorophenyl)-3-carboxy-6-bromo-(4H)-4-benzopyranone Through the general synthesis method of Preparation Example 1 above, a 2-hydroxy-5-bromobenzophosphorane compound (200 mg, 0.35 mmol), diisopropylethylamine (0.121 mL, 0.70 mmol, 2 eq), 4-chlorobenzoyl chloride (0.066 mL, 0.52 mmol, 1.5 eq), and 4-(dimethylamino)pyridine (5 mg) were stirred in methylene chloride (4 mL) for 1 hour, and stirred in toluene (9 mL) for 40 hours, and then stirred in TFA (6 mL) and methylene chloride (6 mL) for 2 hours to obtain 61.4 mg (46.5%) of the final desired compound, 2-(4-chlorophenyl)-3-carboxy-6-bromo-(4H)-4-benzopyranone.

m.p. 211-213° C. $^1$H NMR (300 MHz, CDCl$_3$): δ 7.47-7.50 (m, 3H), 7.73 (d, J=8.5 Hz, 2H), 7.87 (dd, J=8.8, 2.3 Hz, 1H), 8.39 (d, J=2.3 Hz, 1H).

<Example 73> Synthesis of 2-(4-chlorophenyl)-3-carboxy-(4H)-4-benzopyranone

Through the general synthesis method of Preparation Example 1 above, a 2-hydroxybenzophosphorane compound (200 mg, 0.40 mmol), diisopropylethylamine (0.140 mL, 0.80 mmol, 2 eq), 4-chlorobenzoyl chloride (0.077 mL, 0.60 mmol, 1.5 eq), and 4-(dimethylamino)pyridine (5 mg) were stirred in methylene chloride (4 mL) for 2 hours, and stirred in toluene (9 mL) for 17 hours, and then stirred in TFA (6 mL) and methylene chloride (6 mL) for 2 hours to obtain 47.1 mg (38.9%) of the final desired compound, 2-(4-chlorophenyl)-3-carboxy-(4H)-4-benzopyranone.

m.p. 212-213° C. $^1$H NMR (300 MHz, CDCl$_3$): δ 7.50 (d, J=8.6 Hz, 2H), 7.58-7.63 (m, 4H), 7.84-7.90 (m, 1H), 8.35 (dd, J=8.2, 1.7 Hz, 1H), 14.35 (s, 1H).

<Example 74> Synthesis of 2-(4-chlorophenyl)-3-carboxy-8-methoxy-(4H)-4-benzopyranone Through the general synthesis method of Preparation Example 1 above, a 2-hydroxy-3-methoxybenzophosphorane compound (200 mg, 0.38 mmol), diisopropylethylamine (0.132 mL, 0.76 mmol, 2 eq), 4-chlorobenzoyl chloride (0.072 mL, 0.57 mmol, 1.5 eq), and 4-(dimethylamino)pyridine (5 mg) were stirred in methylene chloride (4 mL) for 2 hours, and stirred in toluene (9 mL) for 20 hours, and then stirred in TFA (6 mL) and methylene chloride (6 mL) for 2 hours to obtain 30.8 mg (24.4%) of the final desired compound, 2-(4-chlorophenyl)-3-carboxy-8-methoxy-(4H)-4-benzopyranone.

m.p. 238-239° C. $^1$H NMR (300 MHz, CDCl$_3$): δ 4.02 (s, 3H), 7.34 (d, J=8.0 Hz, 1H), 7.49-7.54 (m, 3H), 7.67 (d, J=8.5 Hz, 2H), 7.88 (dd, J=8.0, 1.2 Hz, 1H), 14.30 (s, 1H).

<Experimental Example 1> Measurement of TNF-Induced Cell Death Inhibitory Activity of the Synthesized 4-benzopyranone Derivative Compound First, the addition of recombinant TNF to mouse fibroblast LM cells induces cell death, and thus, by using the same, the TNF-neutralization bioassay was constructed. In other words, LM cells were pretreated with TNF (20 ng/ml) and the compounds synthesized in the above examples at various concentrations ($5\times10^4$ cells/well), and a sensitizer actinomycin D (0.5 m/ml) was added, and cultured in a CO$_2$ incubator for 24 hours, and then the MTT assay was carried out. At this time, 10 μl of MTT (5 mg/ml stock) was added, reacted for 4 hours, and then dissolved in DMSO to measure the absorbance at 570 nm. First, the TNF cell death inhibition/neutralization action of TNF-target expected compounds at single concentration (50 or 10 μM) was measured. Second, IC50 values were determined by treating with the compounds having an excellent effect at different concentrations. The % inhibition of TNF was calculated using the following formula:

% inhibition of TNF=(OD value of a group treated with TNF and compound−OD value of TNF treated group/(OD value of TNF untreated group−OD value of TNF treated group)×100.

IC50 values were statistically analyzed using Prism 6 (GraphPad) (IC50: 50% inhibitory concentration, CC50: 50% cytotoxic concentration).

As a result, as disclosed in Tables 1 and 2 below, the cytotoxicity of TNF was inhibited up to 100% when treating with the compounds on the list together in comparison with treating with TNF only.

TABLE 1

| Compound | Concentration (μM) | TNF inhibition (%) | IC50 (μM) | CC50 (μM) |
|---|---|---|---|---|
| Example 1 | 50 | 39.1 | | |
| Example 2 | 50 | 46.6 | | |
| Example 3 | 50 | 26.3 | | |
| Example 4 | 50 | 24.6 | | |
| Example 5 | 50 | 34.4 | | |
| Example 6 | 50 | 46.0 | | |
| Example 7 | 50 | 47.0 | | |
| Example 8 | 50 | 24.3 | | |
| Example 9 | 50 | 49.2 | | |
| Example 10 | 50 | 45.6 | | |
| Example 11 | 50 | 60.6 | | |
| Example 12 | 50 | 62.5 | | |
| Example 13 | 50 | 55.9 | | |
| Example 14 | 50 | 38.8 | | |
| Example 15 | 50 | 47.5 | | |
| Example 16 | 50 | 70.2 | 16.8 | >50 |
| Example 17 | 50 | 71.0 | 2.5 | >50 |
| Example 18 | 50 | 48.6 | | |
| Example 19 | 50 | 48.3 | | |
| Example 20 | 50 | 59.0 | | |
| Example 21 | 50 | 55.2 | | |
| Example 22 | 50 | 50.4 | | |
| Example 23 | 50 | 70.1 | 2.7 | >50 |
| Example 24 | 50 | 76.3 | 2.5 | >50 |
| Example 25 | 50 | 41.0 | | |
| Example 26 | 50 | 45.1 | | |
| Example 27 | 50 | 65.2 | | |
| Example 28 | 50 | 34.9 | | |
| Example 29 | 50 | 45.7 | | |
| Example 30 | 50 | 7.4 | | |
| Example 31 | 50 | 24.8 | | |
| Example 32 | 50 | 23.6 | | |
| Example 33 | 50 | 20.7 | | |
| Example 34 | 50 | 21.7 | | |
| Example 35 | 50 | 28.1 | | |
| Example 36 | 50 | 27.0 | | |
| Example 37 | 50 | 33.4 | | |

TABLE 2

| Compound | Concentration (μM) | TNF inhibition (%) | IC50 (μM) | CC50 (μM) |
|---|---|---|---|---|
| Example 38 | 50 | 30.9 | | |
| Example 39 | 50 | 24.5 | | |
| Example 40 | 50 | 100.0 | 122.4 | >50 |
| Example 41 | 50 | 37.2 | | |
| Example 42 | 50 | 23.0 | | |
| Example 43 | 50 | 19.4 | | |
| Example 44 | 50 | 93.2 | 45.6 | >50 |
| Example 45 | 50 | 88.4 | 18.5 | 42.0 |
| Example 46 | 50 | 100.0 | 28.9 | >50 |
| Example 47 | 50 | 21.4 | | |
| Example 48 | 50 | 29.0 | | |
| Example 49 | 50 | 37.7 | | |
| Example 50 | 50 | 100.0 | 5.1 | 36.0 |
| Example 51 | 50 | 100.0 | 4.5 | 13.0 |
| Example 52 | 50 | 18.5 | | |
| Example 53 | 50 | 22.8 | | |
| Example 54 | 50 | 26.5 | | |
| Example 55 | 50 | 100.0 | 33.6 | 25.0 |
| Example 56 | 50 | 100.0 | 16.4 | 49.0 |
| Example 57 | 50 | 100.0 | 10.3 | 47.0 |
| Example 58 | 50 | 33.8 | | |
| Example 59 | 50 | 32.3 | | |
| Example 60 | 50 | 28.1 | | |
| Example 61 | 50 | 95.7 | 1.8 | >50 |
| Example 62 | 50 | 100.0 | 3.8 | 17.0 |
| Example 63 | 50 | 100.0 | 36.9 | 36.0 |
| Example 64 | 50 | 47.2 | | |
| Example 65 | 50 | 25.1 | | |
| Example 66 | 50 | 37.0 | | |
| Example 67 | 50 | 100.0 | 3.9 | 21.0 |
| Example 68 | 50 | 15.8 | | |
| Example 69 | 50 | 14.6 | | |
| Example 70 | 50 | 28.9 | | |
| Example 71 | 50 | 97.9 | 3.3 | 36.0 |
| Example 72 | 50 | 100.0 | 20.8 | >50 |
| Example 73 | 50 | 42.0 | | |
| Example 74 | 50 | 79.0 | 52.5 | >50 |

Among these compounds, the compound of Example 61 had the lowest IC50 value and cytotoxicity, so that the action mechanism and activity of this compound were studied more in depth. FIG. 1 shows the TNF-inhibiting levels of representative compounds including the compound of Example 61 depending on concentration.

<Experimental Example 22> Measurement of TNF Direct Binding and TNF-Etanercept Binding Inhibitory Activity of 4-benzopyranone Derivative Compounds (1) Measurement of Real-Time Binding of 4-benzopyranone Derivative Compound to TNF Using SPR Analysis Method The binding kinetics of TNF and 4-benzopyranone derivative compounds was measured by Surface Plasmon Resonance (SPR) method. First, based on the results of pH scouting (10 mM acetate buffer, pH 4.0, 4.5, 5.0, and 5.5), the appropriate buffer pH was determined, and then the recombinant TNF was immobilized on the CM5 chip (4000-5000 RU). In order to correct an effect of DMSO, a solvent correction standard was then prepared, and DMSO was added to the HBS-EP+ buffer (GE) in an amount of 5%. Then, the 4-benzopyranone derivative compounds were prepared depending on concentration, flowed into the chip (20 μl/min, 500 s), and dissolved (500 s), and the results of sensorgram were analyzed by a dedicated program to determine the affinity value ($K_D$). At this time, the running buffer was HBS-EP+ buffer (GE), the regeneration buffer was 10 mM glycine (pH 2.5), and Biacore T200 (GE) was used as an analyzer.

Figure 2A:
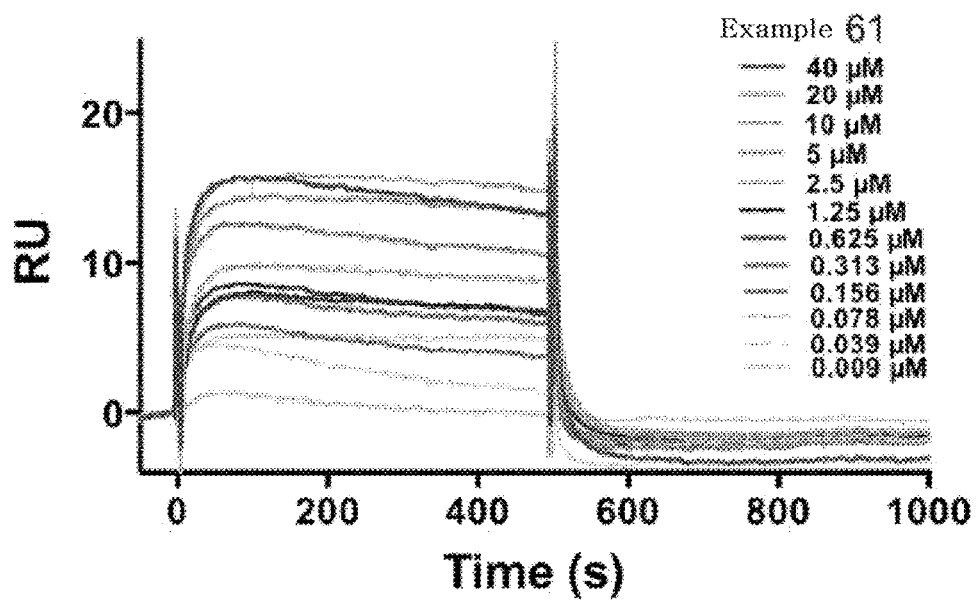
FIG. 2 shows the competitive inhibitory activity against TNF direct binding and TNF-etanercept binding of the compounds of the present invention ((a): the results of confirming the binding of the compound of Example 61 with TNF bound to chips by the surface plasmon resonance analysis method (Biacore T200), (b): the results of measuring the binding affinity ($K_D$) of the compound of Example 61 with TNF bound to chips, (c): the results of measuring whether the compound binds to a TNF receptor, etanercept by the surface plasmon resonance analysis method, (d) the results of measuring the binding affinity ($K_D$) of the compound of Example 30 for TNF which has a weak TNF-inhibiting efficacy as a control group, and (e): the results of confirming the inhibiting ability of the compound of Example 61 on the TNF-etanercept binding by the surface plasmon resonance analysis method).
Figure 2B:
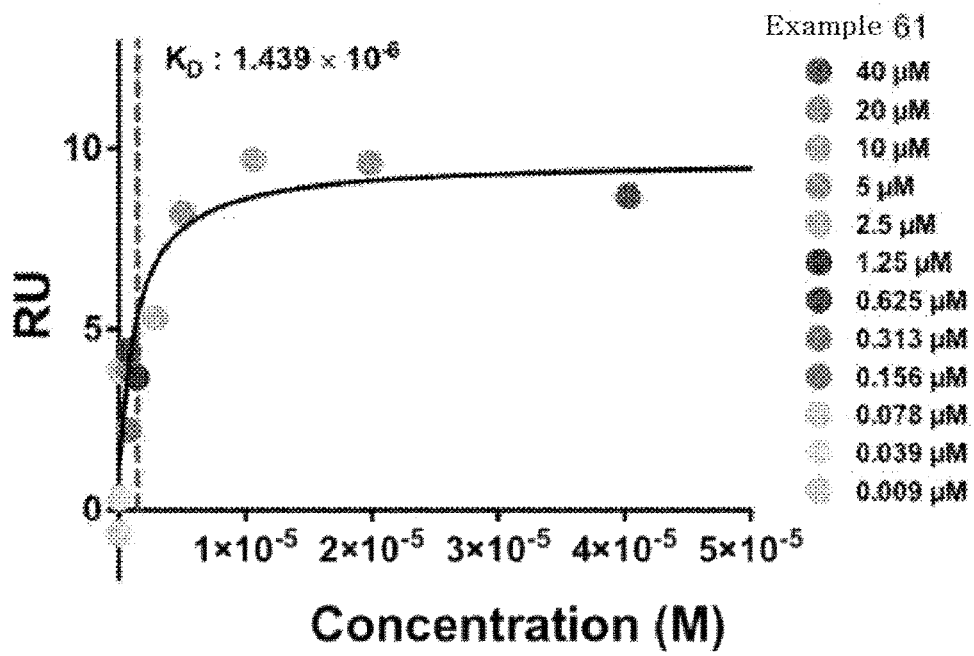
Figure 2C:
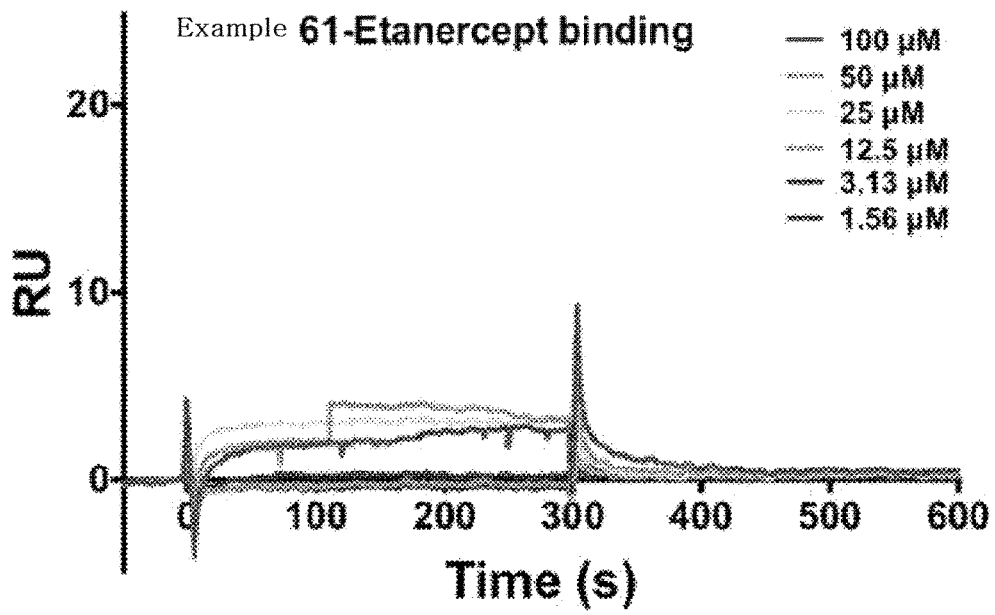
Figure 2D:
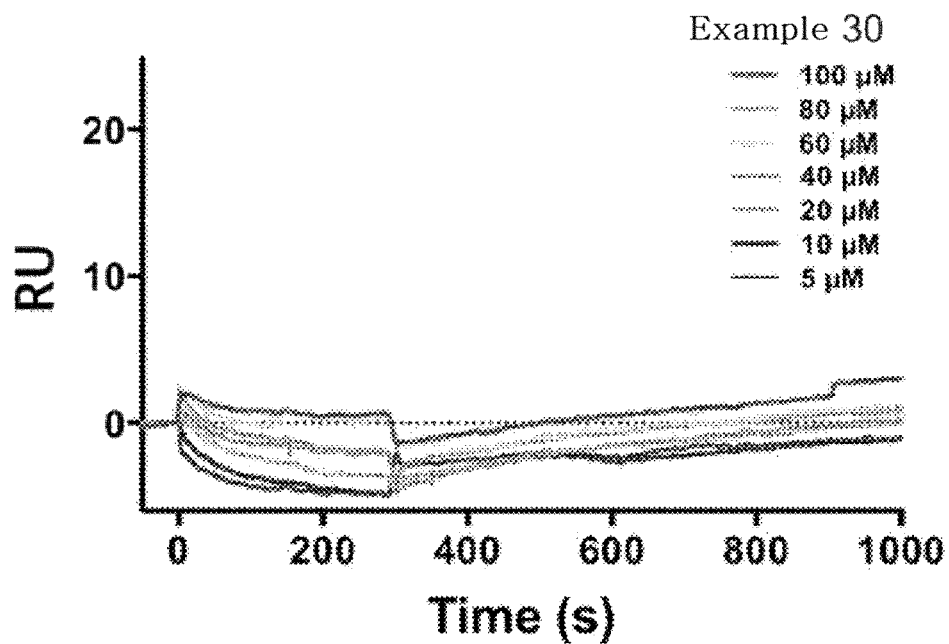

As a result, as shown in FIG. 2, the TNF direct binding of the compound of Example 61 was measured using SPR assay, and the binding affinity ($K_D$) was $1.439 \times 10^{-6}$ (M) (FIGS. 2a and 2b). It was confirmed that the compound of Example 61 did not bind to etanercept (FIG. 2c), and the compound of Example 30, which had almost no TNF neutralization effect (Table 1, 7.4% inhibition), did not bind to TNF (FIG. 2d).

(2) Measurement of TNF-Etanercept Binding Inhibitory Activity of 4-benzopyranone Derivative Compounds Using SPR Analysis Method The competition of binding of TNF-inhibiting biopharmaceutical etanercept and the derivative compounds to TNF was measured by SPR assay. Based on the results of pH scouting (10 mM acetate buffer, pH 4.0, 4.5, 5.0, and 5.5), the appropriate buffer pH was determined, and then the recombinant TNF was immobilized on the CM5 chip (4000-5000 RU). In order to correct an effect of DMSO, a solvent correction standard was then prepared, and DMSO was added to the PBST buffer (1×PBS, pH 7.4, 0.05% Tween 20, 0.01% Triton X-100, 5% DMSO) in an amount of 5%. Then, Etanercept alone or in combination with the compounds was flowed into the chip (20 μl/min, 300 s) and dissolved (700 s), and the results of sensorgram were analyzed by a dedicated program. The changes in the RU value of the compound mixture samples were observed with comparison with the biopharmaceuticals alone control group. At this time, the running buffer was PBST buffer, the regeneration buffer was 10 mM glycine (pH 2.5), and the instrument was Biacore T200 (GE).

Figure 2E:
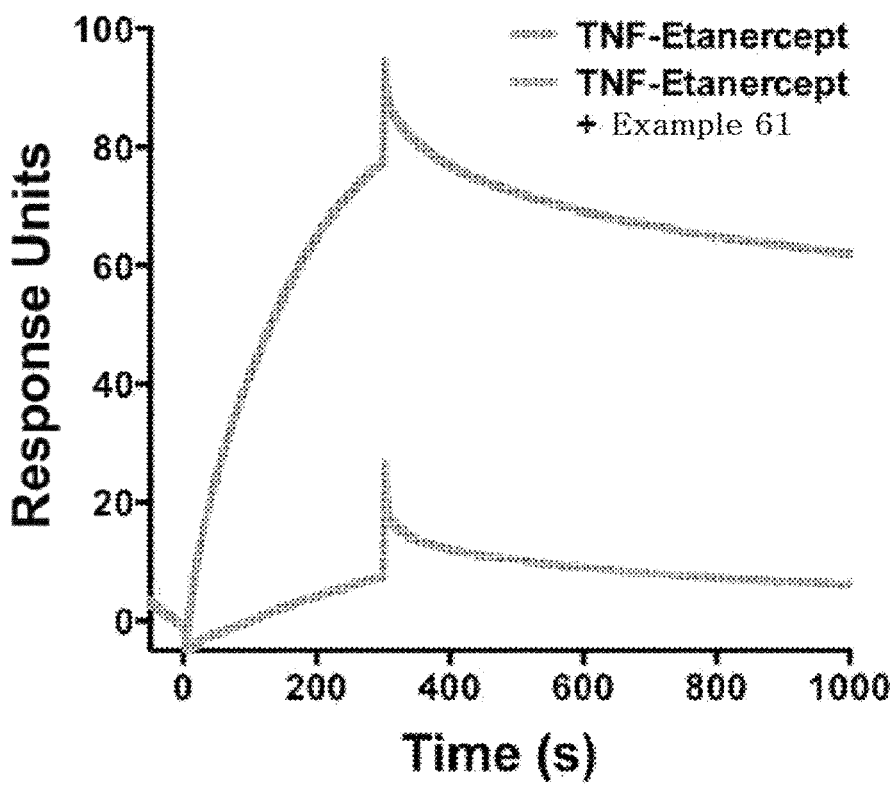

As a result, as shown in FIG. 2e, the compound of Example 61 significantly inhibited the TNF-etanercept binding. Thus, it was proved that the compound and etanercept competed with each other against TNF, and the compound inhibited the binding of TNF to TNF receptor (etanercept) by binding to TNF.

<Experimental Example 3> Analysis of TNF-Cell Binding and TNF-Cell Signaling Inhibitory Activity by 4-benzopyranone Derivative Compounds (1) Measurement of Inhibitory Activity Against Binding to Raw 264.7 Cell of TNF by 4-benzopyranone Derivative Compound Using Flow Cytometry Analysis Method First, macrophage Raw 264.7 cells were prepared ($4 \times 10^6$ cells/ml), and the biotinylated TNF alone or in combination with the 4-benzopyranone derivative compound (800, 200, 5 μM) was added to the cells and reacted (30 min, 4° C.). 10 μl of avidin-FITC reagent was then added and reacted in the dark (30 min, 4° C.). After washing with RDF1 buffer, FACS analysis was carried out (BD Canto). Human TNF-alpha Biotinylated Fluorokine Flow Cytometry Kit (Cat #: NFTAO) of R&D Systems was used in the experiment.

Figure 3A:
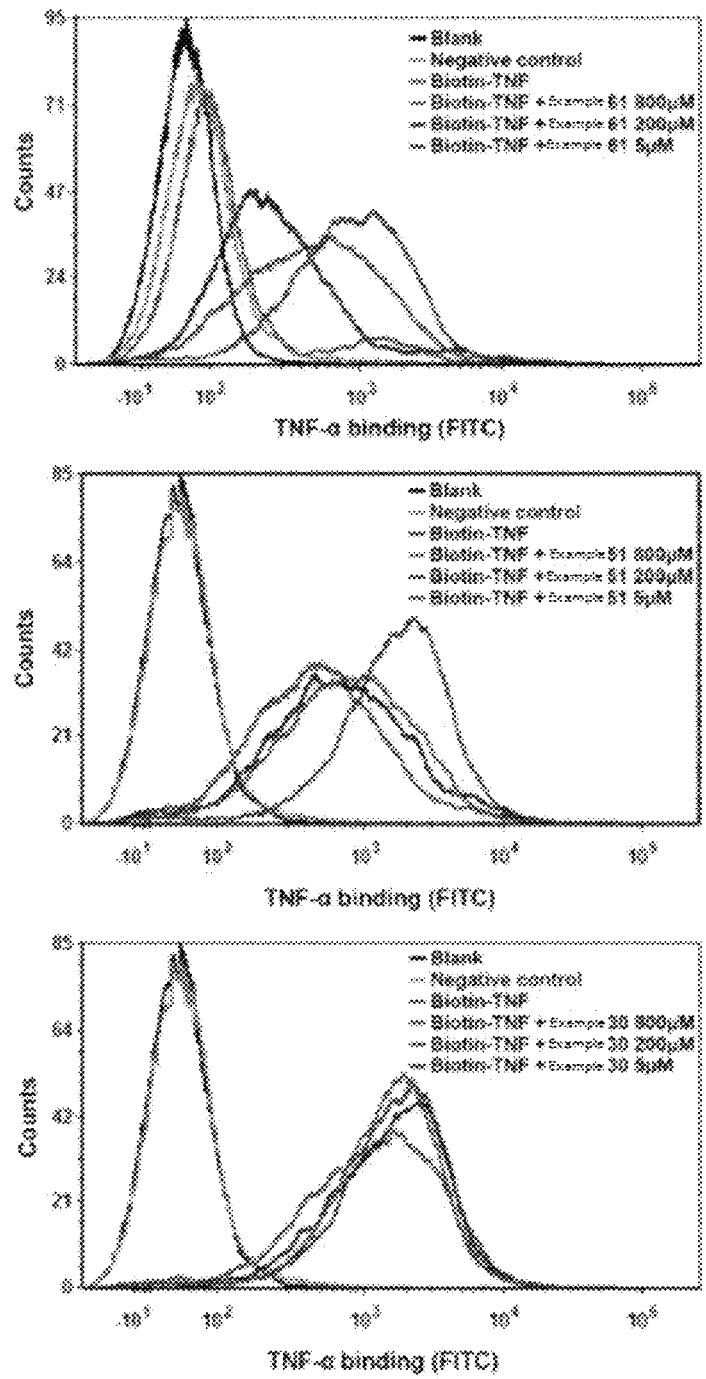
FIG. 3 shows (a) the inhibitory activity against the binding between TNF-cell of the TNF-inhibiting compounds, and (b) the inhibitory activity against a TNF-induced signaling of the compound of Example 61 according to one example of the present invention.

As a result, as shown in FIG. 3a, the compound of Example 61 having the lowest IC50 value (Table 2, 1.8 μM) decreased the target cell binding of TNF to the basal level in a concentration-dependent manner, and the compound of Example 51 having the relatively high IC50 value (Table 2, 4.5 μM) exhibited the moderate inhibitory activity against the TNF-cell binding, and the compound of Example 30 having almost no inhibitory activity against the TNF toxicity (Table 1) did not inhibit the cell binding of TNF at all. Based on the above, it was found that there is a close correlation between the TNF cytotoxicity inhibitory effect and the TNF-cell binding inhibitory effect.

(2) Measurement of Inhibitory Activity Against LM Cell Signaling of TNF by 4-benzopyranone Derivative Compounds Using Western Blot Analysis Method First, LM cells was treated with TNF alone (50 ng/ml) or a mixture of TNF and the compound of Example 61 (0, 10, 25, 50 μM) for 1 hour, and then the cells were washed and prepared. After the cytoplasmic fraction and nuclear fraction were separated/obtained using NE-PER nuclear and cytoplasmic extraction reagents (Thermo Scientific, cat #78833), NF-kB p65 protein was detected by SDS-PAGE and Western Blot. Anti-NF-κB p65 rabbit monoclonal antibody (Cell Signaling Technology, cat #D14E12) was used as a primary antibody, and goat anti-rabbit HRP-conjugated antibody (Invitrogen, cat #656120) was used as a secondary antibody. As a Western Blot control protein (housekeeping protein), GAPDH was used in the cytoplasmic fraction, and Lamin B1 was used in the nuclear fraction. Anti-GAPDH mouse monoclonal antibody (GenScript, cat #A01622) was used as a primary antibody of GAPDH, and goat anti-mouse HRP-conjugated antibody (BETHYLlaboratories, cat #A90-116P) was used as a secondary antibody. Anti-Lamin-B1 rabbit monoclonal antibody (Cell Signaling Technology, cat #12586S) was used as a primary antibody of Lamin B1, and anti-rabbit HRP-conjugated antibody (Invitrogen, cat #656120) was used as a secondary antibody.

Figure 3B:
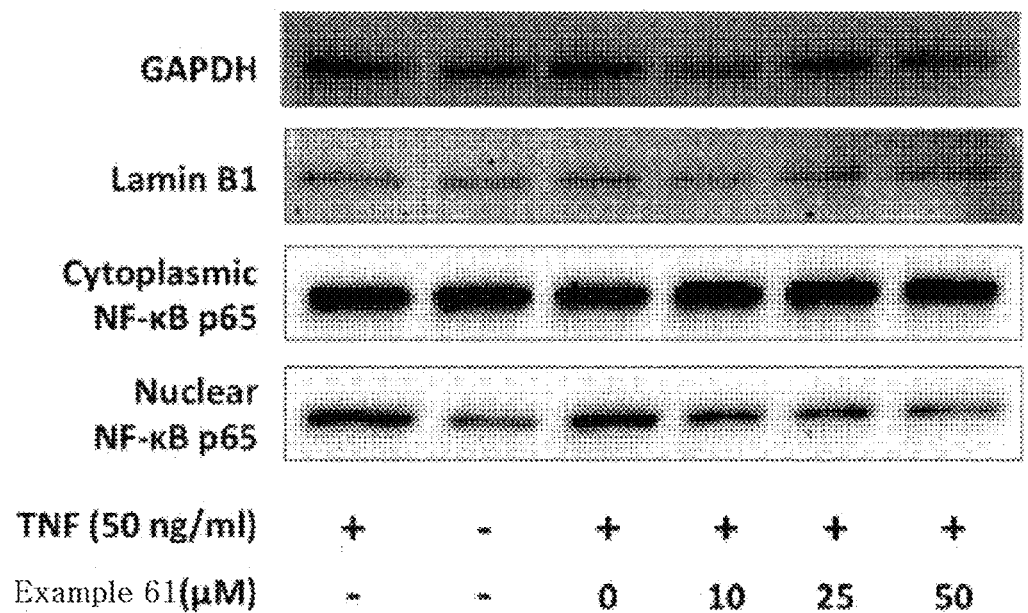

As a result, as shown in FIG. 3b, it was found that the migration of NF-kB from the cytoplasm to the nucleus activated by the TNF treatment was almost completely inhibited by the treatment of the compound of Example 61 at about 25 μM.

Considering all the results of FIG. 3, the compound of Example 61 also seems to inhibit the cell signaling of TNF by intrinsically blocking the cell binding of TNF.

<Experimental Example 4> Analysis of Therapeutic Effect on Sepsis by 4-benzopyranone Derivative Compounds (1) In Vivo TNF Neutralization Assay (TNF-Induced Sepsis)

Treatment with TNF and a sensitizer D-galactosamine in an in vivo mouse model leads to death from acute liver failure. Thus, the compound of Example 61 (3.3 mpk or 16.5 mpk) was orally administered to BALB/c mice, and after 30 minutes, the mice were IP treated with the mixture of D-galactosamine (21 mg/mouse) and TNF (0.3 μg/mouse). Survival rates were observed and recorded every 3 hours up to 24 hours, and statistically analyzed by log-rank (Mantel-Cox) test using Prism 6 (GraphPad) (N=13/group, P<0.005, *P<0.001). mpk, mg/kg). This confirmed that the in vivo neutralization activity of the compounds binding to TNF in a TNF-induced lethality model.

Figure 4A:
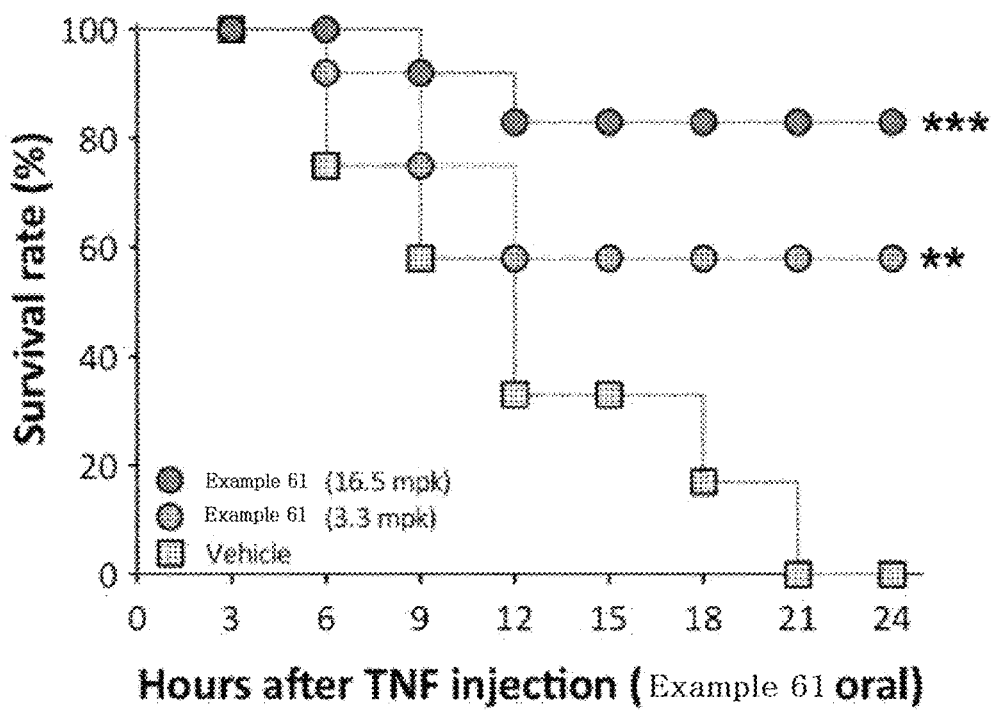
FIG. 4 shows the sepsis therapeutic effect of the TNF-inhibiting compound according to one example of the present invention ((a): the results of measuring the in vivo TNF-inhibitory activity of the compound of Example 61 in a TNF-induced sepsis lethality model, and (b): the results of experimenting the in vivo efficacy on the administration of a TNF-inhibiting compound, the compound of Example 61 in combination with an IL-6-inhibiting compound, LMT-28 using the lipopolysaccharide (LPS)-induced sepsis model).

As a result, as shown in FIG. 4a, it was found that the death of mice due to acute hepatotoxicity induced by D-galactosamine and TNF was inhibited by oral administration (PO) of the compound of Example 61 (3.3, 16.5 mpk) in a concentration-dependent manner.

(2) Lipopolysaccharide (LPS)-Induced Sepsis Model

The sepsis mouse model was induced by the intraperitoneal infusion of LPS (45 mg/kg; Sigma, *E. coli* O55:B5). The mouse survival experiment was carried out by observing the survival rates every 24 hours up to 3 days after co-administering the compound of Example 61 (50 mg/kg) and LMT-28 (50 mg/kg) immediately after the infusion of LPS.

Figure 4B:
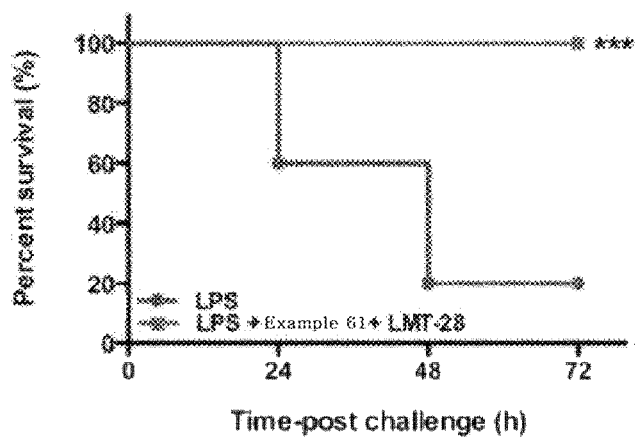

As a result, as shown in FIG. 4b, 100% survival rate was shown in the group treated with the compound of Example 61 and LMT-28 in comparison with the LPS alone treated group in which the survival rate was 20% after 72 hours (N=5/group, ***P<0.001).

<Experimental Example 5> Analysis of Prophylactic/Therapeutic Effect on Rheumatoid Arthritis by 4-benzopyranone Derivative Compounds (1) Prophylactic Effect on Rheumatoid Arthritis (TNF-Overexpressing Mouse Model)

The TNF-overexpressing C57BL/6 mouse is a gene recombinant mouse, and a model in which human TNF is overexpressed and arthritis is induced as the age of the mouse becomes higher. The compound of Example 61 (3.3 mpk or 33 mpk) was orally administered to the TNF-overexpressing mice from Week 8 to Week 24, three times a week, and the pathology was measured and recorded from Week 7 to Week 24. The pathology score was measured as 1=erythema or bent foot, 2=bent foot and weak swelling, 3=bent foot and moderate swelling, 4=ankle bending and weak swelling, 5=ankle bending and severe swelling (N=4/group, *P<0.01, P<0.005, *P<0.001).

Figure 5A:
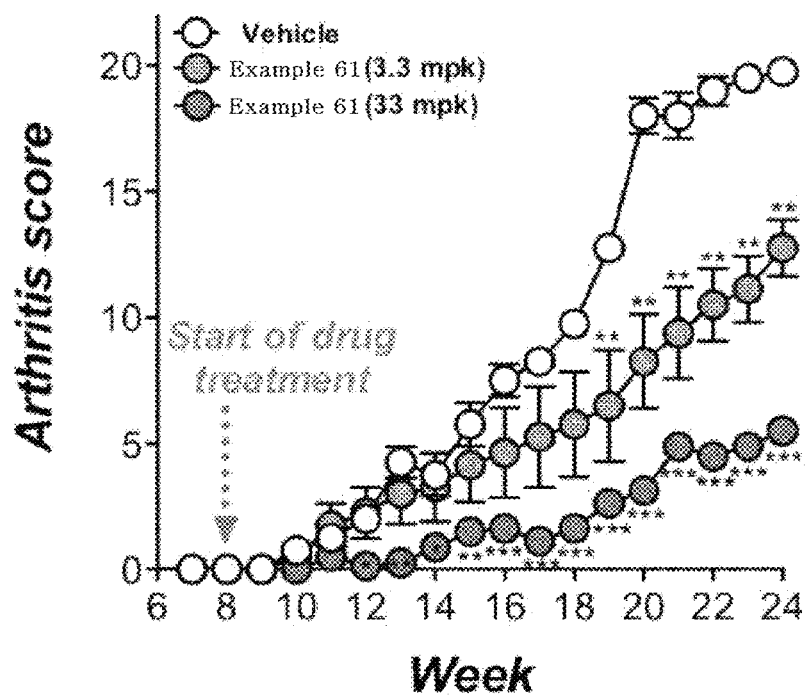
FIG. 5 shows the effect of preventing or treating rheumatoid arthritis of the TNF-inhibiting compound according to one example of the present invention ((a): the results of confirming the effect of preventing rheumatoid arthritis of the compound of Example 61 in a TNF-overexpressing mouse model, (b): the results of confirming the effect of treating rheumatoid arthritis of the compound of Example 61 in a TNF-overexpressing mouse model, and (c): the results of confirming the effect of treating rheumatoid arthritis of the compound of Example 61 in a CIA mouse model).

As a result, as shown in FIG. 5a, the TNF-inhibiting compounds inhibited TNF-induced rheumatoid arthritis in a concentration-dependent manner and showed a significant efficacy even at a low dose of 3.3 mpk. At the dose of 33 mpk, a remarkable prophylactic effect on rheumatoid arthritis was observed in comparison with the negative control group.

(2) Therapeutic Effect on Rheumatoid Arthritis (TNF-Overexpressing Mouse Model)

First, until the mean level of arthritis of TNF-overexpressing mice reached 8, the mice were raised. As such, etanercept (4.5 mpk), adalimumab (1.2 mpk), the compound of Example 61 (25 mpk, 50 mpk, or 100 mpk) were orally administered to the mice with rheumatoid arthritis from Week 15 to Week 23, three times a week, and the pathology was measured and recorded from Week 7 to Week 23 (N=5 to 6/group, *P<0.01, P<0.005, *P<0.001).

Figure 5B:
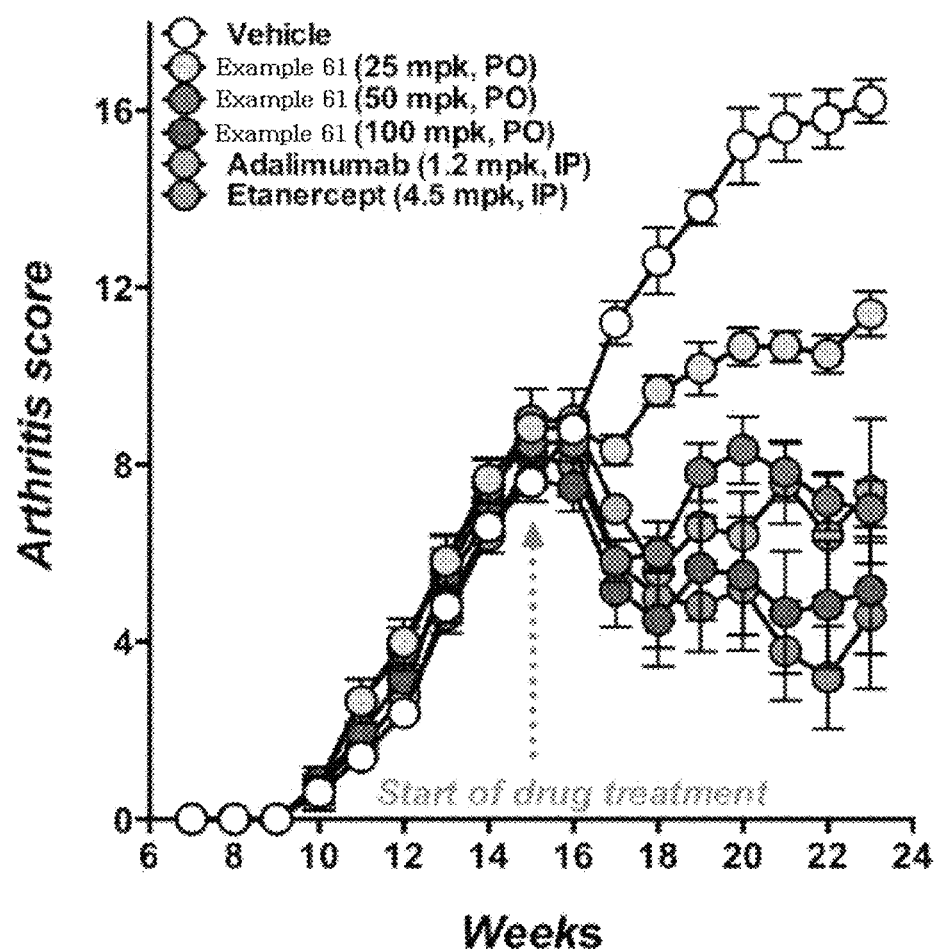

As a result, as shown in FIG. 5b, the TNF-inhibiting compounds showed a therapeutic efficacy on rheumatoid arthritis already induced by TNF in a concentration-dependent manner. At all doses of 25, 50, and 100 mpk, a remarkable therapeutic effect on rheumatoid arthritis was observed in comparison with the negative control group. When the compound of Example 61 was orally administered at the doses of 50 and 100 mpk, a non-inferior effect was observed even in comparison with adalimumab and etanercept, which are each commercially available injectable biopharmaceuticals.

(3) Synergistic Therapeutic Effect on Rheumatoid Arthritis when Administered in Combination with Tofacitinib (CIA Mouse Model)

The CIA mouse model is a model in which arthritis is induced by collagen in DBA/1 mice. Thus, a 1:1 mixture of collagen type 2 and CFA was intradermally (ID) injected into the base of the tail of 8-week old DBA/1 mice. Two weeks after the primary immunization, a 1:1 mixture of collagen type 2 and IFA was intradermally (ID) injected into the base of the tail. After the second immunization, the pathology was measured twice a week, and the groups were divided equally so that the mean of the pathology of each group was 4 points. From Day 35 after the primary immunization, etanercept (4.5 mpk), adalimumab (1.2 mpk), the compound of Example 61 (25 mpk, 50 mpk, or 100 mpk) were orally administered three times a week, and the pathology was measured and recorded. The pathology score was measured as 1=inflammation and swelling of one toe, 2=inflammation of one or more toes or weak swelling of the whole sole of the foot, 3=severe swelling of the whole sole of the foot and swelling of ankle, 4=very severe inflammation and swelling of the whole foot or the bending and stiffness of foot (N=7 to 9/group, *P<0.01, P<0.005, *P<0.001).

Figure 5C:
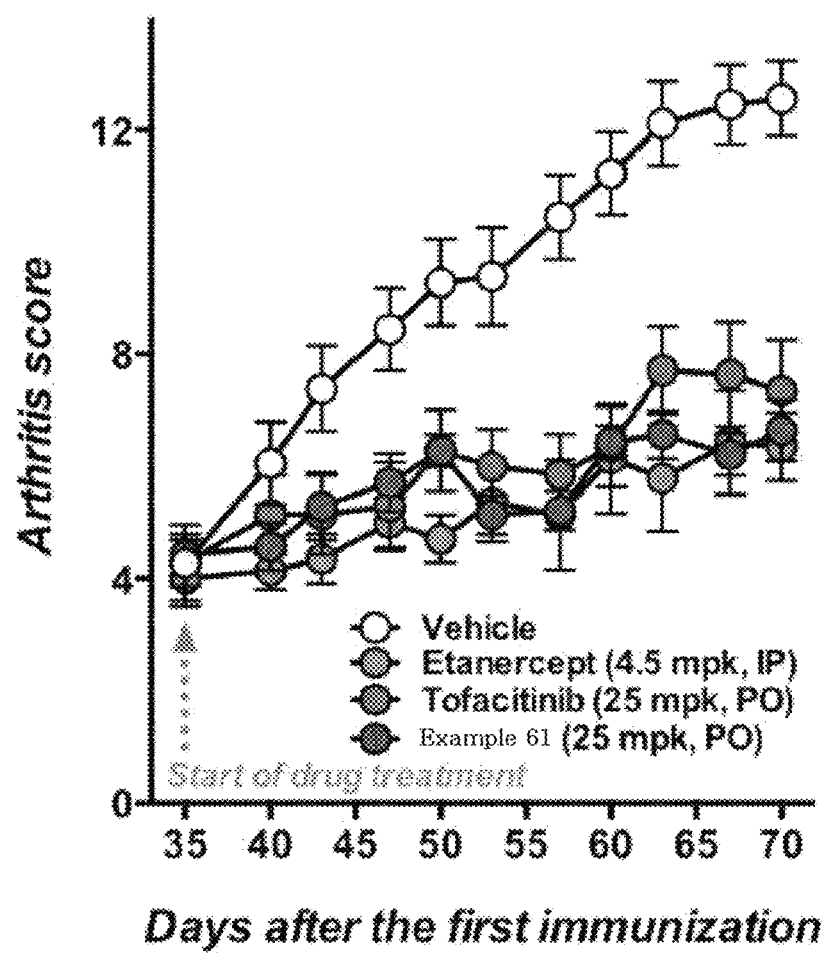

As a result, as shown in FIG. 5c, the TNF-inhibiting compounds showed remarkable therapeutic efficacy on rheumatoid arthritis already induced by the infusion of collagen. At all doses of 25, 50, and 100 mpk, a remarkable therapeutic effect on rheumatoid arthritis was observed in comparison with the negative control group. The compound of Example 61 (25 mpk) showed considerably similar efficacy to tofacitinib (25 mpk), which is a commercially available oral JAK inhibitor, and showed a non-inferior effect even in comparison with etanercept, which is an injectable biopharmaceuticals.

(4) Synergistic Therapeutic Effect on Rheumatoid Arthritis when Administered in Combination with Methotrexate (MTX) (CIA Mouse Model)

A 1:1 mixture of collagen type 2 and CFA was intradermally (ID) injected into the base of the tail of DBA/1 mice. Two weeks after the primary immunization, a 1:1 mixture of bovine collagen type 2 and IFA (incomplete Freund's adjuvant) was intradermally (ID) injected into the base of the tail to prepare the rheumatoid arthritis animal model. The thus prepared mice were divided into three groups, i.e., a positive control group (MTX 5 mpk treated group: 10 mice), a group treated with the compound of Example 61 alone (10 mpk treated group: 9 mice), a group treated with MTX and the compound of Example 61 (each 5 mpk and 10 mpk; 9 mice), and a group treated with vehicle (a group treated with 0.05% CMC diluted in distilled water; 15 mice). At the time of the first symptom (Day 25 after the primary immunization), each of the drug was intraperitoneally or orally administered three times a week (license #2016-018-02), and the compound of Example 61 was orally administered once a day.

The severity of arthritis was determined by ascertaining the mean score of arthritis according to the following standard score in the forefoot and hindfoot twice a week from Day 0 to Day 73 after the primary immunization: 0=normal foot, 1=inflammation and swelling of one toe, 2=inflammation and swelling of more than one toe, but not all of the toes have inflammation and swelling, or weak swelling of all toes, 3=inflammation and swelling of all toes, and 4=severe inflammation and swelling or occlusion of foot.

Figure 8:
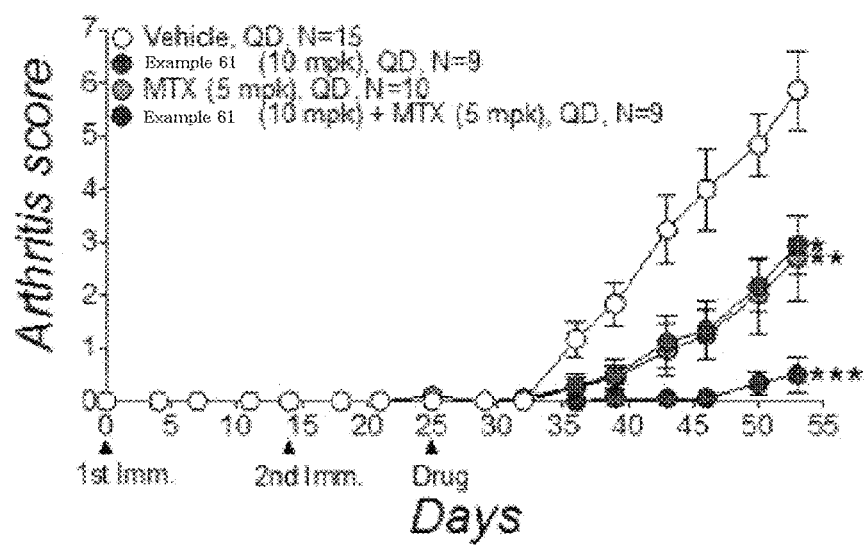
FIG. 8 shows the results of confirming the synergistic therapeutic effect when co-administering the compound of Example 61 and methotrexate (MTX) in an animal model of rheumatoid arthritis.

As a result, as shown in FIG. 8, even when treating with only the compound of Example 61 or MTX alone, the therapeutic effect on arthritis was shown. However, when the two ingredients are used together, the remarkably excellent therapeutic effect on arthritis was shown. Thus, it was confirmed that a remarkable synergistic effect was shown.

<Experimental Example 6> Analysis of Therapeutic Effect on Inflammatory Bowel Disease (IBD) by 4-benzopyranone Derivative Compounds Inflammatory bowel disease was induced by the oral treatment with dextran sodium sulfate (DSS) to mice. The pathology was induced by DSS (2.5%, 6 days) in 7-week old C57BL/6 mice. At the same time, the compound of Example 61 (100 mpk) and metformin (100 mpk) were orally co-administered. After 9 days, the colon length of each treated group was measured, and the therapeutic effect of drugs on inflammatory bowel disease was statistically analyzed (N=5/group, *P<0.05, mean±SEM).

Figure 6:
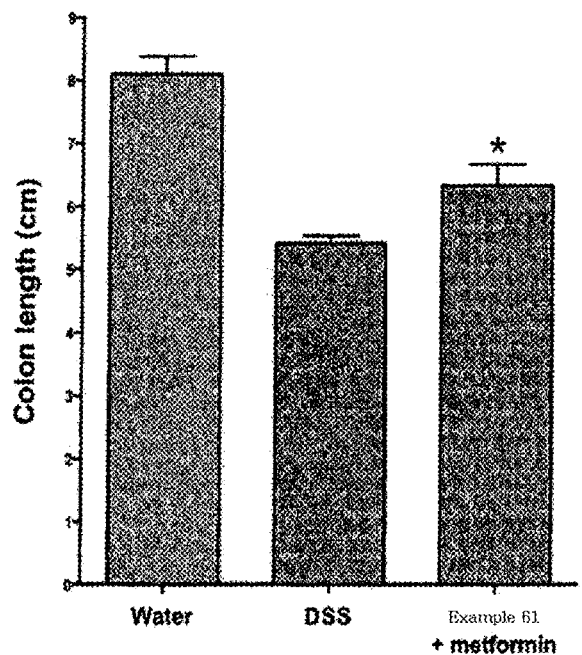
FIG. 6 shows the therapeutic effect when co-administering the compounds in an animal model of dextran sulfate sodium (DSS) induced inflammatory bowel disease.

As a result, as shown in FIG. 6, after the TNF inhibitory efficacy was confirmed in experiments in vitro/in vivo using the compound of Example 61, the efficacy against inflammatory bowel disease was analyzed. As a result, it was confirmed that the decrease of the colon length by DSS was significantly inhibited when co-administering the compound of Example 61 and metformin.

<Experimental Example 7> Analysis of Protective Effect on Sepsis-Induced Acute Kidney Injury by 4-benzopyranone Derivative Compounds The mice (male, C57/BL6, 12-14-week old, 25-30 g, N=5) were subjected to cecal ligation and puncture (CLP) or a sham procedure, and then were kept for 48 hours. The compound of Example 61 (50 mpk) was IP infused immediately after the CLP procedure. After 48 hours, in order to measure renal function, the amount of blood urea nitrogen (BUN) and creatinine in serum was analyzed.

Figure 7:
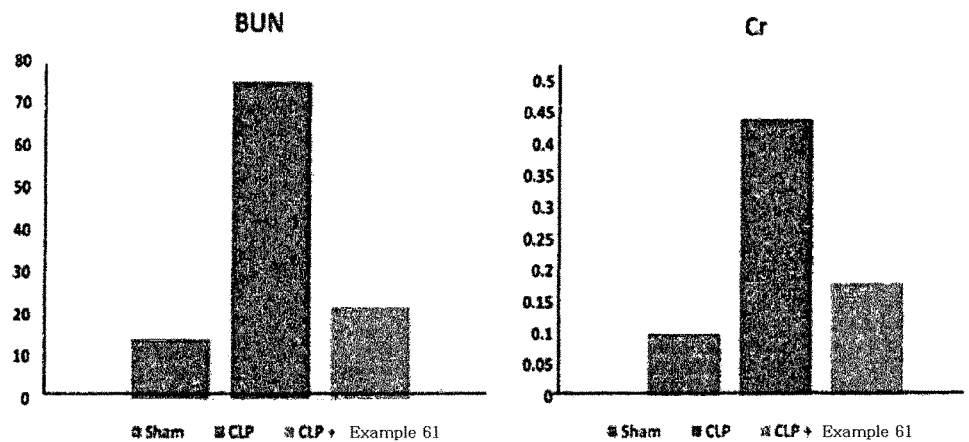
FIG. 7 shows the effect of protecting acute kidney injury of the compounds in an animal model of cecal ligation and puncture (CLP)-induced sepsis.

As a result, as shown in FIG. 7, the incidence of acute kidney injury (AKI) at 48 hours after the CLP procedure was about 75%, whereas in case of the compound treated group, there was no significant increase or there was a slight increase in the kidney injury marker in all of the treated groups.

While the present invention has been particularly described with reference to specific embodiments thereof, it will be apparent to those skilled in the art that such specific embodiments are merely preferred embodiments and that the scope of the present invention is not limited thereby. That is, the practical scope of the present invention is defined by the appended claims and equivalents thereof.

The invention claimed is:

1. A method for treating a TNF overexpression disease, comprising administering a pharmaceutically effective amount of a composition to an animal in need thereof, wherein the composition comprises a 4-benzopyranone derivative represented by Formula 1 or its pharmaceutically acceptable salt as an active ingredient, and inhibits a TNF activity by being directly bound to tumor necrosis factor (TNF):

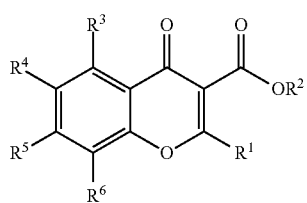

(1)

in which, $R^1$ is furanyl, thiophenyl, or substituted phenyl represented by

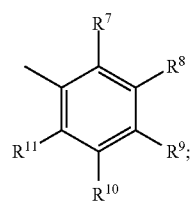

$R^7$, $R^8$, $R^9$, $R^{10}$, and $R^{11}$ are each independently hydrogen, chloro, bromo, fluoro, or methoxy;

$R^2$ is hydrogen or lower alkyl of (C1-C4); and $R^3$, $R^4$, $R^5$, and $R^6$ are each independently hydrogen, halogen, or (C1-C4)alkoxy, and the TNF overexpression disease is selected from the group consisting of rheumatoid arthritis, juvenile rheumatoid arthritis, inflammatory bowel disease, Crohn's disease, ulcerative colitis, psoriasis, plaque psoriasis, juvenile plaque psoriasis, psoriatic arthritis, polyarticular juvenile idiopathic arthritis, Behcet's enteritis, ankylosing spondylitis, axial spondyloarthritis, juvenile enthesitis-related arthritis, osteoarthritis, polymyalgia rheumatica, multiple sclerosis, systemic lupus erythematosus, asthma, Sjogren's syndrome, pneumonia, chronic obstructive pulmonary disease, sarcoidosis, granuloma annulare, Wegener's granulomatosis, arteriosclerosis, vasculitis, heart failure, myocardial infarction, kidney injury, nephritis, graft versus host disease, dementia, Alzheimer's disease, Parkinson's disease, pain, uveitis, Behcet's disease, hidradenitis suppurativa, *Pityriasis rubra pilaris*, necrobiosis lipoidica diabeticorum, pyoderma gangrenosum, Sweet's syndrome, subcorneal pustular dermatosis, scleroderma, neutrophilic dermatitis, dermatomyositis, sepsis, and septic shock.

2. The method of claim 1, wherein the animal is a human.

3. The method of claim 1, wherein the animal is not a human.

4. A method for treating a TNF overexpression disease, comprising administering a pharmaceutically effective amount of a composition to an animal in need thereof, wherein the composition comprises a 4-benzopyranone derivative selected from the group consisting of 2-(2-chlorophenyl)-3-carboxy-7-methoxy-(4H)-4-benzopyranone; 2-(2-chlorophenyl)-3-carboxy-(4H)-4-benzopyranone; 2-(2-furanyl)-3-carboxy-(4H)-4-benzopyranone; 2-(2-furanyl)-3-carboxy-8-methoxy-(4H)-4-benzopyranone; 2-(2-furanyl)-3-carboxy-7-methoxy-(4H)-4-benzopyranone; 2-(2-furanyl)-3-carboxy-6-methoxy-(4H)-4-benzopyranone; 2-(2-furanyl)-3-carboxy-8-methyl-(4H)-4-benzopyranone; 2-(2-furanyl)-3-carboxy-7-methyl-(4H)-4-benzopyranone; 2-(2-furanyl)-3-carboxy-6-methyl-(4H)-4-benzopyranone; 2-(2-furanyl)-3-carboxy-7-chloro-(4H)-4-benzopyranone; 2-(2-furanyl)-3-carboxy-6-chloro-(4H)-4-benzopyranone; 2-(2-furanyl)-3-carboxy-6-bromo-(4H)-4-benzopyranone; 2-(3-methylphenyl)-3-carboxy-(4H)-4-benzopyranone; 2-(3-methylphenyl)-3-carboxy-8-methoxy-(4H)-4-benzopyranone; 2-(3-methylphenyl)-3-carboxy-7-methoxy-(4H)-4-benzopyranone; 2-(3-methylphenyl)-3-carboxy-6-methoxy-(4H)-4-benzopyranone; 2-(3-methylphenyl)-3-carboxy-8-methyl-(4H)-4-benzopyranone; 2-(3-methylphenyl)-3-carboxy-7-methyl-(4H)-4-benzopyranone; 2-(3-methylphenyl)-3-carboxy-6-methyl-(4H)-4-benzopyranone; 2-(3-methylphenyl)-3-carboxy-7-chloro-(4H)-4-benzopyranone; 2-(3-methylphenyl)-3-carboxy-6-chloro-(4H)-4-benzopyranone; 2-(3-methylphenyl)-3-carboxy-6-bromo-(4H)-4-benzopyranone; 2-(2-thiophenyl)-3-carboxy-8-methoxy-(4H)-4-benzopyranone; 2-(2-thiophenyl)-3-carboxy-7-methoxy-(4H)-4-benzopyranone; 2-(2-thiophenyl)-3-carboxy-6-methoxy-(4H)-4-benzopyranone; 2-(2-thiophenyl)-3-carboxy-(4H)-4-benzopyranone; 2-(2-thiophenyl)-3-carboxy-8-methyl-(4H)-4-benzopyranone; 2-(2-thiophenyl)-3-carboxy-7-methyl-(4H)-4-benzopyranone; 2-(2-thiophenyl)-3-carboxy-6-methyl-(4H)-4-benzopyranone; 2-(2-thiophenyl)-3-carboxy-7-chloro-(4H)-4-benzopyranone; 2-(2-thiophenyl)-3-carboxy-6-chloro-(4H)-4-benzopyranone; 2-(2-thiophenyl)-3-carboxy-6-bromo- (4H)-4-benzopyranone; 2-(3,4-dimethoxyphenyl)-3-carboxy-(4H)-4-benzopyranone; 2-(3,4-dimethoxyphenyl)-3-carboxy-8-methyl-(4H)-4-benzopyranone; 2-(3,4-dimethoxyphenyl)-3-carboxy-7-methyl-(4H)-4-benzopyranone; 2-(3,4-dimethoxyphenyl)-3-carboxy-6-methyl-(4H)-4-benzopyranone; 2-(3,4-dimethoxyphenyl)-3-carboxy-7-chloro-(4H)-4-benzopyranone; 2-(3,4-dimethoxyphenyl)-3-carboxy-6-chloro-(4H)-4-benzopyranone; 2-(3,4-dimethoxyphenyl)-3-carboxy-6-bromo-(4H)-4-benzopyranone; 2-(3,4-dimethoxyphenyl)-3-carboxy-7-methoxy-(4H)-4-benzopyranone; 2-(3,4-dimethoxyphenyl)-3-carboxy-8-methoxy-(4H)-4-benzopyranone; 2-(3-fluorophenyl)-3-carboxy-(4H)-4-benzopyranone; 2-(3-fluorophenyl)-3-carboxy-8-methyl-(4H)-4-benzopyranone; 2-(3-fluorophenyl)-3-carboxy-7-methyl-(4H)-4-benzopyranone; 2-(3-fluorophenyl)-3-carboxy-6-methyl-(4H)-4-benzopyranone; 2-(3-fluorophenyl)-3-carboxy-7-chloro-(4H)-4-benzopyranone; 2-(3-fluorophenyl)-3-carboxy-6-chloro-(4H)-4-benzopyranone; 2-(3-fluorophenyl)-3-carboxy-6-bromo-(4H)-4-benzopyranone; 2-(3-fluorophenyl)-3-carboxy-7-methoxy-(4H)-4-benzopyranone; 2-(3,5-difluorophenyl)-3-carboxy-(4H)-4-benzopyranone; 2-(3,5-difluorophenyl)-3-carboxy-8-methyl-(4H)-4-benzopyranone; 2-(3,5-difluorophenyl)-3-carboxy-7-methyl-(4H)-4-benzopyranone; 2-(3,5-difluorophenyl)-3-carboxy-6-methyl-(4H)-4-benzopyranone; 2-(3,5-difluorophenyl)-3-carboxy-6-chloro-(4H)-4-benzopyranone; 2-(3,5-difluorophenyl)-3-carboxy-6-bromo-(4H)-4-benzopyranone; 2-(2,3-difluorophenyl)-3-carboxy-8-methyl-(4H)-4-benzopyranone; 2-(2,3-difluorophenyl)-3-carboxy-7-methyl-(4H)-4-benzopyranone; 2-(2,3-difluorophenyl)-3-carboxy-6-methyl-(4H)-4-benzopyranone; 2-(2,3-difluorophenyl)-3-carboxy-7-chloro-(4H)-4-benzopyranone; 2-(2,3-difluorophenyl)-3-carboxy-6-chloro-(4H)-4-benzopyranone; 2-(2,3-difluorophenyl)-3-carboxy-6-bromo-(4H)-4-benzopyranone; 2-(2,5-difluorophenyl)-3-carboxy-8-methyl-(4H)-4-benzopyranone; 2-(2,5-difluorophenyl)-3-carboxy-7-methyl-(4H)-4-benzopyranone; 2-(2,5-difluorophenyl)-3-carboxy-6-methyl-(4H)-4-benzopyranone; 2-(2,5-difluorophenyl)-3-carboxy-7-chloro-(4H)-4-benzopyranone; 2-(2,5-difluorophenyl)-3-carboxy-6-chloro-(4H)-4-benzopyranone; 2-(2,5-difluorophenyl)-3-carboxy-6-bromo-(4H)-4-benzopyranone; 2-(3,4-difluorophenyl)-3-carboxy-8-methyl-(4H)-4-benzopyranone; 2-(3,4-difluorophenyl)-3-carboxy-7-methyl-(4H)-4-benzopyranone; 2-(3,4-difluorophenyl)-3-carboxy-6-methyl-(4H)-4-benzopyranone; 2-(3,4-difluorophenyl)-3-carboxy-6-chloro-(4H)-4-benzopyranone; 2-(4-chlorophenyl)-3-carboxy-8-methyl-(4H)-4-benzopyranone; 2-(4-chlorophenyl)-3-carboxy-7-methyl-(4H)-4-benzopyranone; 2-(4-chlorophenyl)-3-carboxy-6-methyl-(4H)-4-benzopyranone; 2-(4-chlorophenyl)-3-carboxy-6-chloro-(4H)-4-benzopyranone; 2-(4-chlorophenyl)-3-carboxy-6-bromo-(4H)-4-benzopyranone; 2-(4-chlorophenyl)-3-carboxy-(4H)-4-benzopyranone; and 2-(4-chlorophenyl)-3-carboxy-8-methoxy-(4H)-4-benzopyranone, and the TNF overexpression disease is selected from the group consisting of rheumatoid arthritis, juvenile rheumatoid arthritis, inflammatory bowel disease, Crohn's disease, ulcerative colitis, psoriasis, plaque psoriasis, juvenile plaque psoriasis, psoriatic arthritis, polyarticular juvenile idiopathic arthritis, Behcet's enteritis, ankylosing spondylitis, axial spondyloarthritis, juvenile enthesitis-related arthritis, osteoarthritis, polymyalgia rheumatica, multiple sclerosis, systemic lupus erythematosus, asthma, Sjogren's syndrome, pneumonia, chronic obstructive pulmonary disease, sarcoidosis, granuloma annulare, Wegener's granulomatosis, arteriosclerosis, vasculitis, heart failure, myocardial infarction, kidney injury, nephritis, graft versus host disease, dementia, Alzheimer's disease, Parkinson's disease, pain, uveitis, Behcet's disease, hidradenitis suppurativa, *Pityriasis rubra pilaris*, necrobiosis lipoidica diabeticorum, pyoderma gangrenosum, Sweet's syndrome, subcorneal pustular dermatosis, scleroderma, neutrophilic dermatitis, dermatomyositis, sepsis, and septic shock.

5. The method of claim 4, wherein the animal is a human.

6. The method of claim 4, wherein the animal is not a human.

* * * * *